US009044456B2

(12) United States Patent
Preiss-Bloom

(10) Patent No.: US 9,044,456 B2
(45) Date of Patent: Jun. 2, 2015

(54) CROSS-LINKED COMPOSITIONS

(71) Applicant: Lifebond Ltd., Caesarea (IL)

(72) Inventor: Orahn Preiss-Bloom, Zichron Yakov (IL)

(73) Assignee: LIFEBOND LTD., Caesarea (IL)

( * ) Notice: Subject to any disclaimer, the term of this patent is extended or adjusted under 35 U.S.C. 154(b) by 0 days.

(21) Appl. No.: 14/188,711

(22) Filed: Feb. 25, 2014

(65) Prior Publication Data

US 2014/0314732 A1  Oct. 23, 2014

Related U.S. Application Data

(62) Division of application No. 13/555,656, filed on Jul. 23, 2012, now Pat. No. 8,703,117, which is a division of application No. 13/000,021, filed as application No. PCT/IB2009/052605 on Jun. 18, 2009, now Pat. No. 8,367,388.

(60) Provisional application No. 61/129,322, filed on Jun. 18, 2008.

(51) Int. Cl.
*A61K 38/39* (2006.01)
*A61K 8/04* (2006.01)
*A61K 8/20* (2006.01)
*A61K 8/36* (2006.01)
*A61K 8/365* (2006.01)
*A61K 8/60* (2006.01)
*A61K 8/65* (2006.01)
*A61K 8/66* (2006.01)
*A61K 9/00* (2006.01)
*A61K 9/19* (2006.01)
*A61K 47/02* (2006.01)
*A61K 47/10* (2006.01)
*A61K 47/18* (2006.01)
*A61K 47/20* (2006.01)
*A61K 47/26* (2006.01)
*A61K 47/32* (2006.01)
*A61K 47/36* (2006.01)
*A61K 47/38* (2006.01)
*A61K 47/42* (2006.01)
*A61K 47/46* (2006.01)
*A61L 15/24* (2006.01)
*A61L 15/26* (2006.01)
*A61L 15/32* (2006.01)
*A61L 26/00* (2006.01)
*A61Q 19/00* (2006.01)
*C08H 1/06* (2006.01)
*C08L 89/06* (2006.01)

(52) U.S. Cl.
CPC .............. *A61K 38/39* (2013.01); *A61K 8/042* (2013.01); *A61K 8/20* (2013.01); *A61K 8/36* (2013.01); *A61K 8/365* (2013.01); *A61K 8/60* (2013.01); *A61K 8/65* (2013.01); *A61K 8/66* (2013.01); *A61K 9/0014* (2013.01); *A61K 9/19* (2013.01); *A61K 47/02* (2013.01); *A61K 47/10* (2013.01); *A61K 47/18* (2013.01); *A61K 47/183* (2013.01); *A61K 47/20* (2013.01); *A61K 47/26* (2013.01); *A61K 47/32* (2013.01); *A61K 47/36* (2013.01); *A61K 47/38* (2013.01); *A61K 47/42* (2013.01); *A61K 47/46* (2013.01); *A61L 15/24* (2013.01); *A61L 15/26* (2013.01); *A61L 15/32* (2013.01); *A61L 26/0014* (2013.01); *A61L 26/0019* (2013.01); *A61L 26/0038* (2013.01); *A61Q 19/00* (2013.01); *C08H 1/06* (2013.01); *C08L 89/06* (2013.01)

(58) Field of Classification Search
None
See application file for complete search history.

(56) References Cited

U.S. PATENT DOCUMENTS

| | | |
|---|---|---|
| 1,394,654 A | 10/1921 | Tressler |
| 1,844,679 A | 2/1932 | Price |
| 1,873,580 A | 8/1932 | Hailwood |
| 1,950,483 A | 5/1934 | Christopher et al. |
| 2,048,499 A | 7/1936 | Gellednien |
| 2,126,305 A | 8/1938 | Babcok |
| 2,166,074 A | 7/1939 | Reichel |
| 2,398,004 A | 5/1946 | Houck et al. |
| 2,417,713 A | 3/1947 | Stein |
| 2,558,065 A | 6/1951 | Tice |

(Continued)

FOREIGN PATENT DOCUMENTS

| | | |
|---|---|---|
| EP | 0073908 A1 | 3/1983 |
| EP | 0302953 | 2/1989 |

(Continued)

OTHER PUBLICATIONS

De Carvalho & Grosso, "Characterization of gelatin based films modified with transglutaminase, glyoxal and formaldehyde", Food Hydrocolloids 18 (2004) 717-726.*
Dong et al., "Optimization of cross-linking parameters during production of transglutaminase-hardened spherical multinuclear microcapsules by complex coacervation" Colloids and Surfaces B: Biointerfaces 63 (2008) 41-47.*
Bertoni et al., "Transglutaminase reactivity with gelatine: perspective applications in tissue engineering", Biotechnol Lett (2006) 28:697-702. DOI 10.1007/s10529-006-9046-2.*

(Continued)

*Primary Examiner* — Suzanne M Noakes
(74) *Attorney, Agent, or Firm* — Graeser Associates International Inc; Dvorah Graeser

(57) ABSTRACT

Improved compositions comprising a cross-linkable protein or polypeptide, and a non-toxic material which induces cross-linking of the cross-linkable protein. The compositions are optionally and preferably prepared in a non-phosphate buffer solvent. Optionally and preferably, the cross-linkable protein includes gelatin and any gelatin variant or variant protein as described herein. Optionally and preferably, the non-toxic material comprises transglutaminase (TG), which may optionally comprise any type of calcium dependent or independent transglutaminase, which may for example optionally be a microbial transglutaminase (mTG).

25 Claims, 16 Drawing Sheets

(56) References Cited

U.S. PATENT DOCUMENTS

| | | | |
|---|---|---|---|
| 2,658,001 | A | 11/1953 | Young |
| 2,719,145 | A | 9/1955 | Skelton et al. |
| 2,803,548 | A | 8/1957 | Hagetry |
| 3,220,845 | A | 11/1965 | Fort |
| 3,600,482 | A | 8/1971 | Schwendeman |
| 3,939,001 | A | 2/1976 | Clausi et al. |
| 3,988,479 | A | 10/1976 | Stephan |
| 4,188,373 | A | 2/1980 | Krezanoski |
| 4,188,465 | A | 2/1980 | Schneider et al. |
| 4,224,348 | A | 9/1980 | Hayashi |
| 4,344,181 | A | 8/1982 | Baecklund |
| 4,426,443 | A | 1/1984 | Shank |
| 4,478,822 | A | 10/1984 | Haslam |
| 4,527,906 | A | 7/1985 | Jezbera |
| 4,572,906 | A | 2/1986 | Sparkes |
| 4,605,513 | A | 8/1986 | DiMarchi |
| 4,651,725 | A | 3/1987 | Kifune |
| 4,711,848 | A | 12/1987 | Insley |
| 4,729,897 | A | 3/1988 | Poppe |
| 4,837,379 | A | 6/1989 | Weinberg |
| 4,891,319 | A | 1/1990 | Roser |
| 4,931,501 | A | 6/1990 | Lai et al. |
| 4,948,540 | A | 8/1990 | Nigam |
| 4,952,618 | A | 8/1990 | Olsen |
| 4,985,250 | A | 1/1991 | Bee et al. |
| 5,015,677 | A | 5/1991 | Benedict et al. |
| 5,059,636 | A | 10/1991 | Grenga |
| 5,147,344 | A | 9/1992 | Sachau |
| 5,209,776 | A | 5/1993 | Bass |
| 5,399,361 | A | 3/1995 | Song |
| 5,428,014 | A | 6/1995 | Labroo |
| 5,433,943 | A | 7/1995 | Osipow |
| 5,441,193 | A | 8/1995 | Gravener |
| 5,480,644 | A | 1/1996 | Freed |
| 5,487,889 | A | 1/1996 | Eckert et al. |
| 5,487,895 | A | 1/1996 | Dapper |
| 5,490,984 | A | 2/1996 | Freed |
| 5,503,638 | A | 4/1996 | Cooper et al. |
| 5,525,335 | A | 6/1996 | Kitahara et al. |
| 5,549,628 | A | 8/1996 | Cooper et al. |
| 5,549,904 | A | 8/1996 | Juergensen |
| 5,575,803 | A | 11/1996 | Cooper et al. |
| 5,618,312 | A | 4/1997 | Yui |
| 5,702,409 | A | 12/1997 | Rayburn et al. |
| 5,736,132 | A | 4/1998 | Juergensen |
| 5,752,965 | A | 5/1998 | Francis et al. |
| 5,752,974 | A | 5/1998 | Rhee |
| 5,810,855 | A | 9/1998 | Rayburn |
| 5,834,232 | A | 11/1998 | Bishop |
| 5,895,412 | A | 4/1999 | Tucker |
| 5,931,165 | A | 8/1999 | Reich |
| 5,939,385 | A | 8/1999 | Labroo |
| 5,948,662 | A | 9/1999 | Kobayashi |
| 6,007,613 | A | 12/1999 | Izoret |
| 6,030,821 | A | 2/2000 | Soeda |
| 6,054,122 | A | 4/2000 | MacPhee et al. |
| 6,063,061 | A | 5/2000 | Wallace |
| 6,066,325 | A | 5/2000 | Wallace |
| 6,083,524 | A | 7/2000 | Sawhney |
| 6,100,053 | A | 8/2000 | Bech |
| 6,107,401 | A | 8/2000 | Dado et al. |
| 6,117,425 | A | 9/2000 | MacPhee et al. |
| 6,121,013 | A | 9/2000 | Yamaguchi |
| 6,132,759 | A | 10/2000 | Schacht |
| 6,136,341 | A | 10/2000 | Petito |
| 6,156,330 | A | 12/2000 | Tsukada |
| 6,162,241 | A | 12/2000 | Coury et al. |
| 6,190,896 | B1 | 2/2001 | Fraij |
| 6,197,325 | B1 | 3/2001 | MacPhee et al. |
| 6,228,393 | B1 | 5/2001 | DiCosmo |
| 6,267,957 | B1 | 7/2001 | Green |
| 6,303,752 | B1 | 10/2001 | Olsen |
| 6,371,975 | B2 | 4/2002 | Cruise |
| 6,413,742 | B1 | 7/2002 | Olsen |
| 6,420,148 | B2 | 7/2002 | Yamaguchi |
| 6,454,787 | B1 | 9/2002 | Maddalo |
| 6,458,386 | B1 | 10/2002 | Schacht |
| 6,465,001 | B1 | 10/2002 | Hubbell |
| 6,475,516 | B2 | 11/2002 | DiCosmo |
| 6,509,039 | B1 | 1/2003 | Nies |
| 6,527,751 | B2 | 3/2003 | Fischer et al. |
| 6,531,147 | B2 | 3/2003 | Sawhney |
| 6,544,227 | B2 | 4/2003 | Sahatjian |
| 6,559,119 | B1 | 5/2003 | Burgess et al. |
| 6,576,685 | B2 | 6/2003 | Stedronsky |
| 6,605,066 | B1 | 8/2003 | Gravagna et al. |
| 6,610,043 | B1 | 8/2003 | Ingenito |
| 6,656,193 | B2 | 12/2003 | Grant et al. |
| 6,663,594 | B2 | 12/2003 | Sahatjian |
| 6,682,760 | B2 | 1/2004 | Noff |
| 6,704,210 | B1 | 3/2004 | Myers |
| 6,706,690 | B2 | 3/2004 | Reich |
| 6,762,336 | B1 | 7/2004 | Macphee |
| 6,773,156 | B2 | 8/2004 | Henning |
| 6,833,258 | B2 | 12/2004 | Yokoyama |
| 6,863,783 | B2 | 3/2005 | Lin |
| 6,875,796 | B2 | 4/2005 | Stedronsky |
| 6,939,358 | B2 | 9/2005 | Palacios et al. |
| 6,992,172 | B1 | 1/2006 | Chang |
| 7,019,191 | B2 | 3/2006 | Looney |
| 7,045,601 | B2 | 5/2006 | Metzner |
| 7,074,981 | B2 | 7/2006 | Chalmers |
| 7,108,876 | B2 | 9/2006 | Grindstaff |
| 7,109,163 | B2 | 9/2006 | Pendharkar |
| 7,129,210 | B2 | 10/2006 | Lowinger |
| 7,186,684 | B2 | 3/2007 | Pendharkar |
| 7,189,410 | B1 | 3/2007 | Drohan et al. |
| 7,196,054 | B1 | 3/2007 | Drohan et al. |
| 7,208,171 | B2 | 4/2007 | Messersmith et al. |
| 7,208,179 | B1 | 4/2007 | Drohan et al. |
| 7,229,959 | B1 | 6/2007 | Drohan et al. |
| 7,241,730 | B2 | 7/2007 | Hubbell |
| 7,285,580 | B2 | 10/2007 | Stedronsky |
| 7,320,962 | B2 | 1/2008 | Reich |
| 7,435,425 | B2 | 10/2008 | Qian |
| 7,459,425 | B2 | 12/2008 | Wan et al. |
| 7,468,350 | B2 | 12/2008 | Gong |
| 7,766,891 | B2 | 8/2010 | McGurk |
| 7,998,466 | B2 | 8/2011 | Hadba |
| 8,133,484 | B2 | 3/2012 | Preiss-Bloom et al. |
| 8,367,388 | B2 | 2/2013 | Bloom et al. |
| 2001/0018598 | A1 | 8/2001 | Cruise |
| 2002/0015724 | A1 | 2/2002 | Yang |
| 2003/0008831 | A1 | 1/2003 | Yang |
| 2003/0035786 | A1 | 2/2003 | Hendriks |
| 2003/0120284 | A1 | 6/2003 | Palacios et al. |
| 2003/0135238 | A1 | 7/2003 | Milbocker |
| 2003/0219857 | A1 | 11/2003 | Chou |
| 2003/0232944 | A1 | 12/2003 | Fehr et al. |
| 2004/0093029 | A1 | 5/2004 | Zubik et al. |
| 2004/0106344 | A1 | 6/2004 | Looney |
| 2004/0131728 | A1 | 7/2004 | Ootzuka et al. |
| 2005/0113937 | A1 | 5/2005 | Binette et al. |
| 2005/0129733 | A1 | 6/2005 | Milbocker |
| 2005/0147646 | A1 | 7/2005 | Nilsson |
| 2005/0209441 | A1 | 9/2005 | Lile |
| 2005/0238683 | A1 | 10/2005 | Adhikari et al. |
| 2005/0249839 | A1 | 11/2005 | Ishida |
| 2005/0271727 | A1 | 12/2005 | Yao |
| 2006/0078962 | A1 | 4/2006 | Chen et al. |
| 2006/0100138 | A1 | 5/2006 | Olsen |
| 2006/0155234 | A1 | 7/2006 | Macphee |
| 2006/0258560 | A1 | 11/2006 | Yang et al. |
| 2006/0269590 | A1 | 11/2006 | Trotter |
| 2007/0021703 | A1 | 1/2007 | McCarthy |
| 2007/0082023 | A1 | 4/2007 | Hopman |
| 2007/0128152 | A1 | 6/2007 | Hadba |
| 2007/0172432 | A1 | 7/2007 | Stopek |
| 2007/0246505 | A1 | 10/2007 | Pace-Florida et al. |
| 2008/0187591 | A1 | 8/2008 | Rhee |
| 2008/0195037 | A1 | 8/2008 | Hissong |
| 2008/0213243 | A1 | 9/2008 | Preiss-Bloom |
| 2008/0260801 | A1 | 10/2008 | Ahlers et al. |
| 2008/0286376 | A1 | 11/2008 | Qian |

(56) References Cited

U.S. PATENT DOCUMENTS

| | | |
|---|---|---|
| 2009/0175946 A1 | 7/2009 | Gaissmaier et al. |
| 2009/0191269 A1 | 7/2009 | Gaissmaier et al. |
| 2010/0008989 A1 | 1/2010 | Attar et al. |

FOREIGN PATENT DOCUMENTS

| | | |
|---|---|---|
| EP | 0707474 | 4/1996 |
| EP | 0726317 | 8/1996 |
| EP | 0745670 | 12/1996 |
| EP | 0777726 | 6/1997 |
| EP | 0815742 | 1/1998 |
| EP | 0871712 | 10/1998 |
| EP | 0876166 | 11/1998 |
| EP | 0927053 | 7/1999 |
| EP | 0947142 | 10/1999 |
| EP | 0982038 | 3/2000 |
| EP | 1124590 | 8/2001 |
| EP | 1263327 | 12/2002 |
| EP | 1267826 | 1/2003 |
| EP | 1267876 | 1/2003 |
| EP | 1288264 | 3/2003 |
| EP | 1372492 | 1/2004 |
| EP | 1494730 | 1/2005 |
| EP | 1574229 | 9/2005 |
| EP | 1857494 | 11/2007 |
| EP | 1948260 | 7/2008 |
| EP | 2133069 | 12/2009 |
| JP | 2204407 | 8/1990 |
| JP | 2255888 | 10/1990 |
| JP | 7328108 | 12/1995 |
| JP | 10510183 | 10/1998 |
| JP | 2002515300 A | 5/2002 |
| JP | 2004283371 A | 10/2004 |
| JP | 2006503612 A | 2/2006 |
| JP | 07227228 | 9/2007 |
| WO | WO9617929 | 6/1996 |
| WO | WO/96/40791 | 12/1996 |
| WO | WO/97/22372 | 6/1997 |
| WO | 9729715 A1 | 8/1997 |
| WO | WO9729715 | 8/1997 |
| WO | 9737694 A1 | 10/1997 |
| WO | 9740701 | 11/1997 |
| WO | 9741899 | 11/1997 |
| WO | WO/98/35026 | 8/1998 |
| WO | WO/00/22103 | 4/2000 |
| WO | WO/00/76533 | 12/2000 |
| WO | WO/01/15750 | 3/2001 |
| WO | 02085422 | 10/2002 |
| WO | 02098937 A1 | 12/2002 |
| WO | WO/03/011352 | 2/2003 |
| WO | WO/03/072155 | 9/2003 |
| WO | WO/03/072157 | 9/2003 |
| WO | WO/03/074004 | 9/2003 |
| WO | WO03/086493 | 10/2003 |
| WO | WO03080144 | 10/2003 |
| WO | WO2004004875 | 1/2004 |
| WO | WO/2004/014969 | 2/2004 |
| WO | 2004024195 A1 | 3/2004 |
| WO | WO2004/028404 | 4/2004 |
| WO | WO/2004/029096 | 4/2004 |
| WO | WO/2004/098671 | 11/2004 |
| WO | WO/2004/105485 | 12/2004 |
| WO | WO/2005/061701 | 7/2005 |
| WO | WO/2006/014567 | 2/2006 |
| WO | WO/2006/014568 | 2/2006 |
| WO | WO2006016809 | 2/2006 |
| WO | WO2006027622 | 3/2006 |
| WO | WO2006056700 | 6/2006 |
| WO | 2006086479 A2 | 8/2006 |
| WO | 2006128685 | 12/2006 |
| WO | WO/2006/134148 | 12/2006 |
| WO | WO/2007/008229 | 1/2007 |
| WO | WO/2008/006545 | 1/2007 |
| WO | 2007057175 A2 | 5/2007 |
| WO | WO2007057175 | 5/2007 |
| WO | WO/2007/122232 | 11/2007 |
| WO | WO/2007/123350 | 11/2007 |
| WO | WO/2007/126411 | 11/2007 |
| WO | WO/2007/134118 | 11/2007 |
| WO | WO2008006544 | 1/2008 |
| WO | WO/2008/016983 | 2/2008 |
| WO | 2008076407 | 6/2008 |
| WO | 2008076407 A2 | 6/2008 |
| WO | WO/2008/073938 | 6/2008 |
| WO | WO/2008/103891 | 8/2008 |
| WO | WO/2009/012882 | 1/2009 |
| WO | WO/2009/026158 | 2/2009 |
| WO | WO/2009/036014 | 3/2009 |
| WO | WO/2009/073193 | 6/2009 |
| WO | WO/2009/105614 | 8/2009 |
| WO | 2009153748 A2 | 12/2009 |
| WO | 2009153750 | 12/2009 |
| WO | 2009153751 A2 | 12/2009 |
| WO | WO/2010/027471 | 3/2010 |

OTHER PUBLICATIONS

Examination Report for EP2133069 mailed Apr. 4, 2013.
Biomacromolecules, 2004, vol. 5, No. 4, p. 1270-1279.
de Carvalhoet al,; 1997; Physical gelation under shear for gelatin gels. Rheologica Acta 36(6): 591-609.
Examination Report for EP2303344 mailed Jun. 11, 2013.
Examination Report for EP2515957 mailed Jun. 24, 2013.
Extended Search report for EP2586467 mailed Jun. 17, 2013.
Journal of Biomedical Materials Research. Part B, Applied Biomaterials., 2006, 5, vol. 77, No. 2, p. 416-422.
Kwon, j. 2010; Rheological Behaviour of Gelatin at High Shear Rates. Ph.D Dissertation—University of Florida pp. 1-100. specif. pp. 27-28, 46.
Office Action for CA 2,728,187 mailed Apr. 2, 2013.
Office Action for CN 102124058 A mailed May 9, 2013.
Office Action for CN 101854960 A mailed Apr. 3, 2013.
Office Action for JP 2011-525128 mailed Aug. 6, 2013.
Office Action for JP2011-267107 mailed Jul. 23, 2013.
Orthodontics and Craniofacial Research, 2005, vol. 8, No. 3, p. 145-149.
Viscosity. Encyclopedia entry (online). Wikipedia, the free encyclopedia. "Dynamic Viscosity", p. 6 line 10; "Liquids", p. 9 line 7-8 [URL: http://en.wikipedia.org/wiki/viscosity]; undated.
International Search Report for PCT/IB2009/052600, published Sep. 30, 2010.
International Search Report for PCT/IB2009/052605, published Jun. 17, 2010.
International Search Report for PCT/IB2009/052607, published Jan. 20, 2011.
EP Application 09766288.6 Office Action dated Jun. 6, 2012.
Abrams GW et al. The incidence of corneal abnormalities in the Silicone Study. Silicone Study Report 7. Arch Ophthalmol 1995;113:764-769.
Alio JL et al. A new acrylic tissue adhesive for conjunctival surgery: experimental study. Ophthalmic Res 2003, 35:306-312.
Bloom JN et al. A Light-activated surgical adhesive for sutureless ophthalmic surgery, Arch Ophthamol 2003; 121: 1591-1595.
Cooper et al. J. Thorac. Cardiovasc. Surg. 109106-116, 1995.
Cooper et al. J. Thorac. Cardiovasc. Surg. 1121319-1329, 1996.
Eidt et al. Am J Surg 1999:178:511-516.
Ghazi NG et al. Pathology and pathogenesis of retinal detachment. Eye 2002;16:411-421.
Grotenhuis Andre J. Healthcare Economics Costs of postoperative cerebrospinal fluid leakage: 1-year, retrospective analysis of 412 consecutive nontrauma cases, Surgical Neurology 64 (2005) 490-494.
Johanning JM et al. Femoral artery infections associated with percutaneous arterial closure devices, J Vasc Surg 2001;34:983-985.
Katloff et al. A Comparison of Median Sternotomy and Thoracoscopic Approaches, Chest 110:1399-1406,1996.
Ninan L et al. Adhesive strength of marine mussel extracts of procine skin. Biomaterials 2003;24:4091-4099.

(56) References Cited

OTHER PUBLICATIONS

Olivieri MP et al. Surface properties of mussel adhesive protein component films. Biomaterials 1992,13:1000-1008.
Shahidi M et al. Retinal topography and thickness mapping in atrophic age related macular degeneration. Br J Ophthalmol 2002;86:623-626.
Smith TP et al. Infectious complications resulting from use of hemostatic puncture closure devices, Am J Surg 2001;182:658-662.
Swanson et al. J Am. Coll Surg: 185:25-32, 1997.
Toursarkissian B et al. Changing Pattern of Access Site Complications with the Use of Percutaneous Closure Devices, Vasc Endovasc Surg 2001;35:203-206.
Velazquez AJ at el., New dendritic adhesives for sutureless ophthalmic surgical procedures: in viro studies of corneal laceration repair. Arch Ophthamol 2004;122:867-870.
Agricultural and Biological Chemistry, 1989 (53,10), 2619-2623.
De Joung et al. J. Agric.Food.Chem, 2001(49), 3389-3393.
Gan et al. Food Hydrocolloids 2009 (23), 1398-1405.
Hirose at al. Gelation of Bovine Serum Albumin by Glutathione, J Food Sci, 1990 (55,4) 915-917.
Kang et al. Effect of Disulfide Bond Reduction on Bovine Serum Albumin—Stabilized Emulsion Gel Formed by Microbial Transglutaminase, J Food Sci, 2003 (68,7), 2215-2220.
Lee et al. Agricultural and Biological Chemistry, vol. 55, No. 8 (1991) 2057-2062.
Tobitani et al, Heat-Induced Gelation of Globular Proteins. 1. Model for the Effects of Time and Temperature on the Gelation Time of BSA Gels, Macromolecules, 1997 (30,17), 4845-4854.
Alur HH et al. Transmucosal sustained-delivery of chlorpheniramine maleate in rabbits using a novel, natural mucoadhesive gum as an excipient in buccal tablets, Int. J. Pharm., 1999, 88(1), 1-10.
Babin H et al. Food Hydrocolloids 2001, 15, 271-276.
Bernkop-Schnurch A et al. Pharm. Res., 1999, 16, 6, 876-81.32.
Buchta C et al. Biochemical characterization of autologous fibrin sealants produced by CryoSeal and Vivostat in comparison to the homologous fibrin sealant product Tissucol/Tisseel, Biomaterials 2005, 26, 6233-41.27-30.
Pusateri, 2004 J Biomed Mater Res B, 15; 70(1): 114-121.
Burzio LA et al. Cross-Linking in Adhesive Quinoproteins: Studies with Model Decapeptides, Biochemistry 2000, 39, 11147-53.
Deacon MP et al. Structure and Mucoadhesion of Mussel Glue Protein in Dilute Solution, Biochemistry 1998, 37, 14108-12.
Ehrbar M et al. Enzymatic formation of modular cell-instructive fibrin analogs for tissue engineering, Biomaterials 2007, 28, 3856-66.
Fisher MT et al, PNAS 103, 2006: p. 13265-6.
Garcia Y et al. Assessment of cell viability in a three-dimensional enzymatically cross-linked collagen scaffold. J Mater Sci Mater Med. Oct. 2007;18(10):1991-2001.
Ghebremeskel et al 2006, International Journal of Pharmaceutics 328: 119-129.
Yokoyama K et al. Protein Exp & Purif 26, 2002: p. 329-335 2002.
Rajagopalan et al. J Biologica Chem 236(4), 1961.
Glickman M et al. Arch Surg 2002, 137, 326-31.
Gutowska A et al. Anat Rec 2001, 263, 342-349.
Haines-Butterick L et al. Controlling hydrogelation kinetics by peptide design for three-dimensional encapsulation and injectable delivery of cells, Proc Natl Acad Sci U S A 2007, 104, 7791-6.
Hussain I et al, Animal Feed science and Technology, 1996;62 (2), p. 121-129.
Ikura K et al. Biosci Biotechnol Biochem. 66(6), 2002, p. 1412-1414.
Iwata H et al. A novel surgical glue composed of gelatin and N-hydroxysuccinimide activated poly(L-glutamic acid): Part 1. Synthesis of activated poly(L-glutamic acid) and its gelation with gelatin; Biomaterials 1998, 19, 1869-76.
Jackson M. Fibrin sealants in surgical practice: An overview, Am J Surg 2001, 182, 1S-7S.
Juggi JS et al., In-Vivo Studies with a cation Exchange Resin Mixture in the Removal of Excessive Ammonium from the Extracorporeal Circulation System. ANZ J Surg 1968;38 (2) p. 194-201.

O'Halloran DM et al. Characterization of a microbial transglutaminase cross-linked type II collagen scaffold. Tissue Eng. Jun. 2006; 12(6): 1467-74.
Ohtake Y et al. Transglutaminase catalyzed dissociation and association of protein-polyamine complex; Life Sciences 2007; 81 ,7: p. 577-584.
Otani Y et al. Sealing Effect of Rapidly Curable Gelatin-Poly (L-Glutamic Acid) Hydrogel Glue on Lung Air Leak; Ann Thorac Surg 1999, 67, 922-6.
Rodriguez et al. Combined effect of plasticizers and surfactants on the physical properties of starch based edible films; Food Research International 39 (2006) 840-6.
Sanbom TJ et al. In situ crosslinking of a biomimetic peptide-PEGhydrogel via thermally triggered activation of factor XII; Biomaterials 2002, 23, 2703-10.
Serafinie-Fracassini D et al. First Evidence for Polyamine Conjugation Mediated by an Enzymic Activity in Plants; Plant Physiol. (1988) 87, 757-761.
Shojaei AM et al. Mechanisms of buccal mucoadhesion of novel copolymers of acrylic acid and polyethylene glycol monomethylether monomethacrylate; Journal of Control Release, 1997, 47, 151-61.27.
Silva EA et al. Spatiotemporal control of vascular endothelial growth factor delivery from injectable hydrogels enhances angiogenesis; J Thromb Haemost 2007, 5, 590-8.
Silverman HG et al. Understanding Marine Mussel Adhesion; Mar Biotechnol (NY) 2007, 9, 661-81.
Sperinde J et al. Control and Prediction of Gelation Kinetics in Enzymatically Cross-Linked Poly(ethylene glycol) Hydrogels; Macromolecules 2000, 33, 5476-5480.
Strausberg RL et al, Protein-based medical adhesives, Trends Biotechnol 1990;8:53-5.
Sung HW et al. Evaluation of gelatin hydrogel crosslinked with various crosslinking agents as bioadhesives: In vitro study; J Biomed Mater Res 1999, 46, 520-30.
Ulijn RV et al. Designing peptide based nanomaterials; Chem Soc Rev 2008, 37, 664-75.
Langoth N et al. Development of buccal drug delivery systems based on a thiolated polymer, Int. J. Pharm., 2003, 252, 141-48.
Lehr C et al. Pharma Res., 1992, 9(4), 547-53.
Lim DW et al. In Situ Cross-Linking of Elastin-like Polypeptide Block Copolymers for Tissue Repair; Biomacromolecules 2008, 9, 222-30.
Ma et al. Enhanced biological stability of collagen porous scaffolds by using amino acids as novel cross-linking bridges; Biomaterials. 2004, 25(15): p. 2997-3004.
Mahoney MJ et al. Contrasting effects of collagen and bFGF-2 on neural cell function in degradable synthetic PEG hydrogels; J Biomed Mater Res A 2007, 81, 269-78.
McDowell et al. Rotational Echo Double Resonance Detection of Cross-links Formed in Mussel Byssus under High-Flow Stress; Biol Chem 1999, 274,20293-5.
Motoki M et al. Transglutaminase and its use for food processing; Trends in Food Science & Technology 1998, 9, 204-210.
Nakamura E et al. Role of glutamine and arginase in protection against ammonia-induced cell death in gastric epithelial cells, Am J of Phys. GI and Liver Phys, 2002; 46(6), p. G1264-G1275.
Jakob H. et al. (1984). J. Vasc. Surg. 1:171-180.
Japanese office action for corresponding Japanese application No. 2009-541417, mailed on Apr. 2, 2013.
Fernandez-Diaz, M.D. et al., "Gel Properties of Collagens from Skins of Cod (Gadus morhua) and Hake (Merluccius merluccius) and Their Modification by the Coenhancers Magnesium sulphate, Glycerol and Transglutaminase", Food Chemistry, 2001, vol. 74, pp. 161-167.
Examination report for corresponding Australian Application No. 2007334394, mailed Jul. 20, 2012.
Office action issued for corresponding European Application No. 11192607.7, mailed Jan. 2, 2013.
Office action issued for corresponding Chinese Application No. 200780051215.4, mailed Aug. 31, 2012.
Office action issued for corresponding Canadian Application No. 2672651, mailed Feb. 1, 2013.

(56) References Cited

OTHER PUBLICATIONS

Office action issued for corresponding Australian Application No. 2007334394, mailed Jan. 4, 2013.
Office action issued for corresponding Japanese Application No. 2009-541417, mailed Jan. 8, 2013.
Office action issued for corresponding European Application No. 7867783.8, mailed Jun. 27, 2012.
Office action issued for corresponding Chinese Application No. 200980131973.6, mailed Sep. 24, 2012.
Office action issued for corresponding European Application No. 9766287.8, mailed Mar. 12, 2013.
Office action issued for corresponding European Application No. 9766288.6, mailed Jun. 6, 2012.
Office action issued for corresponding European Application No. 11192607.7, mailed May 10, 2012.
Office action issued for corresponding European Application No. 12155067, mailed Jul. 3, 2012.
Search report issued for corresponding PCT Application No. PCT/IB2010/056008, mailed Apr. 19, 2011.
Drury et al, "Hydrogels for tissue engineering: scaffold design variables and applications", Biomaterials, vol. 24, Nov. 2003, pp. 4337-4351.
Search report issued for corresponding PCT Application No. PCT/IB2011/051714, mailed Nov. 30, 2011.
Search report issued for corresponding PCT Application No. PCT/IB2011/053505, mailed Mar. 9, 2012.
Office action issued for corresponding European Application No. 12187110, mailed Nov. 21, 2012.
Wichman et al, "Kinetics of Refolding of Completely Reduced Human-Serum Albumin", European Journal of Biochemistry, vol. 79, 1977, pp. 339-344.
Translation of office action from corresponding Chinese application No. 201110365186.7, mailed Dec. 23, 2013.
Translation of office action from corresponding Japanese application no. 2009-541417, mailed Dec. 3, 2013.
Notice of Opposition for corresponding EP application 07867783.8, mailed Dec. 3, 2013.
Werten MWT, et al. Secreted production of a custom-designed, highly hydrophilic gelatine in *Pichia pastoris*. protein Engineering, vol. 14, No. 6, 447-454, Jun. 2001.
Olsen D et al. Recombinant collagen and gelatin for drug delivery. Adv Drug Deily Rev. Nov. 28, 2003;55 (12) 1547-67.
Cui L, et al. Purification and characterization of transglutaminase from a newly isolated *Streptomyces hygroscopicus*. 2007: 105(2). p. 612-618.
Bertoni F, Barbani et al. Transglutaminase reactivity with gelatine: perspective applications in tissue engineering Biotechnol Lett (2006)28:697-702).
Broderick EP, et al. Enzymatic Stabilization of Gelatin-Based Scaffolds J Biomed Mater Res 72B: 37-42, 2005.
Folk JE, et al. Transglutaminase:mechanistic features of the active site as determined by kinetic and inhibitor studies. Biochim Biophys Acta. 1966; 122:244-64.
Chen et al. Biomacromolecules, vol. 4, 1558-1563, No. 6, 2003.
Haug et al. Food Hydrocolloids 18 (2004) 203-213.
D'Cruz NM, et al. Thermal Unfolding of Gelatin in Solids as Affected by the Glass Transition, J Food Science 2005: 70 (2), Kozlov PV, Burdygina GI.
Search Report for EP patent application 09162590.5 dated: Sep. 2, 2009.
Bello J, et al. Mechanism of Gelation of Gelatin. Influence of Certain Electrolytes on the Melting Points of Gels of Gelatin and Chemically Modified Gelatins. Am Chem Soc. Sep. 1956 (60). p. 1299-1306.
Crowe LM,et al. Is Trehalose Special for Preserving Dry Biomaterials? Biophysical Journal 1996 (71): 2087-2093.
Norie N, et al. Factors Affecting the Gelation of a Gelatin Solution in the Presence of Sugar. Journal of Home Economics of Japan. 55(2): p. 159-166 (2004).
J.M. Rocko et al. (1982). J. Trauma 22:635.

Harry B. Kram et al. Techniques of Splenic Preservation Using Fibrin Glue. The Journal of Trauma. vol. 30, No. 1 (97-101) 1990.
A.E. Pusateri et al. (2006). J. Trauma.. 60:674-682.
M.K. McDermott. et al: "Mechanical properties of biomimetic tissue adhesive based on the microbial transglutaminase-catalyzed crosslinking of gelatin" Biomacromolecules, ACS, Washington, DC, US, vol. 5, Jan. 1, 2004, pp. 1270-1279, XP002494450 ISSN: 1525-7797 [Retrieved on Apr. 21, 2004].
OA for EP patent application 09162590.5 dated: Jul. 6, 2010.
Ito A, J Biosci & Bioeng. 2003; 95(2):196-99.
OA for EP patent application 07867783.8 dated: Feb. 9, 2011.
D.B. Kendrick, Blood Program in WW II ( Washington, DC: Office of the Surgeon General, Department of Army; 1989), 363-368.
Jackson, M., et al (1996). J. of Surg. Res. 60:15-22.
Jackson, M., et al. (1997) Surg. Forum. XL, VIII:770-772.
E.M. Acheson. (2005). J. Trauma. 59(4): 865-74.
B.S. Kheirabadi. (2005). J. Trauma. 59(1): 25-34.
A.E. Pusateri. (2004). J Biomed. Mater. Res. B. Appl. Biomater. 15;70(1): 114-21.
J. L. Garza et al. (1990). J. Trauma. 30:512-513.
T.L. Matthew et al. (1990). Ann. Thorac. Surg. 50:40-44.
H Jakob et al (1984). J. Vasa Surg. 1:171-180.
R. Lerner et ak. (1990). J. Durge. Res 48:165-181.
MSabel et al. (2004). Eur. Spine J. 13 (l): S97-101.
MG Tucci. (2001). J. Bioactive & Comp Polymers. 1692): 145-157.
B Balakrishnan et al. (2005). Biomaterials. 26932): 6335-42.
FA Weaver et al. (2002). Ann. Vase Surg. 16(3): 286-93.
OA for EP patent application 07867783.8 dated: Jan. 28, 2010.
Crescenzi V, et al (2002). Biomacromolecules. 3:1384-1391.
Gorman, J.J; J Bio. Chem. 1980, 255, 419-427.
Kahlem, P.; Acad. Sci U.S.A. 1996, 93, 14580-14585.
Etoh, Y.; Biochem, Biophys. Res Commun. 1986, 136, 51-56.
Hohenadi, C.; J. Biol. Chem. 1955, 270, 23415-23420.
Gross, M.; J. Biol. Chem. 1975, 250, 4648-4655.
Groenen, P.; Eur. J. Biochem. 1994, 220, 795-799.
Grootjans, J. J. Biol. Chem. 1995, 270, 22855-22858.
Owen et al. N. Engl. J. Med. 309:694-698, 1983.
PCT Search Report for corresponding PCT application PCT/US07/025726, published Jan. 28, 2010.
Akira et al, Activity and Stability of Microbial Transglutaminase Modified with a Water-Soluble Polymer, JapaneseJournal of Polymer Science and Technology (Kobunshi Ronbunshu), vol. 58, No. 2, pp. 73-77 (Feb. 2001).
Office action issued for related EP 11768111.4 Mailed Feb. 27, 2014.
Office action from corresponding Chinese application No. CN 201080057151.0, mailed Nov. 27, 2013 (originalChinese language document).
Translation of summary of office action from corresponding Chinese application No. CN 201080057151.0. mailed Nov. 2013.
Spotnitz WD. Am J Surg 2001, 182, 8S-14S.
Office action issued for corresponding Japanese Application No. 2011-267107, mailed Feb. 4, 2014—Translation.
Office action issued for related Chinese Application 201180044965.5 Mailed Feb. 7, 2014—Translation.
Office action issued for related Chinese Application 201180044965.5 Mailed Feb. 7, 2014.
Chen et al, "Enzyme-catalyzed gel formation of gelatin and chitosan: potential for in situ applications", Biomaterials vol. 24 (2003) pp. 2831-2841.
Chen et al, "Gelatin-Based Biomimetic Tissue Adhesive. Potential for Retinal Reattachment", Published online Nov. 8, 2005 in Wiley InterScience (www.interscience.wiley.com). DOI: 10.1002/jbm.b.30439.
Nomura et al, "Improvement of Shark Type I Collagen with Microbial Transglutaminase in Urea", Biosci. Biotech. Biochem, vol. 65, 2001, pp. 982-985.
William D. Spotnitz, M.D. Commercial fibrin sealants in surgical care. The American Journal of Surgery (2001), 8S-14S, 182.
Hideraka Nagatomo, Gelatin-based adhesive has fibrin sealant benefit without use of blood products. Biosci, Biotechnol. Biochem, 2005, 128-136, 69 (1).

(56) References Cited

OTHER PUBLICATIONS

Blood Weekly Editors. Gelatin-based adhesive has fibrin sealant benefit without use of blood products, Copyright 2004, Blood Weekly via NewsRx.com.

OA for EP patent application 07867783.8 dated: Aug. 28, 2011.

QuikClot® ACS™ (Z-Medica, Wallington, CT). Aug. 10, 2005.

HemCon™ bandage (HemCon, Portland, Aug. 6, 2008).

Holcomb, J. B., et al. (1997). Surgical Clinics of North America. 77:943-952).

SAS_SAT 9_2 Users Guide, undated.

M. Gage Ochsner et al. Fibrin Glue as a Hemostatic Agent in Hepatic and Splenic Trauma. The Journal of Trauma. vol. 30, No. 7 1990. 884-887.

Xie Z-P et al: "A novel casting forming for cermics by gelatine and enzyme catalysis" Mar. 1, 2000, Journal of the European CERAMIc Society, Elsevier Science Publishers, Barking, Essex, GB, pp. 253-257, XP004185604.

Nio N et al: "Gelation Mechanism of Protein Solution by Transglutaminase" and Biological Chemistry, Japan Soc. for Bioscience, Biotechnology and Agrochem, Tokyo, JP pp. 851-855, 1985.

Otani Y et al : "Effect of additives on gelation and tissue adhesion of gelatin-poly (L-glutamic acid) mixture" Dec. 1, 1998, Biomaterials, Elsevier Science Publishers BV., Barking, GB,pp. 2167-2173.

Kozlov P V et al: "The structure and properties of solid gelatin and the principles of thier modification" Jun. 1, 1983, Polymer, Elsevier Science Publishers B.V, GB, pp. 651-666.

Ajinomoto GRAS summary for transglutaminase, Jun. 1997.

Office Action from related JP 2011-267107 received Oct. 7, 2014 (translation).

Office Action from related CN 081306558-E received Oct. 20, 2014 (translation).

Office Action from related CN 091101424-PVE received Sep. 1, 2014 (translation).

Office Action from related EP 11192607.7 received Aug. 5, 2014.

Yiming Biological Products Co., Ltd—Products—Transglutaminase—website as of Dec. 14, 2014.

Office Action of related JP2013265507 mailed Jan. 20, 2015.

Office Action of related JP2013265507 mailed Jan. 20, 2015 (Translated).

\* cited by examiner

CROSS-LINKED COMPOSITIONS

FIELD OF THE INVENTION

The present invention relates to improved cross-linked compositions comprising a cross-linkable protein and a non-toxic material which induces cross-linking of the cross-linkable protein.

BACKGROUND OF THE INVENTION

Biomaterials that can form gels in situ are useful for a variety of applications. In many cases, in situ gel-forming materials are used as injectable matrices for controlled drug delivery or injectable scaffolds for tissue engineering. (Gutowska A, Jeong B, Jasionowski M. *Anat Rec* 2001, 263, 342-349. Silva E A, Mooney D J. *J Thromb Haemost* 2007, 5, 590-8. Mahoney M J, Anseth K S. *J Biomed Mater Res A* 2007, 81, 269-78.) In situ gel-forming materials can also serve as adhesives to bond tissue or seal leaks (either gas or fluid) in a physiological environment.

Interest in soft tissue adhesives is growing because of the desire to replace or supplement sutures for wound closure (Glickman M, Gheissari A, Money S, Martin J, Ballard J. *Arch Surg* 2002, 137, 326-31; discussion 332. Pursifull N F, Morey A F. *Curr Opin Urol* 2007, 17, 396-401), the trends toward less invasive and cosmetic surgeries (*Tissue Adhesives in Clinical Medicine*; 2nd ed.; Quinn, J. V., Ed.; B C Decker: Hamilton, Ontario Canada, 2005. *Tissue Glue in Cosmetic Surgery*; Saltz, R.; Toriumi, D. M., Eds.; Quality Medical Publishing, Inc.,: St. Louis, Mo., USA 2004), and the need for emergency hemostasis (Pusateri A E, Holcomb J B, Kheirabadi B S, Alam H B, Wade C E, Ryan K L. *Journal of Trauma-Injury Infection and Critical Care* 2006, 60, 674-682. Acheson E M, Kheirabadi B S, Deguzman R, Dick E J, Holcomb J B. *Journal of Trauma-Injury Infection and Critical Care* 2005, 59, 865-874. Kheirabadi B S, Acheson E M, Deguzman R, Sondeen J L, Ryan K L, Delgado A, Dick E J, Holcomb J B. *Journal of Trauma-Injury Infection and Critical Care* 2005, 59, 25-34.)

In situ gel formation can be initiated by a variety of approaches. Chemical approaches to gel formation include the initiation of polymerization either by contact, as in cyanoacrylates, or external stimuli such as photo-initiation. Also, gel formation can be achieved by chemically crosslinking pre-formed polymers using either low molecular weight crosslinkers such as glutaraldehyde or carbodiimide (Otani Y, Tabata Y, Ikada Y. *Ann Thorac Surg* 1999, 67, 922-6. Sung H W, Huang D M, Chang W H, Huang R N, Hsu J C. *J Biomed Mater Res* 1999, 46, 520-30. Otani, Y.; Tabata, Y.; Ikada, Y. *Biomaterials* 1998, 19, 2167-73. Lim, D. W.; Nettles, D. L.; Setton, L. A.; Chilkoti, A. *Biomacromolecules* 2008, 9, 222-30), or activated substituents on the polymer (Iwata, H.; Matsuda, S.; Mitsuhashi, K.; Itoh, E.; Ikada, Y. *Biomaterials* 1998, 19, 1869-76).

In addition to chemical approaches, gel formation can be achieved through physical means using self-assembling peptides (Ellis-Behnke R G, Liang Y X, Tay D K, Kau P W, Schneider G E, Zhang S, Wu W, So K F. *Nanomedicine* 2006, 2, 207-15. Haines-Butterick L, Rajagopal K, Branco M, Salick D, Rughani R, Pilarz M, Lamm M S, Pochan D J, Schneider J P. *Proc Natl Acad Sci USA* 2007, 104, 7791-6. Ulijn R V, Smith A M. *Chem Soc Rev* 2008, 37, 664-75).

Finally, biological approaches to initiate gel formation have been investigated based on the crosslinking components from marine adhesives, such as mussel glue (Strausberg R L, Link R P. *Trends Biotechnol* 1990, 8, 53-7), or blood coagulation, as in fibrin sealants (Jackson M R. *Am J Surg* 2001, 182, 1S-7S. Spotnitz W D. *Am J Surg* 2001, 182, 8S-14S Buchta C, Hedrich H C, Macher M, Hocker P, Redl H. *Biomaterials* 2005, 26, 6233-41.27-30).

A variety of biomimetic approaches have also been considered for in situ gel formation. In these approaches, polymer crosslinking and gel formation are modeled after one of the crosslinking operations found in biology. The biological model that has probably attracted the most technological interest is the mussel glue that sets under moist conditions (Silverman H G, Roberto F F. *Mar Biotechnol* (NY) 2007, 9, 661-81. Deacon M P, Davis S S, Waite J H, Harding S E. *Biochemistry* 1998, 37, 14108-12). Cross-linking of the mussel glue is initiated by the enzymatic conversion of phenolic (i.e., dopa) residues of the adhesive protein into reactive quinone residues that can undergo subsequent inter-protein crosslinking reactions (Burzio L A, Waite J H. *Biochemistry* 2000, 39, 11147-53. McDowell L M, Burzio L A, Waite J H, Schaefer J J. *Biol Chem* 1999, 274, 20293-5). A second biological cross-linking operation that has served as a technological model is the transglutaminase-catalyzed reactions that occur during blood coagulation (Ehrbar M, Rizzi S C, Hlushchuk R, Djonov V, Zisch A H, Hubbell J A, Weber F E, Lutolf M P. *Biomaterials* 2007, 28, 3856-66). Biomimetic approaches for in situ gel formation have investigated the use of Factor XIIIa or other tissue transglutaminases (Sperinde J, Griffith L. *Macromolecules* 2000, 33, 5476-5480. Sanborn T J, Messersmith P B, Barron A E. *Biomaterials* 2002, 23, 2703-10).

One biomimetic approach for in situ gel formation of particular interest is the crosslinking of gelatin by a calcium independent microbial transglutaminase (mTG). mTG catalyzes an analogous crosslinking reaction as Factor XIIIa but the microbial enzyme requires neither thrombin nor calcium for activity. Initial studies with mTG were targeted to applications in the food industry (Babin H, Dickinson E. *Food Hydrocolloids* 2001, 15, 271-276. Motoki M, Seguro K. *Trends in Food Science & Technology* 1998, 9, 204-210), while later studies considered potential medical applications. Previous in vitro studies have shown that mTG can crosslink gelatin to form a gel within minutes, the gelatin-mTG adhesive can bond with moist or wet tissue, and the adhesive strength is comparable to, or better than, fibrin-based sealants (Chen T H, Payne G F, et al. *Biomaterials* 2003, 24, 2831-2841. McDermott M K, Payne G F, et al. *Biomacromolecules* 2004, 5, 1270-1279. Chen T, Payne G F, et al. *J Biomed Mater Res B Appl Biomater* 2006, 77, 416-22).

SUMMARY OF THE INVENTION

The background art does not teach or suggest an improved composition which features one or more additional excipients for controlling one or more properties of a non-fibrin protein or polypeptide based enzymatic cross-linked material, which could be used for a wide variety of applications, such as for hemostatic or body fluid sealing purposes, including but not limited to surgical applications, control of hemorrhage, sealing of fluid leakage, control of bleeding from a wound.

The present invention provides a composition comprising a cross-linkable protein or polypeptide and one or more cross-linking materials according to at least some embodiments.

According to some embodiments of the present invention, there is provided a composition comprising a cross-linkable protein or polypeptide, with the proviso that said protein or polypeptide is not fibrin, an enzyme which induces cross-linking of said cross-linkable protein, in a combined acetate and citrate buffer. Optionally, said cross-linkable protein or polypeptide is present in a sodium acetate buffer and wherein said enzyme is in a sodium citrate buffer before said cross-linkable protein or polypeptide and said enzyme are mixed, with their respective buffers, to form the composition. Preferably, said cross-linkable protein or polypeptide comprises gelatin. More preferably, said gelatin is at least 250 bloom.

According to some embodiments of the present invention, there is provided a composition further comprising calcium as any pharmaceutically compatible salt. And optionally further comprising urea.

Preferably a reduced amount of each of calcium and of urea is present when said calcium and said urea are present in combination than when each of calcium or urea is present separately.

More preferably said acetate and/or said citrate is less than about 0.5 M.

Optionally and most preferably said acetate and/or said citrate is at least about 0.01 M.

Optionally an ionic strength is selected from about 0.1 M to about 0.5 M according to a desired cross-linking time, wherein an increased ionic strength leads to a relatively decreased cross-linking time.

Optionally and preferably, for any composition described herein, the enzyme comprises one or more of transglutaminase or a multi-copper oxidase.

More preferably said transglutaminase comprises microbial transglutaminase.

According to some embodiments of the present invention, there is provided a composition comprising a cross-linkable protein or polypeptide, with the proviso that said protein or polypeptide is not fibrin, an enzyme which induces cross-linking of said cross-linkable protein, a metal ion and a denaturing agent.

Optionally the cross-linkable protein or polypeptide comprises gelatin. Preferably, said gelatin is at least 250 bloom.

More preferably said metal ion comprises calcium as any pharmaceutically compatible salt. Most preferably, said calcium salt comprises one or more of calcium chloride or calcium hydroxide. Optionally and most preferably, said calcium is present in an amount of up to 1M.

Optionally for any composition described herein said denaturing agent comprises a chaotrope. Preferably, said chaotrope comprises urea. More preferably, said urea is present in an amount of up to 4M. Most preferably, a reduced amount of each of calcium and of urea is present when said calcium and said urea are present in combination.

Optionally the composition further comprises a calcium sequestering agent when said metal ion comprises calcium.

According to some embodiments of the present invention, there is provided a composition comprising a cross-linkable protein or polypeptide, with the proviso that said protein or polypeptide is not fibrin, a calcium independent enzyme which induces cross-linking of said cross-linkable protein, and a calcium sequestering agent.

Optionally said calcium sequestering agent comprises one or more of EDTA, citrate or calgon. Preferably, said citrate or said EDTA is present in an amount of from about 0.01 M to about 2M. More preferably, said citrate or said EDTA is present in an amount from about 0.05M to about 0.2M. Most preferably, said citrate or said EDTA is present in an amount from about 0.5M to about 2M.

According to some embodiments of the present invention, there is provided a composition comprising a cross-linkable protein or polypeptide, with the proviso that said protein or polypeptide is not fibrin, an enzyme which induces cross-linking of said cross-linkable protein, and a viscosity increasing agent selected from the group consisting of Alginate Ester, Gum Arabic, high viscosity Carboxymethyl cellulose (CMC), Xanthan Gum, Guar Gum, and PVP.

According to some embodiments of the present invention, there is provided a composition comprising a cross-linkable protein or polypeptide, with the proviso that said protein or polypeptide is not fibrin, an enzyme which induces cross-linking of said cross-linkable protein, and a kosmotrope.

Optionally said kosmotrope is selected from the group consisting of proline, trehalose and glutamate or a combination of any two or more thereof. Also optionally the composition further features a chaotrope.

According to some embodiments of the present invention, there is provided a composition comprising gelatin, transglutaminase and a PEG (polyethylene glycol) derivative capable of covalently binding to said gelatin. Optionally said PEG derivative comprises any aminated PEG derivative. Preferably, said aminated PEG derivative comprises PEG amine.

According to some embodiments of the present invention, there is provided a composition comprising gelatin, transglutaminase and a PVA (polyvinyl alcohol) derivative capable of covalently binding to said gelatin. Optionally, said PVA derivative comprises any aminated PVA derivative. Preferably, said aminated PVA derivative comprises PVA amine.

According to some embodiments of the present invention, there is provided a composition comprising gelatin, an amine substrate cross-linker and an inhibitor of carbamylation. Optionally, said cross-linker comprises transglutaminase.

Preferably said inhibitor of carbamylation comprises an amine donor. More preferably, said amine donor is selected from the group consisting of glycine and histidine. Optionally and more preferably, said amine donor is present in an amount that does not inhibit cross-linking of said gelatin by said cross-linker. Also optionally and more preferably, said amine donor is present in an amount to partially inhibit cross-linking of said gelatin by said cross-linker. The above compositions may also optionally further comprise urea.

According to some embodiments of the present invention, there is provided a composition comprising at least partially succinylated gelatin, non-succinylated gelatin and an amine substrate cross-linker.

According to some embodiments of the present invention, there is provided a composition comprising at least partially carbamylated gelatin, non-carbamylated gelatin and an amine substrate cross-linker.

According to some embodiments of the present invention, there is provided a composition comprising gelatin, a diamine and an amine substrate cross-linker. Optionally, said diamine comprises putrescine.

According to some embodiments of the present invention, there is provided a composition comprising gelatin, an amine donor and an amine substrate cross-linker.

Optionally said amine donor comprises polyethylenimine (PEI). Preferably, the amine substrate cross-linker comprises transglutaminase.

According to some embodiments of the present invention, there is provided a cross-linked composition, comprising a foamed gelatin and transglutaminase. Optionally, said transglutaminase is present in a lyophilized form.

According to some embodiments of the present invention, there is provided a composition comprising a cross-linkable protein or polypeptide, with the proviso that said protein or polypeptide is not fibrin, a calcium independent enzyme which induces cross-linking of said cross-linkable protein, a denaturing agent and an agent for reversing an effect of said denaturing agent, for reversing sol gel transition point lowering effect of the denaturing agent.

Optionally said denaturing agent comprises urea and said agent for reversing said effect of said denaturing agent comprises urease.

Optionally any composition as described herein may further comprise sorbitol. Optionally and preferably, said sorbitol is present in a sufficient amount to increase the cross-linked composition's flexibility and/or to accelerate the rate of cross-linking. The composition may also optionally further comprise acetate.

According to some embodiments of the present invention, any of the compositions herein may optionally further comprise a plasticizer. Optionally, said plasticizer is selected from the group consisting of Gum Arabic, Guar Gum, PVA, PEG 6000, Polyvinylpyrrolidone (PVP), citric acid alkyl esters, glycerol esters, phthalic acid alkyl esters, sebacic acid alkyl esters, sucrose esters, sorbitan esters, acetylated monoglycerides, glycerols, fatty acid esters, glycols, propylene glycol, lauric acid, sucrose, glyceryl triacetate, poloxamers, diethyl phthalate, mono- and di-glycerides of edible fats or oils, dibutyl phthalate, dibutyl sebacate, polysorbate, polyethylene glycols 200 to 12,000, Carbowax polyethylene glycols, and a surfactant at a concentration above the CMC (critical micelle concentration) of said surfactant; or a combination thereof. Preferably, said surfactant comprises a polyoxyethylene-sorbitan-fatty acid ester, polyoxyethyleneglycol dodecyl ether, polyoxyethylene-polyoxypropylene block copolymer, sodium lauryl sulfate, sodium dodecyl sulfate, sodium laureth sulfate, sodium lauryl ether sulfate, poloxamers, poloxamines, alkyl polyglucosides, fatty alcohols, fatty acid salts, cocamide monoethanolamine, and cocamide diethanolamine.

More preferably, a concentration of said surfactant is in the range of from about 0.1% to about 5% w/w of dry weight of said cross-linkable protein. Optionally and most preferably, said polyoxyethylene-sorbitan-fatty acid ester comprises one or more of polysorbates 20, 21, 0, 60, 61, 65, 80 or 85.

According to some embodiments of the present invention, any of the compositions herein may optionally further comprise a viscosity increasing agent selected from the group consisting of Alginate Ester, Gum Arabic, high viscosity Carboxymethyl cellulose (CMC), Xanthan Gum, Guar Gum, and PVP.

According to some embodiments of the present invention, for any of the compositions herein, optionally said enzyme comprises transglutaminase, the composition further comprising one or more of Cystamine, Cysteine, cyanate or Melanin.

According to some embodiments of the present invention, any of the compositions herein may optionally further comprise an ammonia scavenging, sequestering or binding agent, a stimulator of ammonia metabolism, or an inhibitor of cellular ammonia uptake. Optionally, said ammonia scavenging agent comprises disaccharide lactulose. Also optionally, said ammonia-binding agent comprises a saponin. Preferably, said ammonia scavenger comprises a solution comprising sodium phenylacetate and sodium benzoate.

Also preferably, said stimulator of ammonia metabolism comprises L-glutamine, L-glutamate, or a combination thereof.

Also preferably, said inhibitor of cellular ammonia uptake comprises L-glutamine, L-glutamate, or a combination thereof.

According to some embodiments of the present invention, any of the compositions herein may optionally further comprise a buffer selected from the group consisting of succinate buffer, maleate buffer, tris(hydroxymethyl)methylamine (TRIS), 3-{[tris(hydroxymethyl)methyl] amino}propanesulfonic acid (TAPS), N,N-bis(2-hydroxyethyl)glycine (bicine), N-tris(hydroxymethyl)methylglycine (tricine), 2-{[tris(hydroxymethyl)methyl] amino}ethanesulfonic acid (TES), 3-(N-morpholino)propanesulfonic acid (MOPS), piperazine-N,N'-bis(2-ethanesulfonic acid) (PIPES), dimethylarsinic acid, N-(2-hydroxyethyl)piperazine-N'-(2-ethane sulfonic acid) (HEPES), and 2-(N-morpholino)ethanesulfonic acid (MES).

According to some embodiments of the present invention, any of the compositions herein may optionally have a pH in a range of from about 6 to about 7, which is also optionally about 6.

According to some embodiments of the present invention, for any of the compositions herein may optionally, said enzyme comprises transglutaminase. Optionally, said transglutaminase is calcium independent. Preferably, said transglutaminase is microbial transglutaminase. More preferably, a protein concentration of said transglutaminase is present in an amount from about 0.0001% to about 2% w/w of the composition. Most preferably, said transglutaminase is present in an amount of from about 0.01% to about 1.35% w/w of the composition. Also most preferably, said transglutaminase is present in an amount of from about 0.05% to about 0.5% w/w of the composition.

Optionally and most preferably said transglutaminase is present in an amount of from about 0.1% to about 0.4% w/w of the composition.

Optionally said concentration of transglutaminase is in the range of from about 1 to about 180 enzyme units (U/mL) of total composition. Preferably said concentration of transglutaminase is in the range of from about 4 to about 70 enzyme units (U/mL) of total composition. More preferably, said concentration of transglutaminase is in the range of from about 10 to about 55 enzyme units (U/mL) of total composition.

Optionally for any of the compositions herein a ratio of cross linking material:cross linkable protein solution is about 1:1 to 1:5 v/v.

According to some embodiments of the present invention, for any of the compositions herein, said cross-linkable protein or polypeptide comprises gelatin and wherein said gelatin is produced from animal origin, recombinant origin or a combination thereof. Optionally said animal origin is selected from the group consisting of fish and mammals. Preferably, said mammal is selected from the group consisting of pigs and cows. More preferably, said gelatin is of type A (Acid Treated) or of type B (Alkaline Treated). Most preferably, said gelatin comprises high molecular weight gelatin. Optionally and most preferably, said gelatin is at least about 250 bloom. Also optionally and most preferably, said gelatin is produced during the first extraction.

According to some embodiments of the present invention, any of the compositions herein may optionally further comprise a method for manufacturing a composition for cross-linking, comprising: preparing a solution of a cross-linkable protein or polypeptide, with the proviso that said protein or polypeptide is not fibrin, an enzyme for cross-linking said cross-linkable protein or polypeptide, and a pharmaceutically acceptable calcium salt; and adding a calcium sequestering agent to said solution.

Optionally said calcium sequestering agent comprises one or more of a polyphosphate salt, and a carboxylate, or combinations thereof. Also optionally, said polyphosphate salt is selected from the group consisting of a pyrophosphate, a tripolyphosphate, a higher polyphosphate salt, and a hexametaphosphate salt, or combinations thereof. Preferably, the pyrophosphate is selected from the group consisting of tetrasodium pyrophosphate, disodium dihydrogen pyrophosphate, tetrapotassium pyrophosphate, dipotassium dihydrogen pyrophosphate, and dipotassium disodium pyrophosphate, or combinations thereof. Also preferably, said tripolyphosphate is selected from the group consisting of pentasodium tripolyphosphate, and pentapotassium tripolyphosphate, or combinations thereof.

Also preferably, said carboxylate is selected from the group consisting of an alkali metal citrate salt, an alkali metal acetate salt, an alkali metal lactate salt, an alkali metal tartrate salt, an alkali metal malate salt, an alkali metal salt of ethylenediaminetetraacetic acid, and editronic acid, or combinations thereof. More preferably, said carboxylate is selected from the group consisting of ethylenediaminetetraacetic acid and sodium citrate, or a combination thereof.

Optionally and more preferably, said hexametaphosphate comprises sodium hexametaphosphate.

According to some embodiments of the present invention, there is provided a method for manufacturing a composition for cross-linking, comprising: preparing a solution of a cross-linkable protein or polypeptide, with the proviso that said protein or polypeptide is not fibrin, an enzyme for cross-linking said cross-linkable protein or polypeptide, and a denaturant; and adding an agent for reversing an effect of said denaturing agent, for reversing sol gel transition point lowering effect of the denaturing agent, to said solution.

Optionally said denaturing agent comprises urea and said agent for reversing said effect of said denaturing agent comprises urease.

According to some embodiments of the present invention, there is provided a method for manufacturing a composition for cross-linking, comprising: preparing a solution of a cross-linkable protein or polypeptide, with the proviso that said protein or polypeptide is not fibrin, an enzyme for cross-linking said cross-linkable protein or polypeptide, and a chaotrope; and adding a kosmotrope to said solution.

Optionally, wherein said kosmotrope is selected from the group consisting of proline, trehalose and glutamate or a combination of any two or more thereof.

According to some embodiments of the present invention, there is provided a method for manufacturing a composition for cross-linking, comprising: preparing a solution of a cross-linkable protein or polypeptide, with the proviso that said protein or polypeptide is not fibrin, and transglutaminase for cross-linking said cross-linkable protein or polypeptide; and adding one or more of Cystamine, Cysteine, cyanate or Melanin to said solution for at least partial inhibition of said transglutaminase.

According to some embodiments of the present invention, there is provided a microbial transglutaminase composition with specific activity >25 enzyme units per milligram, >95% electrophoretic purity, <5 endotoxin units per gram, and <10 CFU/g. Such a transglutaminase may optionally be provided as the cross-linker of any of the above claims.

According to some embodiments of the present invention, the composition features a buffer and one or more other excipients, which are selected to overcome at least some of the drawbacks of the background art.

Optionally and preferably, the buffer is a non-phosphate buffer, which is optionally and more preferably selected from the group consisting of an acetate buffer (such as sodium acetate), citrate buffer (such as sodium citrate), succinate buffer, maleate buffer, tris(hydroxymethyl)methylamine (TRIS), 3-{[tris(hydroxymethyl)methyl]amino}propanesulfonic acid (TAPS), N,N-bis(2-hydroxyethyl)glycine (bicine), N-tris(hydroxymethyl)methylglycine (tricine), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid, N-(2-hydroxyethyl)piperazine-N'-(2-ethane sulfonic acid) (HEPES), and 2-(N-morpholino)ethanesulfonic acid (MES).

According to some embodiments, the composition is used as a vehicle for localized drug delivery.

According to some embodiments, the composition is an injectable scaffold for tissue engineering.

According to some embodiments, the composition is a hemostatic composition. According to some embodiments, the composition is a body fluid sealing composition.

The compositions of the present invention preferably provide rapid hemostasis, thereby minimizing blood loss following injury or surgery.

"Wound" as used herein refers to any damage to any tissue of a patient that results in the loss of blood from the circulatory system or the loss of any other bodily fluid from its physiological pathway, such as any type of vessel. The tissue can be an internal tissue, such as an organ or blood vessel, or an external tissue, such as the skin. The loss of blood or bodily fluid can be internal, such as from a ruptured organ, or external, such as from a laceration. A wound can be in a soft tissue, such as an organ, or in hard tissue, such as bone. The damage may have been caused by any agent or source, including traumatic injury, infection or surgical intervention. The damage can be life-threatening or non-life-threatening.

"TG" refers to transglutaminase of any type; "mTG" may also refer to microbial transglutaminase and/or to any type of transglutaminase, depending upon the context (in the specific experimental Examples below, the term refers to microbial transglutaminase). Optionally, the transglutaminase comprises a plant, recombinant animal, or microbe derived transglutaminase other than blood derived Factor XIII; however, the actual production process for the transglutaminase may optionally comprise any type of recombinant method as is known in the art.

Surgical wound closure is currently achieved by sutures and staples that facilitate healing by pulling tissues together. However, very often they fail to produce the adequate seal necessary to prevent fluid leakage. Thus, there is a large, unmet medical need for devices and methods to prevent leakage following surgery, including leaks that frequently occur along staple and suture lines. Such devices and methods are needed as an adjunct to sutures or staples to achieve hemostasis or other fluid-stasis in peripheral vascular reconstructions, dura reconstructions, thoracic, cardiovascular, lung, neurological, and gastrointestinal surgeries. Most high-pressure hemostatic devices currently on the market are nominally, if at all adhesive. Good examples of such devices are the QuikClot® ACS™ (Z-Medica, Wallington, Conn.) and HemCon™ bandage (HemCon, Portland, Oreg.), the two hemostatic devices currently supplied to members of the US armed forces. The chitosan network that makes up the HemCon bandage can be saturated with blood and fail quickly when faced with brisk flood flow or after 1-2 hours when confronted with moderate blood flow from a wound (B. S Kheirabadi et al. (2005). J. Trauma. 59:25-35; A. E. Pusateri et al. (2006). J. Trauma. 60:674-682). The QuikClot minerals must cause a dangerous amount of heat in order to be effective (A. E. Pusateri et al. (2006). J. Trauma. 60:674-682).

Other polysaccharide-based hemostatic devices that have been suggested for use in hemorrhage control are RDH™ (Acetyl Glucosamine), TraumaDEX™ (MPH), and Chitoskin™ (Chitosan & Gelatin). However, none of these types of bandages have been able to consistently demonstrate avoidance of failure in the face of significant blood flow. Other recently introduced hemostatic devices include Celox™ (Chitosan Crystals) and WoundStat™ (TraumaCure Inc., MD) (granular blend of smectite mineral and a super absorbent polymer). However, both of these products rapidly swell to fill wound sites, making them appropriate only for accelerating blood clotting in specific types of wounds and presenting a danger of reducing or even eliminating blood flow in surrounding blood vessels.

All of the above-mentioned products rely on the natural clotting cascade to control fluid leakage from a wound site. As such, they are significantly limited in their capacity. General wound site sealing, particularly of injured sites leaking non-blood fluids, is beyond the scope of these products.

With regard to previous efforts to form a tissue adhesive from the crosslinking of gelatin with mTG (ie McDermott et al 2004 and Chen et al. 2006), the commercial application of these efforts have been limited due to the thermoreversible gelation that takes place in gelatin solutions at operating room temperatures. Though urea has been proposed in the past for lowering the gelation transition point of gelatin solutions for use in adhesives (Otani et al. 1998), this was not previously considered for use with gelatin-mTG sealants since urea has been established as a strong denaturant that can significantly disrupt enzyme activity (Rajagopalan et al. *J Biologica Chem* 236(4), 1961). Furthermore, in studies that specifically explored mTG activity in the presence of urea, it was found that very low concentrations of urea (<0.5M) severely inhibit mTG function (Nomura Y et al. *Biosci Biotech Biochem* 65(4), 2001: p. 982-985) and high concentrations of urea (8M) completely inactivate mTG (Yokoyama K et al. *Protein Exp & Purif* 26, 2002: p. 329-335 2002).

Surprisingly, the present inventors found that urea could in fact be successfully used with gelatin and mTG under certain circumstances, as described in PCT Pub. No. WO/2008/076407, filed on Dec. 17, 2007, by the present inventors, hereby incorporated by reference as if fully set forth herein. Further surprisingly, the present inventors have expanded the potential use and inclusion of urea in a crosslinked gelatin/mTG composition as described in greater detail below.

As used herein, "about" means plus or minus approximately ten percent of the indicated value.

Other features and advantages of the various embodiments of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
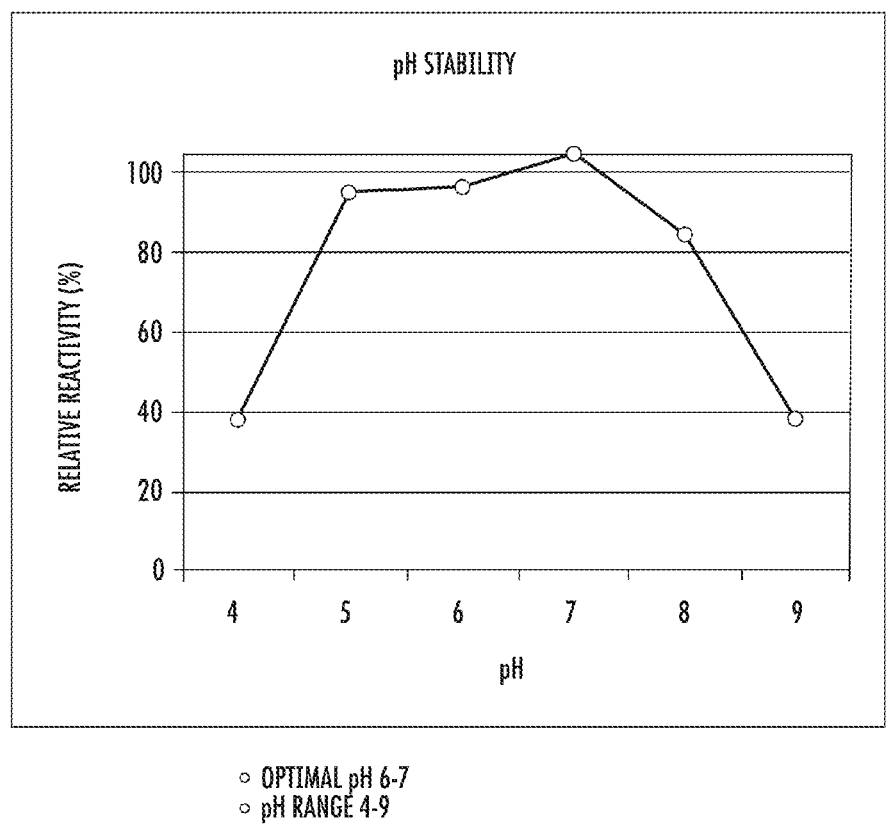
FIG. 1 is a graph showing pH stability of mTG.

The present invention is of improved compositions comprising a solution of a cross-linkable protein or polypeptide, and a solution of one or more non-toxic materials which induces cross-linking of the cross-linkable protein.

According to some embodiments, the solution of a cross-linkable protein or polypeptide, and a solution of one or more non-toxic materials which induces cross-linking of the cross-linkable protein are prepared in a non-phosphate buffer solvent.

Optionally and preferably, the cross-linkable protein includes gelatin and any gelatin variant or variant protein as described herein. Optionally and preferably, the non-toxic material comprises transglutaminase (TG), which may optionally comprise any type of calcium dependent or independent transglutaminase, which may for example optionally be a calcium-independent microbial transglutaminase (mTG). Without wishing to be limited in any way, among the improved properties of at least some embodiments of the present invention, the compositions of the present invention provide an increased rate of protein cross-linking as compared to background art compositions. Furthermore, the crosslinking reaction of mTG represents a significant improvement over that catalyzed by Factor XIIIa of the blood coagulation system. Unlike Factor XIIIa, the microbial enzyme requires neither thrombin nor calcium for activity.

The present invention therefore, in at least some embodiments, provides an improved application of a gelatin-mTG adhesive composition for a variety of soft tissue applications. The present invention further provides, in some embodiments, a method for preparing a composition, the method comprising providing a solution of a cross-linkable protein or polypeptide; providing a solution of one or more cross-linking materials; and mixing the solution of the cross-linkable protein or polypeptide with the solution of cross-linking materials.

According to some embodiments of the present invention, the composition is provided in a bandage, which is preferably adapted for use as a hemostatic bandage. The herein described compositions may additionally have one or uses including but not limited to tissue adhesives (particularly biomimetic tissue adhesives), tissue culture scaffolds, tissue sealants, hemostatic compositions, drug delivery platforms, surgical aids, or the like, as well as other non-medical uses, including but not limited to edible products, cosmetics and the like, such as, for example, in purification of enzymes for use in food products.

Various embodiments of the present invention are described in greater detail below, under section headings which are provided for the sake of clarity only and without any intention of being limiting in any way.

Cross-Linkable Protein

According to a preferred embodiment of the present invention, the cross-linkable protein comprises gelatin.

Gelatin may optionally comprise any type of gelatin which comprises protein that is known in the art, preferably including but not limited to gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture.

According to preferred embodiments of the present invention, gelatin from animal origins preferably comprises gelatin from mammalian origins and more preferably comprises one or more of pork skins, pork and cattle bones, or split cattle hides, or any other pig or bovine source. More preferably, such gelatin comprises porcine gelatin since it has a lower rate of anaphylaxis. Gelatin from animal origins may optionally be of type A (Acid Treated) or of type B (Alkaline Treated), though it is preferably type A (however an example using type B gelatin is given below).

Preferably, gelatin from animal origins comprises gelatin obtained during the first extraction, which is generally performed at lower temperatures (50-60° C., although this exact temperature range is not necessarily a limitation). Gelatin produced in this manner will be in the range of 250-300 bloom and has a high molecular weight of at least about 95-100 kDa. Preferably, 275-300 bloom gelatin is used.

A non-limiting example of a producer of such gelatins is PB Gelatins (Tessenderlo Group, Belgium).

According to some embodiments of the present invention, gelatin from animal origins optionally comprises gelatin from fish. Optionally any type of fish may be used, preferably a cold water variety of fish such as carp, cod, or pike, or tuna. The pH of this gelatin (measured in a 10% solution) preferably ranges from 4-6.

Cold water fish gelatin forms a solution in water at 10° C. and thus all cold water fish gelatin are considered to be 0 bloom. For the present invention, a high molecular weight cold water fish gelatin is optionally and preferably used, more preferably including a molecular weight of at least about 95-100 kDa. This is equivalent to the molecular weight of a 250-300 bloom animal gelatin. Cold water fish gelatin undergoes thermoreversible gelation at much lower temperatures than animal gelatin as a result of its lower levels of proline and hydroxyproline. Per 1000 amino acid residues, cold water fish gelatin has 100-130 proline and 50-75 hydroxyproline groups as compared to 135-145 proline and 90-100 hydroxyproline in animal gelatins (Haug I J, Draget K I, Smidsrød O. (2004). Food Hydrocolloids. 18:203-213).

A non-limiting example of a producer of such a gelatin is Norland Products (Cranbury, N.J.).

In some embodiments of the present invention, low endotoxicity gelatin is used to form the gelatin solution component of the gelatin-mTG composition. Such a gelatin is available commercially from suppliers such as Gelita™ (Eberbach, Germany). Low endotoxicity gelatin is defined as gelatin with less than 1000 endotoxicity units (EU) per gram. More preferably, gelatin of endotoxicity less than 500 EU/gram is used.

For very high sensitivity applications, such as with materials that will come into contact with either the spine or the brain, gelatin with endotoxicity of less than 100 EU/gram is preferred, gelatin with less than 50 EU/g is more preferred. Gelatin with endotoxicity less than 10 EU/g is very expensive but could also be used as part of at least some embodiments of the present invention in sensitive applications.

According to some embodiments of the present invention, type I, type II, or any other type of hydrolyzed or non-hydrolyzed collagen replaces gelatin as the protein matter being cross-linked. Various types of collagen have demonstrated the ability to form thermally stable mTG-crosslinked gels (O'Halloran D M, et al. Characterization of a microbial transglutaminase cross-linked type II collagen scaffold. *Tissue Eng.* 2006 June; 12(6):1467-74. Garcia Y, et al. Assessment of cell viability in a three-dimensional enzymatically cross-linked collagen scaffold. *J Mater Sci Mater Med.* 2007 October; 18(10):1991-2001. Epub 2007 Jun 7. Nomura Y, et al. Improvement of shark type I collagen with microbial transglutaminase in urea. *Biosci Biotechnol Biochem.* 2001 April; 65(4):982-5.)

According to some embodiments of the present invention, a recombinant human gelatin is used. Such a gelatin is available commercially from suppliers such as Fibrogen™ (San Francisco, Calif.). Recombinant gelatin is preferably at least about 90% pure and is more preferably at least about 95% pure. Some recombinant gelatins are non-gelling at 10° C. and thus are considered to be 0 bloom. For some embodiments of the present invention, a high molecular weight recombinant gelatin is preferably used, more preferably including a molecular weight of at least about 95-100 kDa.

As noted above, the cross-linkable protein preferably comprises gelatin but may also, additionally or alternatively, comprise another type of protein. According to some embodiments of the present invention, the protein is also a substrate for transglutaminase, and preferably features appropriate transglutaminase-specific polypeptide and polymer sequences. These proteins may optionally include but are not limited to synthesized polymer sequences that independently have the properties to form a bioadhesive or polymers that have been more preferably modified with transglutaminase-specific substrates that enhance the ability of the material to be cross-linked by transglutaminase. Non-limiting examples of each of these types of materials are described below.

Synthesized polypeptide and polymer sequences with an appropriate transglutaminase target for cross-linking have been developed that have transition points preferably from about 20 to about 40° C. Preferred physical characteristics include but are not limited to the ability to bind tissue and the ability to form fibers. Like gelling type gelatins (described above), these polypeptides may optionally be used in compositions that also feature one or more substances that lower their transition point.

Non-limiting examples of such peptides are described in U.S. Pat. Nos. 5,428,014 and 5,939,385, both filed by Zymo-Genetics Inc, both of which are hereby incorporated by reference as if fully set forth herein. Both patents describe biocompatible, bioadhesive, transglutaminase cross-linkable polypeptides wherein transglutaminase is known to catalyze an acyl-transfer reaction between the γ-carboxamide group of protein-bound glutaminyl residues and the ε-amino group of Lys residues, resulting in the formation of ε-(γ-glutamyl) lysine isopeptide bonds.

For example, polypeptides having 13-120 amino acid residues are described, comprising a segment of the formula S1-Y-S2, wherein: S1 is Thr-Ile-Gly-Glu-Gly-Gln; Y is a spacer peptide of 1-7 amino acids or not present; and S2 is Xaa-Lys-Xaa-Ala-Gly-Asp-Val. Optionally, the spacer peptide Y is Gln-His-His-Leu-Gly, Gln-His-His-Leu-Gly-Gly or His-His-Leu-Gly-Gly. Also optionally, Xaa, amino acid 1, of S2 is Ala or Ser. Optionally, the spacer peptide comprises His-His-Leu-Gly. Optionally and preferably, at least one of Y and S2 are free of Gln residues. Optionally, the carboxyl terminal amino acid residue of the polypeptide is Pro or Gly. Specific non-limiting examples of the polypeptides include the following: Thr-Ile-Gly-Glu-Gly-Gln-Gln-His-His-Leu-Gly-Gly-Ala-Lys-Gln-Ala-Gly-Asp-Val, Thr-Ile-Gly-Glu-Gly-Gln-Gln-His-His-Leu-Gly-Ala-Lys-Gln-Ala-Gly-Asp-Val, Thr-Ile-Gly-Glu-Gly-Gln-His-His-Leu-Gly-Gly-Ala-Lys-Gln-Ala-Gly-Asp-Val, or Leu-Ser-Gln-Ser-Lys-Val-Gly. The patent also describes high molecular weight, biocompatible, bioadhesive, transglutaminase-cross-linkable copolymers and homopolymers involving these peptides.

U.S. Pat. No. 5,939,385 describes biocompatible, bioadhesive transglutaminase cross-linkable polypeptides. These polypeptides preferably have about 9-120 amino acid residues comprising a segment of the formula S1-Y-S2, wherein: S1 is selected from the group consisting of Ile-Gly-Glu-Gly-Gln, Gly-Glu-Gly-Gln, Glu-Gly-Gln, and Gly-Gln; Y is His-His-Leu-Gly-Gly or His-His-Leu-Gly; and S2 is selected from the group consisting of Ala-Lys-Gln-Ala-Gly-Asp, Ala-Lys-Gln-Ala-Gly, Ala-Lys-Gln-Ala, Ala-Lys-Gln, Ala-Lys-Ala-Gly-Asp-Val, Ala-Lys-Ala and Ala-Lys, wherein said polypeptide has an amino-terminus and a carboxy-terminus and is cross-linkable by a transglutaminase. A preferred polypeptide is Gly-Gln-His-His-Leu-Gly-Gly-Ala-Lys-Gln. Also preferred is a polypeptide wherein the polypeptide is flanked on either or both the amino-terminus and the carboxy-terminus by an elastomeric polypeptide. It further provides an elastomeric polypeptide wherein the elastomeric polypeptide is a pentapeptide or a tetrapeptide, particularly a flanked polypeptide wherein the flanking elastomeric polypeptide is Val-Pro-Gly-Val-Gly, Ala-Pro-Gly-Val-Gly, Gly-Val-Gly-Val-Pro, Val-Pro-Gly-Gly or any portion thereof, preferably such that the amino-terminus of the flanked polypeptide is Val and the carboxy-terminus of the flanked polypeptide is Gly. The patent also describes high molecular weight, biocompatible, bioadhesive, transglutaminase-cross-linkable copolymers and homopolymers involving these peptides.

Cross-Linking Material

Optionally and preferably, the non-toxic cross-linking material comprises transglutaminase (TG), which may optionally comprise any type of calcium dependent or independent transglutaminase (mTG), which may for example optionally be a microbial transglutaminase.

According to some embodiments of the present invention, newly available commercial transglutaminase products containing 10% or more mTG may be used. Non-limiting examples of commercially available transglutaminase products of this sort include those produced by Ajinomoto Co. (Kawasaki, Japan) and Yiming Chemicals (China). A non-limiting example of such a product from this company is Activa TG—Ingredients: mTG (10%) and maltodextrin (90%); Activity: 810-1,350 U/g of Activa. Non-limiting examples of such products from Yiming include one product containing 10% mTG and 90% maltodextran and one product containing 10% mTG and 90% lactose, also of activity 810-1,350 U/g of product. Other non-limiting examples of such products from Yiming include one product containing 30% mTG and 70% maltodextran and one product containing 30% mTG and 70% lactose, both with activity 2,430-4,050 U/g of product.

As noted above, the cross-linking material preferably comprises transglutaminase but may also, additionally, comprise another type of cross-linking material according to some embodiments of the present invention.

Non-limiting examples of such cross-linking agents include carbodiimides such as N,N-(3-(dimethylamino)propyl)-N-ethyl carbodiimide (EDC), N-hydroxysuccinimide (NHS) with EDC, or carbodiimides used together with poly (L-glutamic acid) (PLGA) and polyacrylic acid. In another embodiment, such cross-linking agents can include Tyrosinase or Tyrosinase with chitosan. In another embodiment, cross-linking (polymerization) is photo-initiated with ultraviolet light or γ-rays. In another embodiment, cross-linking agents can include alkylene, citric acid (carbonic acid), or Nano-hydroxyapataite (n-HA)+poly(vinyl alcohol) (PVA).

In another embodiment, a cross-linking agent is a plant-derived polyphenol such as (i.e. hydroxylated cinnamic acids, such as caffeic acid (3,4-dihydroxycinnamic acid), chlorogenic acid (preferably the quinic acid ester), caftaric acid (preferably the tartaric acid ester), and flavonoids (i.e. as quercetin and rutin). In another embodiment, the additional cross-linking agent is an oxidized mono or disaccharide, oxo-lactose, or a dialdehyde based on a sugar moiety (galactohexodialdose) (GALA). In another embodiment, Genipin or other iridoid glycoside derivative, or Secoiridoids, preferable oleuropein, comprises the cross-linking agent. In another embodiment, the cross-linking agent is a thiol-reactive poly (ethylene glycol). In another embodiment, the cross-linking agent is dextran, oxidized dextran, dextran dialdehyde. In another embodiment, the cross-linking agent is a multi-copper oxidase such as laccase or bilirubin oxidase.

Illustrative Compositions

The above described cross-linking substrates and cross-linking materials may optionally be combined with one or more additional materials to form various compositions according to the present invention. According to some embodiments, the adhesive material optionally and preferably comprises: (i) gelatin; (ii) a transglutaminase. More preferably, the gelatin and transglutaminase are provided in sufficient quantities to be useful as a sealing, hemostatic agent.

In addition, one or more supplements can also be contained in the hemostatic product, e.g., drugs such as growth factors, polyclonal and monoclonal antibodies and other compounds. Illustrative examples of such supplements include, but are not limited to: antibiotics, such as tetracycline and ciprofloxacin, amoxicillin, and metronidazole; anticoagulants, such as activated protein C, heparin, prostracyclin ($PGI_2$), prostaglandins, leukotrienes, antitransglutaminase III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; chemoattractants; local anesthetics such as bupivacaine; and antiproliferative/antitumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as alpha- or beta- or gamma-Interferon, alpha- or beta-tumor necrosis factor, and interleukins; colony stimulating factors; erythropoietin; antifungals, such as diflucan, ketaconizole and nystatin; antiparasitic agents, such as pentamidine; anti-inflammatory agents, such as alpha-1-anti-trypsin and alpha-1-antichymotrypsin; anesthetics, such as bupivacaine; analgesics; antiseptics; and hormones. Other illustrative supplements include, but are not limited to: vitamins and other nutritional supplements; glycoproteins; fibronectin; peptides and proteins; carbohydrates (both simple and/or complex); proteoglycans; antiangiogenins; antigens; lipids or liposomes; and oligonucleotides (sense and/or antisense DNA and/or RNA).

Buffer Selection

PCT Pub. No. WO/2008/076407, filed on Dec. 17, 2007, discloses compositions comprising gelatin as a cross-linkable protein, and microbial transglutaminase as a non-toxic cross-linking material, wherein Phosphate Buffered Saline (PBS) is used as a preferred solvent for dissolving both the gelatin and the mTG. However, PBS has been discovered to reduce the speed of mTG-facilitated gelatin cross-linking. Without wishing to be limited to a single hypothesis, it is suggested that the phosphate molecules in the buffer reduce the cross-linking activity of the mTG enzyme. Therefore, buffers which are devoid of phosphate have been determined to be more efficacious for use as buffers of both gelatin and mTG solutions.

Non-limiting examples of non-phosphate buffers suitable for use in the present invention include acetate buffer (such as sodium acetate), citrate buffer (such as sodium citrate), succinate buffer, maleate buffer, tris(hydroxymethyl)methylamine (TRIS), 3-{[tris(hydroxymethyl)methyl]amino}propanesulfonic acid (TAPS), N,N-bis(2-hydroxyethyl)glycine (bicine), N-tris(hydroxymethyl)methylglycine (tricine), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid, N-(2-hydroxyethyl)piperazine-N'-(2-ethane sulfonic acid) (HEPES), and 2-(N-morpholino)ethanesulfonic acid (MES).

Optionally and preferably, buffers comprising one or more carboxyl groups are used. More preferably, the buffer comprises sodium acetate or sodium citrate. More preferably, sodium acetate is used as a buffer for the protein or polypeptide, and sodium citrate or sodium acetate is used as buffer for the cross-linking material.

Optionally and preferably, the buffer solutions have a concentration in the range of from about 0.01 to about 0.6M. More preferably, the buffer solution for the protein or polypeptide has a concentration in the range of from about 0.05 to about 0.15M, and most preferably has a concentration of about 0.1M. More preferably, the buffer solution for the cross-linking material has a concentration in the range of from about 0.1 to about 0.5M. The benefit of these concentrations is described with regard to the below illustrative, non-limiting examples.

Without wishing to be limited by a single hypothesis, sodium acetate buffer is believed to accelerate the mTG-catalyzed crosslinking of the protein, as described with regard to the below illustrative, non-limiting examples.

Without wishing to be limited by a single hypothesis, sodium citrate buffer is believed to improve the mechanical and biocompatibility properties of the crosslinked composition if added to the protein/polypeptide solution together with the crosslinker. This effect is described more in detail below.

Surprisingly, it was found that by using sodium acetate buffer with the protein/polypeptide solution and sodium citrate buffer with the crosslinker solution in a single composition, the benefits of using each type of buffer (ie accelerated crosslinking and improved mechanical properties) could be simultaneously achieved, without any inappropriate inhibition of any reaction or any inappropriate additional reaction occurring. The successful implementation of this approach is described with regard to the below illustrative, non-limiting examples.

Buffer pH

PCT Pub. No. WO/2008/076407, filed on Dec. 17, 2007, further discloses that according to a preferred embodiment, the pH of the buffer is adjusted to a value in the range of from about 1.5 to about 5.0, or from about 7.0 to about 9.0, which is outside the general range of isoionic pH values for gelatins, in order to increase the solubility of gelatin in the solution. According to the teachings of the PCT application, the further the product pH is from the isoionic pH the better will be the solubility of the gelatin. As noted in greater detail below, it has been found that for transglutaminase, pH values in a range around pH 6.0 are most effective.

However, according to accepted practice for compositions that are to be used within living organisms, gelatin should be dissolved in an aqueous solvent buffered at pH 5.5-9.0, a range that encompasses the pH range of isotonic gelatin solution.

According to some embodiments of the present invention, the pH of the gelatin solution is optionally and preferably adjusted to fall within the range of pH levels at which mTG retains upwards of 80% of its enzymatic activity. For currently known strains of mTG, this range is from about 5 to about 8 (Activa® General Information, Ajinomoto Food Ingredients LLC).

The lower part of the high mTG activity pH range is preferred, since the mTG-facilitated cross-linking of gelatin releases $NH_3$ as a product, which raises the pH in the local environment during a cross-linking process. Without wishing to be limited by a single hypothesis, if the initial solution pH is at the lower part of the high mTG activity pH range, then the release of $NH_3$ during protein cross-linking will not immediately increase the local pH above the pH range for high mTG activity, enabling the mTG to function continuously at a high activity level. Hence, preferably, the pH of the gelatin solution component is adjusted to a pH in the range of from about 5 to about 8, and more preferably from about 6 to about 7. Most preferably, the pH of the gelatin solution component is adjusted to a pH of about 6, which is the optimal pH for activity of crude transglutaminase.

The pH can be adjusted using a pH adjusting agent or any other method known in the art. For example and without any intention of being limiting, one such method involves titration of a solution of dissolved buffer salts with acetic acid glacial until the solution pH reaches the desired pH level. After pH adjustment, the solution is transferred to a volumetric bottle and double distilled water is added until the desired buffer solution volume, and corresponding buffer concentration, is achieved.

Addition of Calcium and Urea

PCT Pub. No. WO/2008/076407, filed on Dec. 17, 2007, discloses that the addition of calcium chloride ($CaCl_2$) to gelatin solutions substantially reduces the transition point of gelatin. A 25% (w/w) gelatin solution in a buffer of 2M calcium chloride has a transition point below 22° C., sufficiently low to remain liquid at operating room temperature. However, mTG-facilitated cross-linking of gelatin is greatly inhibited in such a high $CaCl_2$ environment, greatly increasing the time required for gelatin gels to cure. Furthermore, the cross-linked gelatin product that results from mTG cross-linking in such an environment has inferior mechanical properties to cross-linked gelatin product resulting from mTG cross-linking in a lower $CaCl_2$ environment.

Surprisingly, the present inventors found that calcium chloride and urea have a synergistic effect on lowering the transition point of gelatin solutions. When both calcium chloride and urea are incorporated in a buffer solution at appropriate concentrations and gelatin (25% w/w, type A 300 bloom porcine) is dissolved into that buffer solution, the gelatin solution transition point can be reduced to below operating room temperatures (18-22° C.). In this synergistic solution, the required concentrations of urea and calcium chloride are each much lower than the concentrations which would be required if only one of these substances were used to lower the transition point of a gelatin solution. For example, in place of dissolving gelatin in a 2M solution of $CaCl_2$, the equivalent transition point lowering can be accomplished by dissolving gelatin in a 1M solution of $CaCl_2$ that includes 2M of Urea or a 0.5M solution of $CaCl_2$ that includes 3M of urea. Experimental examples of this effect are described with regard to the below illustrative, non-limiting examples.

In the absence of $CaCl_2$, a 4-4.5 M solution of Urea is required to lower the gelatin solution transition point equivalently. In many cases, when this synergistic solution for lowering transition point is used, the mechanical properties (cohesive strength, adhesive strength, and elasticity) of crosslinked gelatin gels resulting from mTG cross-linking are improved.

In another embodiment of the present invention, as an alternative to or in addition to $CaCl_2$, a different calcium compound is used. Examples of other calcium compounds are calcium hydroxide and calcium carbonate. The use of calcium hydroxide to lower the transition point of a gelatin solution that is then crosslinked using mTG is described with regard to the below illustrative, non-limiting examples.

In another embodiment, as an alternative to or in addition to a calcium compound, a compound that incorporates a different divalent cation is used. A non-limiting example of an appropriate divalent compound is magnesium chloride.

Transglutaminase Concentration

Addition of calcium chloride and/or urea to gelatin solution in order to reduce the transition point of the solution, has an inhibitory effect on mTG-facilitated cross-linking, even in the lower concentrations described above, thereby slowing the curing of the thermally irreversible gelatin gelation that is desirable for hemostatic, tissue sealing, tissue adhesion, and other wound treatment applications. The increase in mTG-facilitated protein cross-linking time resulting from the addition of urea or $CaCl_2$ may reduce the utility of protein mTG-crosslinking for the above-mentioned medical applications.

The present inventors have found that the rate of mTG-facilitated protein cross-linking reaction speed can be increased by increasing the concentration of mTG in the mTG solution that is mixed with a protein solution to start the mTG cross-linking reaction. Materials and methods for increasing the concentration of mTG in a solution, according to some embodiments of the present invention, include the use of a commercially available concentrated mTG mixture, the purification of mTG solutions from bulking agents, and the concentration of mTG solutions using filtration techniques. Through the use of these methods and materials, the protein concentration of mTG in a mTG solution can be increased up to a concentration of about 2% w/w (20% w/w solution of a 10% by weight mTG product, such as ACTIVA TG).

According to some embodiments, when urea and/or $CaCl_2$ are added to the gelatin solution buffer to reduce the transition point of gelatin solutions, the preferred protein concentration of the corresponding mTG solution is in the range of from about 0.1% to about 2% w/w of total mTG solution. More preferably, the concentration of the mTG solution is in the range of from about 0.25% to about 1% w/w of total mTG solution. Most preferably, the concentration of the mTG solution is in the range of from about 0.4% to about 0.8% w/w of total mTG solution.

According to some embodiments of the present invention, mTG solution is thoroughly mixed with the gelatin solution at a volume ratio ranging from 1:0.5 to 1:8, mTG solution: gelatin solution. Preferably, the volume ratio ranges from 1:1 to 1:4, mTG solution:gelatin solution; more preferably, the volume ratio ranges from 1:1 to 1:2, mTG solution:gelatin solution.

These volumetric ratios and mTG concentrations taken together describe embodiments of the current invention wherein the protein concentration of mTG in the total composition is in the range from about 0.01% to about 1.35% w/w, preferably in the range from about 0.05% to about 0.5% w/w, and more preferably in the range from about 0.1% to about 0.4% w/w.

According to some embodiments of the invention, the enzyme activity in the total composition is in the range from about 1 to about 180 enzyme units (EU) per gram, preferably in the range from about 4 to about 70 EU/g, and more preferably in the range from about 10 to about 55 EU/g.

Calcium Sequestering Agents

As disscussed above, although $CaCl_2$ is very useful in lowering the transition point of solutions comprising cross-linkable proteins or polypeptides, its presence in a cross-linked gelatin solution has deleterious effects. As such, a method of neutralizing the effect of $CaCl_2$ once cross-linking has occurred would be extremely useful in the development of a composition for use in medical and surgical sealant and hemostasis applications.

According to some embodiments of the present invention, the hemostatic or fluid sealing composition comprises calcium-binding agents. When a solution comprising the cross-linking material and at least one calcium-binding agent is mixed into a solution of a cross-linkable protein containing $CaCl_2$, the calcium-binding agents attach to the calcium molecules and reduce their negative effect on hemostatic or fluid sealing composition. The term "calcium-binding agents" in the context of this invention is synonymous with the terms "calcium-sequestering agents," "calcium-chelating agents," "calcium-chelators," "calcium-complexing agents."

It has further been surprisingly found by the inventors of the present invention that the addition of calcium-binding agents to a solution of a cross-linkable protein, such as gelatin, has additional effects aside from neutralizing calcium in the solution. When such agents are added to a gelatin solution, the gelatin solution undergoes physical thermo-reversible gelation. The rate of this gelation process is dependent on the concentration of the calcium-binding agent in the solution being added to the gelatin solution. Preferably, the concentration of calcium-binding agent in an mTG solution is in the range of from about 0.1 to about 0.5M. More preferably, the concentration range is from about 0.25 to about 0.5M. Above a concentration of 0.5M, the thermo-reversible gelation that is facilitated by certain calcium-binding agents may occur rapidly enough so as to severely hamper the mTG-facilitated cross-linking.

The thermo-reversible gelation triggered by the addition of a solution containing calcium-binding agents to a gelatin solution occurs even with gelatin solutions that do not form thermo-reversible gels at ambient temperatures. These types of gelatin solutions include those described above that contain amounts of urea and/or $CaCl_2$ that reduce the gelatin solution transition point below 18-22° C., sufficiently low to remain liquid at operating room temperature.

The thermo-reversible gelatin gels formed by the addition of calcium-binding agents to a gelatin solution are distinctly different from the thermo-reversible gelatin gels formed when a gelatin solution is brought to a temperature below its sol-gel transition point. The gelation process triggered by a reduction in temperature is generally a gradual process since gelatin solutions have low thermal conductivity and it takes a significant amount of time for the temperature of an entire gelatin solution to drop below its sol-gel transition point. The gel that is formed from the gelatin solution is clear and firm. The gelation process trigged by calcium-binding agents will occur nearly immediately if a sufficient amount of agent is added. The gel that is formed is opaque, white in color, and very stretchy. Furthermore, gels that result from calcium-binding agent gelation only revert back into solution at temperatures above 40° C., their approximate sol-gel transition point, which is significantly higher than the sol-gel transition point of gels that result from of 300 bloom gelatin.

Without wishing to be limited by a single hypothesis, the mechanism for the thermo-reversible, physical gelation triggered by the addition of certain calcium sequestering agents, such as citrate, EDTA and Calgon, possibly results from ionic crosslinking as these agents are negatively charged polyanions, Type A gelatin has an isoelectric point of 7-9 which means that it is positively charged in solution at pH 6.0 (as in the below referenced example). A negatively charged polyanion added to a negatively charged gelatin solution can cause ionic crosslinking.

In another optional embodiment of the present invention, a negatively charged polyanion that is not a calcium sequestering agent is used additionally or alternatively to the calcium sequestering agent or agents to introduce ionic crosslinking to the composition.

The thermo-reversible gelation that can be triggered through the addition of calcium-binding agents to a solution of gelatin or a related cross-linkable protein, has great benefit in improving compositions of mTG-facilitated cross-linked protein gels for medical and surgical applications. This is particularly true with regard to cross-linked gels made from gelatin solutions with sol-gel transition points below 18-22° C., which are sufficiently low to remain liquid at operating room temperature, such as those that contain the necessary amounts of urea and/or $CaCl_2$. The elasticity and cohesiveness of cross-linked gels made from gelatin solutions containing transition point-lowering additives are reduced since the gels then lack the physical, thermo-reversible gelation that normally takes place in gelatin solutions that makes gelatin gels elastic and cohesive. Reduced elasticity and cohesiveness significantly harm these gels when they are used for tissue sealant, hemostatic, or wound closure applications since the gels are then less able to withstand the flow of blood or other body liquids without cracking and permitting the liquid to break through the gel once it is in place on top of the wound site. However, if a calcium-binding agent is added to the mTG solution that is mixed with the gelatin solution to facilitate cross-linking, then the gelatin solution will also undergo physical, thermo-reversible gelation at the same time that it is undergoing mTG-facilitated cross-linking. The concentration of calcium-binding agent useful for this embodiment of this invention is optionally and preferably an amount that, on its own, will not result in thermo-reversible gelation within the period required for mTG-facilitated cross-linking to occur. If too much calcium-binding agent is added, then thermo-reversible gelation will occur immediately and mTG-facilitated cross-linking will not occur at all.

The thermo-reversible gelation triggered by calcium-binding agents occurs both in gelatin solutions where calcium or a calcium-containing molecule is included as part of the solution and in gelatin solutions that contain no calcium or calcium-containing molecules. In gelatin solutions not containing any calcium, the addition of calcium-binding agents is useful only in the thermo-reversible gelation effect that is triggered. In gelatin solutions that do contain calcium, either alone or in larger molecules, calcium binding agents are useful both in reducing the deleterious effects of calcium and in triggering the thermo-reversible gelation effect. The deleterious effects of calcium on a crosslinked protein/polypeptide composition can include inferior mechanical properties, specifically increased brittleness and a reduction in cohesive strength. Additionally, when calcium is present at high concentrations above its toxicity threshold, it can result in an adverse tissue response.

Non-limiting examples of calcium-binding agents that are useful in the context of the present invention include polyphosphate salts, such as pyrophosphates (including tetrasodium pyrophosphate, disodium dihydrogen pyrophosphate, tetrapotassium pyrophosphate, dipotassium dihydrogen pyrophosphate, and dipotassium disodium pyrophosphate), tripolyphosphates (including pentasodium tripolyphosphate, and pentapotassium tripolyphosphate), higher polyphosphate salts such as sodium and potassium tetraphosphates, and hexametaphosphate salts, also known as 'glassy phosphates' or 'polypyrophosphates', and carboxylates, (such as alkali metal citrate salts, alkali metal acetate, lactate, tartrate and malate salts, alkali metal salts of ethylenediaminetetraacetic acid (EDTA), and editronic acid).

Preferred examples of suitable calcium-binding agents include EDTA and sodium citrate.

An experimental example that described mTG-facilitated cross-linking of gelatin solutions where EDTA or sodium citrate has been added to mTG solutions in various concentrations is described with regard to the below illustrative, non-limiting examples.

A preferred example of a polyphosphate salt which is useful in the context of the present invention is powdered sodium hexametaphosphate (SHMP), sold under the commercial name Calgon™. Calgon forms complexes with ambient calcium ions in water. When used as part of the present invention, Calgon had a similar effect to that of other calcium-binding agents when introduced into gelatin solutions containing calcium. When introduced into gelatin solutions that did not contain calcium, Calgon triggered a similar thermo-reversible gelation process as other calcium-binding agents but also had the additional benefit of reducing the mTG-facilitated cross-linking time of the gelatin gels. Gels created that included Calgon were also observed to be more adhesive than gels created that included other calcium-binding agents.

Urea-Sequestering and Urea-Hydrolyzing Agents

As discussed above, urea may be added to a gelatin solution so as to lower its transition point significantly. This is of great benefit in simplifying the use of a gelatin-mTG compound in an operating room environment. However, the cross-linked gelatin gels formed in the presence of high concentrations of urea are non-ideal for certain applications as they have high osmotic pressure and can draw water out of surrounding tissues when implanted onto native tissue in the body.

According to some embodiments of the present invention, the effect of urea in a gelatin solution is neutralized, for example by including a urea-complexing agent or a urea-sequestering agent, along with an activator if necessary, in a mTG solution that is mixed with a gelatin solution to form a gelatin-mTG composition. Additionally, an agent that catalyzes the hydrolysis of urea can be included in the mTG solution with similar effect. When the mTG solution is mixed into a gelatin solution, the urea-sequestering or urea-hydrolyzing agent immediately forms a reaction with the urea in the gelatin solution and neutralizes, or reduces, its potentially undesirable effect on the gelatin-mTG composition. The urea-sequestering or urea-hydrolyzing agent may optionally have a positive effect on the mechanical properties of the gelatin-mTG composition and increase the composition's adhesive strength, cohesive strength, and/or elasticity (without wishing to provide a closed list and also without wishing to be limited by a single hypothesis).

A non-limiting example of an agent that is useful for catalyzing the hydrolysis of urea is urease, a commercially-available enzyme that catalyzes the hydrolysis of urea into carbon dioxide and ammonia. Urease occurs in many bacteria, several species of yeast and a number of higher plants. Two illustrative sources are: Jack beans (*Canavlia ensiformis*) from which it has been crystallized and thoroughly studied, and *Bacillus pasteurii*.

Urease is preferentially included in an mTG solution at concentrations ranging from about 0.1 M, to about twice the molar concentration of urea in the corresponding gelatin solution to which the mTG solution will be added to form a gelatin-mTG composition, up to the saturation point of urease in solution. For example, if 1M of urea is included in a gelatin buffer, then the maximum preferred concentration of urease is 2M. This preferred concentration relates to the 1:2, mTG solution:gelatin solution ratio that is preferential in the herein described gelatin-mTG compositions and allows for one molecule of urease for every molecule of urea.

According to some embodiments of the present invention, urease is included in an mTG solution along with a urease stabilizer. Non-limiting examples of such stabilizers are EDTA, in concentrations of from about 1M to about 3 M, or glycerol, in concentrations of approximately 50% v/v in mTG buffer solution. Further examples include glutathione and citrate, as described in U.S. Pat. No. 4,188,465.

A non-limiting example of a urea-complexing agent is paraffin, which can complex urea in the presence of an activating agent, such as low molecular weight alcohols and ketones. Such a process is described in U.S. Pat. No. 2,719,145.

Plasticizer

Some embodiments of the present invention comprise the addition of sorbitol to the solution of the cross-linking material, rather than to the cross-linkable protein component, of the composition.

Surprisingly, as described in greater detail below, it has been found that sorbitol included in a mTG solution can unexpectedly combine with a gelatin solution prior to the onset of gelatin cross-linking Sorbitol, when added to the mTG solution prior to mixing with the gelatin solution, increases the flexibility and elasticity of gelatin-mTG compositions. Such increased flexibility and elasticity may optionally represent improved properties for certain applications or uses of the compositions. Furthermore, sorbitol can act as a carrier molecule for the mTG, protecting it from oxidation and increasing the shelf-life of mTG solutions.

Though included in the mTG solution, the preferred concentrations of sorbitol to be added are preferably determined with reference to the amount of gelatin in the gelatin solution that corresponds to a particular mTG solution. The preferred concentration of plasticizer, expressed as a weight ratio of the amount of gelatin in the corresponding gelatin solution, ranges from 1:1 to 3:1. The amount of plasticizer added to the solution within this range does not have a significant effect on the cross-linking time of a gelatin solution.

As discussed above, the properties of an mTG-facilitated cross-linked gelatin composition can be altered depending on the buffer used for the mTG solution. For example, when sodium citrate buffer is used, the sorbitol-containing gelatin-mTG composition is extremely flexible. When sodium acetate buffer is used, the cross-linking time required to form a vigorous gelatin gel is greatly reduced. Both with sodium citrate and with sodium acetate buffer solutions, the gelatin-mTG composition is far more elastic and flexible in the presence of sorbitol than it is in the absence of sorbitol.

The addition of sorbitol to mTG solutions made with sodium citrate buffer described with regard to the below illustrative, non-limiting examples. The experimental data in this experimental example confirms that sorbitol further enhances the flexibility of gels made with mTG in sodium citrate buffer.

mTG facilitated cross-linking of gelatin gels, when sorbitol is included in the mTG solution, at a more rapid rate when sodium acetate is used as the buffer for the mTG solution in comparison to gels made when sodium citrate is used as the buffer, as described in greater detail below.

Further examples of plasticizers which may be used in the context of the present invention include, without limitation, citric acid alkyl esters, glycerol, glycerol esters, phthalic acid alkyl esters, sebacic acid alkyl esters, sucrose esters, sorbitan esters, acetylated monoglycerides, glycerols, fatty acid esters, glycols, propylene glycol, lauric acid, sucrose, glyceryl triacetate, poloxamers, diethyl phthalate, mono- and diglycerides of edible fats or oils, dibutyl phthalate, dibutyl sebacate, polysorbate, polyethylene glycols (PEG) 200 to 20,000, Carbowax polyethylene glycols, polyvinyl alcohol (PVA), gum arabic, guar gum, xanthan gum, Plasdone® (polyvinylpyrrolidone), mannitol, and mixtures thereof.

Gum arabic, guar gum, PVA, PEG 6000, and Plasdone were shown to increase the flexibility of mTG-crosslinked gelatin composition. Preferably, the plasticizer of the present invention comprises one or more of sorbitol, polyethylene glycol, polyvinyl alcohol, or gum arabic, although other useful plasticizers are also encompassed within these embodiments of the present invention as described herein.

Kosmotropes and/or Osmolytes

Kosmotropes are substances that increase the order of water molecules in the solvation layer around proteins in aqueous solution and as a result:

Stabilize macromolecules and proteins in aqueous solutions

Increase hydrophobic effects, intermolecular interactions, and aggregation of proteins.

The effect of kosmotropes on biomolecules is usually opposite to that of chaotropes, such as urea and guanidinium chloride (GuCl). Chaotropes disrupt the structure of water and, as a result, new hydrogen bonds are formed between water and the protein at the expense of protein-protein interactions resulting in:

Solubilization of aggregates

Unfolding of globular proteins by exposing internal hydrophobic regions in the proteins to the solution As described above, chaotropes such as urea and GuCl can be used to disrupt the physical gelation of certain protein/polypeptide solutions by destabilizing the hydrogen bonding network between the protein/polypeptide chains. These chaotropes thus lower the sol to gel transition temperature of these solutions.

However, disrupting the physical gelation of protein/polypeptide solutions can, in some circumstances, have adverse effects on the mechanical properties of a crosslinked protein composition. For example, physical gelation can act to increase the elasticity of such compositions. Disrupting the physical gelation can then reduce the elasticity of these compositions and increase their brittleness, which may be undesirable for certain applications.

By incorporating a kosmotrope into the crosslinking material solution, physical gelation can be stimulated to occur in combination with, preferably simultaneously to, the gelation mediated by the crosslinking material, thus maintaining the beneficial mechanical property effects of physical gelation.

In some embodiments of the present invention, the sol-gel transition point of the protein/polypeptide solution has been lowered and one or more kosmotropes are incorporated into the crosslinking material or crosslinking material solution.

In a preferred embodiment, the kosmotrope is added at a concentration sufficient to cause physical gelation in a protein/polypeptide solution.

A non-limiting range of kosmotrope concentrations is 0.5-1M of the combined crosslinked protein composition.

In some embodiments, the kosmotrope is an ionic kosmotrope.

In a preferred embodiment, the kosmotrope is a non-ionic kosmotrope.

Non-limiting examples of non-ionic kosmotropes are proline and trehalose.

Non-limiting examples of ionic kosmotropes are trimethylamine N-oxide (TMAO) and glutamate (glutamic acid).

The stabilizing effect of kosmotropes on protein stability in vitro and their counteraction of urea may be related to their in vivo function as osmolytes. A good correlation between these in vitro and in vivo functions has been demonstrated for proline (Fisher M T et al., PNAS 103, 2006: p. 13265-6).

In a preferred embodiment, the kosmotrope for use in the present invention is an osmolyte.

Non-limiting examples of an osmolyte are glutamate or proline.

Crosslinker Inhibitors

As the crosslinking density in a protein/polypeptide solution is increased, the stiffness of the crosslinked composition is increased. Therefore, where increased flexibility or elasticity is desired from a crosslinked protein composition, it can be useful to limit the crosslinking density in the composition. One manner of accomplishing this is to reduce the amount of crosslinking catalyzed by the crosslinking material in the protein solution by introducing a crosslinker inhibitor into the composition.

In an embodiment of the present invention, a crosslinking inhibitor is added to either the protein solution or crosslinker solution such that the crosslinking level of the crosslinked composition is reduced.

In a preferred embodiment of the present invention, the crosslinking material is an enzyme and the inhibitor is an enzymatic inhibitor.

In a more preferred embodiment of the present invention, the crosslinking material is a transglutaminase (TG) and the inhibitor is a transglutaminase inhibitor.

In a more preferred embodiment of the present invention, the crosslinking material is a microbial transglutaminase (mTG) and the inhibitor is an mTG inhibitor.

Non-limiting examples of mTG inhibitors include cystamine, an organic disulfide that can form a disulfide bridge with mTG, cysteine, a hydrophobic amino acid with a reactive S—H side chain (thiol group), melanin, denaturants, other compounds with thiol groups or disulfide bonds, lysine, and compounds <5 kDA in size containing mTG substrates.

Thiol side chains, such as those in cystamine, cysteine, dithiothreitol (DTT), and mercaptoethanol, can serve as inhibitors as they can block the active sit of mTG by reacting with the mTG thiol group.

Melanin was previously described as having function as a competitive mTG inhibitor (Ikura K et al. *Biosci Biotechnol Biochem*. 66(6), 2002, p. 1412-1414).

In a preferred embodiment of the present invention, the inhibitor is included in quantities sufficient to inhibit crosslinking activity by less than 50%. In a more preferred embodiment, it is included in quantities sufficient to inhibit crosslinking activity by less than 30%.

In another embodiment of the present invention, the inhibitor is released into the composition after crosslinking has already begun.

PEG or PVA Copolymers of Crosslinkable Protein/Polypeptide

According to some embodiments, polyethylene glycol (PEG), also known as poly(ethylene oxide) (PEO) or polyoxyethylene (POE), is added to the protein/polypeptide or crosslinker solution as a copolymer, to improve one or more properties of the composition, for example (and without limitation) to increase the flexibility of the composition or to shield from the body's immune response to the protein-crosslinker composition. PEG is available over a wide range of molecular weights from 300 Da to 10 MDa and may be a liquid or low-melting solid, depending on the molecular weights.

Different forms of chemically-modified PEG are also available, depending on the initiator used for the polymerization process, the most common of which is a monofunctional methyl ether PEG (methoxypoly(ethylene glycol)). PEGs are also available with different geometries. Branched PEGs have 3 to 10 PEG chains emanating from a central core group. Star PEGs have 10-100 PEG chains emanating from a central core group. Comb PEGs have multiple PEG chains normally grafted to a polymer backbone. All of these types of PEGs should be considered useful in the present invention.

PEGs can be added to either the protein or crosslinker components of a protein-crosslinker composition. Preferentially, PEG is added at a dry weight ratio between 20:1 to 1:1, protein:PEG. PEG can be added to the protein component or crosslinker component through modification of the protein or crosslinker and/or modification of the PEG molecules. One example of such modification is the process known as PEGylation. PEGylation is the act of covalently coupling a PEG structure to another larger molecule. This process can be performed on either the protein or crosslinker molecules.

The gelatin PEGylation embodiment has, among its many advantages and without wishing to be limiting, the advantage that the PEG is part of the protein chain, therefore inducing changes in properties of the protein surface including but not limited to charge and hydrophilicity, as well as steric effects that are due to its bulkiness. As a result, the covalently attached PEG can have profound effects on intermolecular interactions between protein chains and in turn on physical gelation and crosslinker dependent crosslinking as well as on the mechanical properties of gels prepared by these methods.

The PEG molecules used in PEGylation are usually activated, meaning they react spontaneously with functional groups on the target protein. A non limiting example of PEGylation is using NHS ester derivatives of PEG. These activated PEG molecules react with primary amines on proteins to form amide bonds with the release of N-hydroxysuccinimide (NHS).

Other ways in which a protein can be modified is by reacting the primary amines found inside chains of lysine and at the amino termini of the protein chains. The modification may be by alkylation, succinylation, carbamylation, or by any other method of protein modification.

In a preferred embodiment, the crosslinkable protein/polypeptide is first reacted with activated PEG to create PEGylated protein. The PEGylated protein is purified from excess unreacted PEG and other reaction products by methods such as, but not limited to, dialysis, ultrafiltration, and gel filtration chromatography. The PEGylated protein can then be reacted with a crosslinker to form a crosslinked gel, PEGs can also optionally be added through the use of PEG amine as a substrate for a crosslinker that targets amine groups. The crosslinker crosslinks the PEG molecule through its terminal amine group to crosslinker substrates on the protein molecule, thus competing with the natural amine groups on the protein.

PEG amines comprise PEG that has been bound to amine-functional groups. These are commercially available in all types of PEG geometries. Sources of amine-functional PEG products include NOF (Japan), Nanocs (New York, N.Y.) and Pierce Biotechnology (Rockford, Ill.).

In all approaches of incorporating PEG, the number of natural substrates available for crosslinking is reduced, resulting in reduced cross-linking. This may affect the mechanical properties of the crosslinked gel, for example optionally allowing it to become less rigid and more flexible. In addition and without wishing to be limited by a single hypothesis, the PEG molecule itself may act as a plasticizer and further contribute to the flexibility of the resulting gel.

According to a preferred embodiment, the PEG amine comprises active lysine amino acids.

According to another embodiment, of the present invention, Polyvinyl Alcohol (PVA) is added to a gelatin or mTG solution as a copolymer to increase the flexibility or adhesiveness of a protein-crosslinker composition. PVA is a water-soluble synthetic polymer with high tensile strength and flexibility. In a high humidity environment, such as inside the body, PVA will absorb water. The water, which acts as a plasticizer, can then reduce the tensile strength of the PVA, but increase its elongation.

According to some embodiments, the copolymer comprises PVA-amine. When the amine-targeting crosslinker is added to the solution, both the protein and PVA-amine will act as substrates and a protein-PVA copolymer will be formed with better flexibility than a comparable cross-linked protein polymer.

A non-limiting example of a process that can be used for producing amine functional derivatives of poly(vinyl alcohol) is described in U.S. Pat. No. 6,107,401.

Another non-limiting example of a process that can be used for producing an amine copolymer of PVA is described in U.S. Pat. No. 4,931,501 where poly(vinyl alcohol) is reacted with an amino-aldehyde dialkyl acetal.

A process of synthesizing amine-modified poly(vinyl alcohol)s by a two-step process using carbonyl diimidazole activated diamines to produce PVAs with different degrees of amine substitution has also previously been described (Wittman M, et al. *Biophysical and Transfection Studies of an Amine-Modified Poly(vinyl alcohol) for Gene Delivery. Bioconjugate Chem.*, 16 (6), 1390-1398, 2005), as another non-limiting example.

Surfactants

According to some embodiments of the present invention, one or more biocompatible surfactants are added to the solution of cross-linkable protein or polypeptide, for example in order to reduce the surface tension of that solution.

Surfactants are wetting agents that lower the surface tension of a liquid, allowing easier spreading, and lower the interfacial tension between two liquids. Lower surface tension facilitates easier handling of a solution of a cross-linkable peptide as it is easier to pass through an applicator, and easier to mix with a solution of a cross-linking material. Surfactants can also lower the viscosity of the solution. Additionally, lowering the surface tension of a gelatin solution has great utility when a gelatin solution is lyophilized either alone or together with a mTG solution, as it can prevent the formation of a film on the top layer of the dried gelatin. Such a film inhibits the reconstitution of lyophilized gelatin into a homogenous solution.

Non-limiting examples of biocompatible surfactants useful in context of the present invention are polysorbate 20 (Tween™ 20), polyoxyethyleneglycol dodecyl ether (Brij™ 35), polyoxyethylene-polyoxypropylene block copolymer (Pluronic™ F-68), sodium lauryl sulfate (SLS) or sodium dodecyl sulfate (SDS), sodium laureth sulfate or sodium lauryl ether sulfate (SLES), poloxamers or poloxamines, alkyl polyglucosides, fatty alchohols, fatty acid salts, cocamide monoethanolamine, and cocamide diethanolamine.

Surfactants may be used also as plasticizers. Tween80 for example has been shown to reduce the glass transition point ($T_g$) of several hydrophilic polymers. The presence of the smaller molecules of Tween80 within the polymer were thought to dilute and weaken the cohesive interactions between the polymers chains. This reduced the friction and entanglement by increasing the free volume in the polymer matrix. (Ghebremeskel et al, 2006, International Journal of Pharmaceutics 328:119-129).

In a preferred embodiment of the present invention, one or more surfactants are used as a plasticizer to improve the elasticity of the crosslinked composition, particularly as it stiffens over time.

In another optional embodiment, one or more surfactants are combined with another plasticizer from the plasticizers listed above as relevant to the present invention. Rodriguez et al (Food Research International 39 (2006) 840-6) demonstrated a synergistic effect between a plasticizer (glycerol) and surfactants (Tween20, Span 80, Lecithin) on increasing the elasticity of non-crosslinked dry gelatin films.

Preferentially, surfactants are added to a gelatin solution at a weight ratio of 0.1-5% of the dry weight of gelatin in the solution. Alternatively, surfactants are added to a gelatin solution at a concentration approximately equal to the critical micelle concentration (CMC) of that particular surfactant in solution. The CMC of each surfactant varies and is dependant on the ionic concentration of the solution into which the surfactant is dissolved.

Tissue Substrate Neutralization

According to some embodiments of the present invention, the hemostatic or body fluid sealing composition further comprises substrate-specific binding agents, which neutralize adhesion-inhibiting effects of surface substances on a tissue substrate being sealed, attached, or otherwise treated, with the composition. For example, these agents can bind, dissolve, and/or disperse substrate surface substances with anti-adhesive effects.

According to a preferred embodiment, the composition of the present invention is targeted to adhere to mucous membranes, such as that of the gastrointestinal tract (GIT) or the buccal mucosa.

Tissues in the GIT, such as the intestines, are frequently mucosal, covered with mucus that is continuously produced. Since the mucus is constantly refreshing itself, successful adhesion to tissue in the GIT requires the composition to specifically adhere to the tissue itself, under the mucosal layer.

One way of specifically adhering targeting regions of the GIT is by using mucoadhesives that can reversibly bind to cell surfaces in the GIT. These mucoadhesives function with greater specificity because they are based on receptor-ligand-like interactions in which the molecules bind strongly and rapidly directly onto the mucosal cell surface rather than the mucus itself.

A non-limiting example of a class of compounds that has these unique requirements are lectins. Lectins are proteins or glycoproteins and share the common ability to bind specifically and reversibly to carbohydrates. They exist in either soluble or cell-associated forms and possess carbohydrate-selective and recognizing parts. The intestinal epithelial cells possess a cell surface composed of membrane-anchored glycoconjugates. It is these surfaces that could be targeted by lectins, thus enabling an intestinal delivery concept (Shah K U, Rocca J G., *Drug Deliv. Tech.*, 2004, 4(5), 1).

A non-limiting example of a mucoadhesive lectin is tomato lectin (TL). TL has been extensively studied in in vitro binding and shown to bind selectively to the small intestine epithelium (Lehr C, Bouwstra J A, Kok W, Noach A B, de Boer A G, Junginger H E. *Pharma Res.*, 1992, 9(4), 547-53.)

Lectins are useful for improving adhesion to all mucosal tissue surfaces that contain membrane-anchored glycoconjugates. Non-limiting examples of such tissue surfaces are buccual mucosa and the walls of the intestinal tract.

A non-limiting example of a compound to improve buccal mucoadhesion is a copolymer of poly(aspartic acid) (PAA) and polyethylene glycol (PEG) monoethylether monomethacrylate (PAA-co-PEG) (PEGMM) (Shojaei A M, Li X. *J. Control. Release*, 1997, 47, 151-61.27.) Preferably the PEGMM is 16-mole % PEGMM, which has the most favorable thermodynamic profile and the highest mucoadhesive forces.

According to some embodiments of the present invention, the mucoadhesive is a commercially available mucoadhesive hydrogel. Non-limiting examples of hydrogels suitable for use in improving the substrate specific adhesion of the herein described novel compositions are available under the tradename Corplex® (Corium Technologies, Menlo Park, Calif.). These adhesive hydrogels are prepared by non-covalent (hydrogen bond) cross-linking of a film-forming hydrophilic polymer (for example polyvinyl pyrrolidone, (PVP)) with a short-chain plasticizer (typically but not necessarily PEG) bearing complementary reactive hydroxyl groups at its chain ends.

Another non-limiting example of mucoadhesive compounds includes polymers with one or more thiol groups. In such polymers, the introduction of a sulphahydryl group increases the adhesive properties of the mucoadhesive polymers (Bernkop-Schnurch A, Schwarch V, Steininger S. *Pharm. Res.*, 1999, 16, 6, 876-81.32). The improved adhesion was demonstrated on porcine intestinal mucosa. Thiolated polymers (thiomers) have also demonstrated strong buccal adhesive properties (Langoth N, Kalbe J, Bernkop-Schnurch A. *Int. J. Pharm.*, 2003, 252, 141-48.)

Another non-limiting example of a buccal adhesive is a natural mucoadhesive gum derived from Hakea (Alur H H, Pather S I, Mitra A K, Johnston T P. *Int. J. Pharm.*, 1999, 88(1), 1-10.)

Enzyme Purification & Concentration

According to some embodiments of the present invention, transglutaminase solutions undergo one-stage or multiple-stage purification to perform one or more of 1) remove fermentation residue from the transglutaminase mixture; 2) concentrate the amount of active translglutaminase in a transglutaminase solution; 3) further purify the transglutaminase solution from carrier proteins or carbohydrates; 4) lower the endotoxin level of the transglutaminase solution; and/or 5) remove all microbes from the transglutaminase solution, effectively sterilizing the solution; all without wishing to be limited to a closed list.

The present invention, in at least some embodiments, further provides a method for preparing a hemostatic or body fluid sealing composition, the method comprising providing a solution of a cross-linkable protein or polypeptide; providing a solution of a cross-linking material; and mixing the solution of the cross-linkable protein or polypeptide with the solution of cross-linking material.

According to some embodiments, the solution of cross-linking material is filtered prior to mixing with the cross-linkable protein of polypeptide.

In a preferred embodiment of this invention, the filtration process first uses coarse filtration, sometimes known as clarification, to remove large blocks of fermentation residue that will rapidly block finer filtration steps. Non-limiting examples of such coarse filtration is about 0.45 µm pore size filtration and about 0.65 µm pore size filtration.

According to another preferred embodiment of the present invention, the solution of cross-linking material is optionally and preferably passed through a filter of pore size of below 0.22 µm, for example to reduce the bioburden of the material below 10 colony forming units (CFU) per gram and make it appropriate for medical use. Preferably, the bioburden is practically eliminated to achieve a sterility assurance level (SAL) of less than about $10^{-2}$ and more preferably less than about $10^{-3}$, where SAL is a term used in microbiology to describe the probability of a single unit being non-sterile after it has been subjected to a sterilization process.

According to another preferred embodiment of the present invention, either tangential flow or hollow fiber ultra-filtration techniques are used, not only to purify the solution of cross-linking material by removal of carrier carbohydrates and proteins, but also to concentrate the solution. Preferred pore sizes for use with this invention are those with pore sizes smaller than the size of the components of the cross-linking composition.

In a preferred embodiment, the crosslinking material is mTG and the pore size is in the range of 10-50 kDa. In a more preferred embodiment, the crosslinking material is mTG and the pore sizes are in the range of 10-30 kDa.

According to another embodiment, on or more size exclusion chromatography steps is used to selectively separate the crosslinking material from surrounding substances.

According to another embodiment, one or more hydrophobic or hydrophilic interaction chromatography steps is used to selectively separate the crosslinking material from surrounding substances.

According to another preferred embodiment of the present invention, the crosslinking material is a protein and one or more ion exchange chromatography steps is used to preferentially bind the crosslinking protein, thereby purifying it from the surrounding materials.

According to a more preferred embodiment, the crosslinking protein is mTG and one or cation exchange chromatography steps is used to purify the mTG.

In a preferred embodiment, the cation exchange resin is a sepharose resin.

According to another preferred embodiment, purification reduces the endotoxin level of the crosslinking material to <5 endotoxin units (EU) per gram.

According to another preferred embodiment, the crosslinking material is mTG and purification results in an mTG composition wherein the specific activity is greater than 20 enzyme units per milligram and preferably greater than 25 units per milligram.

According to another preferred embodiment, the crosslinking material is mTG and purification results in electrophoretic purity of at least 95% and preferably of at least 98%.

An mTG purification process, as a non-limiting example, is described herein that purifies a food-grade mTG product to produce an mTG composition with specific activity >25 enzyme units per milligram, >95% electrophoretic purity, <5 endotoxin units per gram, and <10 CFU/g.

As described above, mTG concentration is also a preferred parameter for some embodiments of the composition of the present invention. The above purification processes may also result in more concentrated mTG material. In addition to cross-linking gelatin more rapidly than non-concentrated mTG solutions, concentrated mTG solutions formed gels that were more elastic, more adhesive, and more transparent compared to the non-concentrated controls.

Increased Viscosity of Enzyme Solution

According to another embodiment of the present invention, the viscosity of the non-toxic cross-linker solution is increased so as to decrease the viscosity disparity between the cross-linker and gelatin solutions. A reduced disparity in solution viscosity enables rapid and homogenous mixing of the two solutions.

In a preferred embodiment of this invention, the viscosity of the cross-linker solution is increased to between 50 and 5000 cP.

In a more preferred embodiment of this invention, the viscosity of the cross-linker solution is increased to between 150 and 2500 cP.

In a non-limiting example of this embodiment, high molecular weight molecules without amine functionality are added to the cross-linker solution to increase its viscosity. Non-limiting examples of such molecules are soluble starches, polyvinyl alcohols (PVA), polyethylene glycol (PEG).

In a preferred embodiment of this invention, one or more viscosity increasing agents is added to the crosslinker solution to increase the viscosity of the solution without inhibiting the crosslinking reaction by more than 50%, preferably without inhibiting the reaction by more than 30%, and even more preferably without inhibiting the reaction. Non-limiting examples of appropriate viscosity increasing agents include alginate ester, gum arabic, carboxymethyl cellulose (CMC), xanthan gum, guar gum, and plasdone.

Inhibition of Carbamylation in Cross-Linkable Proteins/Polypeptides

As described earlier in the present patent, urea is used in some embodiments of this invention to decrease the sol-gel transition point of a protein solution. One disadvantage that can arise from the use of urea is that it can dissociate into cyanic acid. The cyanate ion reacts with primary amine groups on the protein to yield a carbamylated derivative. This defunctionalizes amine groups on the crosslinkable protein in a process known as carbamylation. In preferred embodiments of the present invention, one of the crosslinking substrates in the crosslinkable protein comprises one or more amine groups. When these group(s) are defunctionalized, the number of available substrates for crosslinking are reduced and the crosslinking rate decreases. The time during which urea is present in solution as well as the temperature of the solution affects the rate of carbamylation, since urea decomposes into cyanates over time at a rate that is temperature dependant.

It is not surprising that carbamylation is potentially problematic for the described embodiments of the present invention, as this process has previously been described as having adverse effects on amine-functional proteins and polypeptides. U.S. Pat. No. 4,605,513 describes a method for inhibiting carbamylation of polypeptides by using 1,2-ethylene diamine or compounds that are structurally related to 1,2-ethylene diamine. U.S. Pat. No. 7,459,425 B2 describes a process for inhibiting carbamylation of polypeptides in a urea or cyanate containing solution by adding a carbamylation inhibitor.

The carbamylation inhibition processes described in the background art rely on the use of competitive amine group substrates to bind the cyanate ions that would otherwise cause carbamylation on the target molecule. These background art processes can cause problems with regard to preferred embodiments of the present invention, since the crosslinkable substrates of the crosslinkable protein include amine groups. Therefore, the addition of competitive amine group substrates can competitively inhibit the crosslinking of the target crosslinkable protein. As an example of this, hydroxylamine, which was disclosed as a preferred carbamylation inhibitor in U.S. Pat. No. 7,459,425 B2, was found by the present inventors to increase the crosslinking time of protein solutions that had been incubated with urea.

The crosslinking material may optionally comprise a chemical entity that has functional groups which react with primary amines, including but not limited to aryl azides, Carbodiimide, Hydroxymethyl Phosphine, imidoesters, NHS-esters, vinyl-sulfones, diisocyanates and aldehydes such as glutaraldehyde and formaldehyde for example.

The cross-linking material may also optionally (alternatively or additionally) comprise an enzyme crosslinker with an amine group substrate. Preferably, the enzyme crosslinker use the epsilon amino groups of lysines as a substrate. Non-limiting examples of such an enzyme are microbial transglutaminase (mTG) and tissue transglutaminases.

It would be expected that the compounds described in the background art will inhibit transglutaminase dependent crosslinking because these compounds contain primary amines which are preferred substrates of transglutaminases. Surprisingly, it has been discovered by the present inventors that carbamylation in a protein/polypeptide solution can be inhibited through the addition of a competitive carbamylation inhibitor without adversely affecting amine-group dependant crosslinking of the protein/polypeptide, in contrast to the teachings of the background art.

In an embodiment of the present invention, a carbamylation inhibitor is included in the crosslinkable protein/polypeptide composition.

A non-limiting description of a carbamylation inhibitor is any molecule that can be a more preferable substrate for carbamylation than the target protein/polypeptide.

Non-limiting examples of inhibitors are molecules that have primary amines in their structure.

In a preferred embodiment, the carbamylation inhibitors do not inhibit the crosslinkability of the polypeptide or do not inhibit its crosslinkability to a greater extent than they inhibit the carbamylation reaction.

In another preferred embodiment, the carbamylation inhibitors do not inhibit the crosslinker activity or do not inhibit its activity to a greater extent than they inhibit the carbamylation reaction.

According to preferred embodiments, the carbamylation inhibitor comprises an amino acid or amino acid salt.

According to a more preferred embodiment, the carbamylation inhibitor is one or more of glycine or histidine. According to a more preferred embodiment, the carbamylation inhibitor is glycine.

The glycine is optionally and preferably present at a concentration from about 0.05M to about 1.5M in the composition. More preferably, the glycine is used at concentrations from about 0.1M to about 0.9M.

Surprisingly, it was found by the inventors that although glycine contains an amine group, it did not inhibit transglutaminase crosslinking activity or the kinetics of mTG-dependant gelatin crosslinking.

Glycine was shown to inhibit carbamylation preferentially in a gelatin solution containing urea, as compared with other primary amine group containing substances, and in a dose dependant manner. Histidine can also optionally be used to inhibit carbamylation.

Sodium cyanate also results in an inhibitory effect, confirming that urea breakdown is responsible for inhibition of mTG crosslinking Modification of Amine Groups in Crosslinkable Protein In another embodiment of the present invention, the crosslinkable protein/polypeptide contains amine groups that are a substrate for the crosslinking material and the primary amine groups on the crosslinkable protein/polypeptide are modified.

In gelatin, the relevant amine groups are the epsilon amine on lysine side chains and the free amine at the amino termini of the gelatin chains.

Modifying amine groups on the crosslinkable protein/polypeptide can decrease the number of crosslinkable substrates available for crosslinking, thereby improving the mechanical properties of the crosslinked protein composition by maintaining the composition's elasticity or changing the chemical properties, such as surface charge or hydrophibicity, of the composition.

In an embodiment of the present invention, modification of primary amines may optionally be performed with one or more methods, including but not limited to alkylation, amidation, carbamylation, or succinylation.

In another embodiment, primary amine groups on gelatin can optionally be modified by reacting the protein with acetic anhydride, glutaric anhydride and citraconic anhydride.

In another embodiment, primary amines groups may also optionally be modified by reacting with derivatives of succinimidyl esters. In addition, primary amine groups may be modified by PEGylation. In a preferred embodiment, the protein/polypeptide is succinylated.

Succinylation is a process in which succinic anhydride reacts with the ε-amino group of lysine and/or the amino-N-terminal α-amino group of a protein/polypeptide.

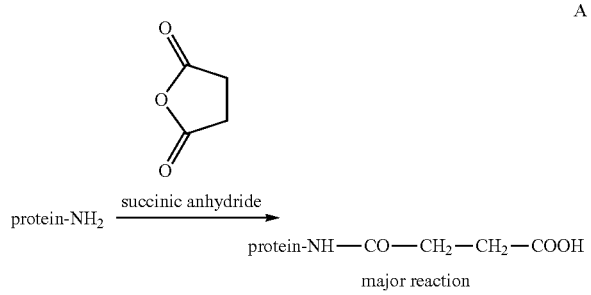

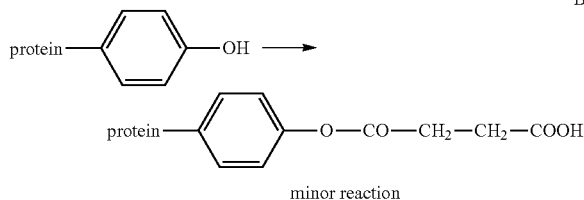

In a preferred embodiment, the crosslinking material is a transglutaminase and the primary amine groups on the crosslinkable protein are modified.

The succinylation of lysines in casein, for example, was shown to render the protein a non-substrate for transglutaminase (Nio et al, Agricultural and Biol Chem 50(4), 1986: p. 851-855).

In a preferred embodiment of succyinylation, succinic anhydride is optionally and preferably added to the protein/polypeptide to start the succinylation reaction. When the desired level of succinylation is achieved, the succinylated protein is preferably separated or purified from excess unreacted succinic anhydride and other reaction products by methods including but not limited to dialysis, ultrafiltration or gel filtration chromatography, or a combination thereof. Optionally the excess unreacted succinic anhydride is chemically reacted with one or more additives so as to functionally remove it from further reactions.

In another embodiment, the modified protein is optionally and preferably mixed with non-modified protein at ratios ranging from 1:10-10:1 weight modified protein per weight non-modified protein.

The modified protein may optionally be mixed with the non-modified protein prior to addition of crosslinking material or may optionally be added to the crosslinking material such that it is mixed with the non-modified protein only when the cros slinking material is added.

In another embodiment, a protein that would normally be a substrate for the crosslinking material is preferably modified and used to increase the viscosity of the crosslinking material solution.

In another embodiment, the crosslinking material is transglutaminase and a protein is preferably modified such that a majority of its lysine groups are rendered non-functional substrates, leaving glutamine groups that can be cross-linked by mTG in the presence of diamine linkers, including but not limited to ethylenediamine, diaminohexane, putrescine, cadaverine, spermine, spermidine and jeffamine.

In a preferred embodiment, the protein is gelatin.

Complete succinylation of gelatin caused gelatin to no longer be crosslinked by mTG.

Also as described below succinylated gelatin may optionally be used in a mixture with non-modified gelatin, for example and without limitation to improve the mechanical properties of a crosslinked gelatin composition.

In another preferred embodiment of the present invention, the protein/polypeptide in the composition is optionally and preferably modified through carbamylation.

Carbamylation of a protein is a process in which isocyanic acid reacts with amino group of a peptide and forms a carbamylated peptide.

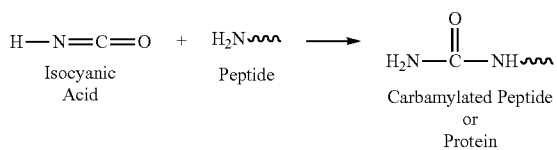

Carbamylation may optionally be used to modify amine groups when amine groups of proteins or peptides are used as substrate for crosslinking processes.

In a non-limiting embodiment, cyanate is optionally and preferably added to the protein/polypeptide to start the carbamylation reaction. When the desired level of carbamylation is achieved, the carbamylated protein is optionally separated or purified from excess unreacted cyanate and other reaction products by one or more methods including but not limited to dialysis, ultrafiltration or gel filtration chromatography, or a combination thereof. Optionally the excess unreacted cyanate is chemically reacted with one or more additives so as to functionally remove it from further reactions.

In a non-limiting embodiment, cyanate is preferably added directly to the protein/polypeptide before the start of the crosslinking reaction or during the crosslinking reaction to cause the carbamylation reactions.

Examples of cyanates that can be used for this purpose include but are not limited to sodium cyanate, ammonium cyanate, and potassium cyanate.

In another embodiment, the protein solution preferably contains urea and carbamylation begins as urea breaks down into ammonium cyanate.

Partial carbamylation is preferably accomplished by the addition of cyanates to the total protein-crosslinker composition at a concentration range of 0.001-0.1 mM per g protein. Preferably, cyanates are added at a concentration range of 0.01-0.05 mM per g protein to achieve partial carbamylation.

Concentrations above 0.05 mM per g protein, and preferably above 0.1 mM, may optionally be used to cause total carbamylation of the amine groups in a protein.

Cross-Linking Bridge Between Protein Molecular Chains (Diamine Molecules)

According to a further embodiment of the present invention, diamines for which transglutaminase has specific activity are added to a protein or crosslinker composition so as to be incorporated into the crosslinked protein composition as improve certain properties of the gelatin-mTG composition by creating cross-linking bridges between protein crosslinks Non-limiting examples of the benefits of cross-linking bridges (and without wishing to provide a closed list) include one or more of increased elasticity, modified bioabsorption time, or modified cohesive strength.

As above, this embodiment may optionally be useful for example if the crosslinkable protein contains amine groups that are a substrate for the crosslinker material In some cases, diamines can also be used to inhibit crosslinking kinetics. If the crosslinker targets epsilon amine groups on lysine side chains then the diamine can compete with the target substrates of the crosslinker and slow the crosslinking reaction.

Non-limiting examples for diamines that can be used are putrescine, cadaverine, hexanediamine, spermidine, and spermine. In addition, a diamine of the polyetheramine type, such as Jeffamine EDR-148 (Huntsman) may be used. Lysine and polylysine or a peptide containing 2 or more lysine residues may be used as well.

As mentioned in the modified amine group section, in another embodiment of the present invention, a transglutaminase is the crosslinker and one or more diamines may optionally be added to a protein solution where the amine groups have been modified. In such cases, the modified protein or some peptides therein may be not be cross-linkable by themselves. The diamine then provides primary amines for crosslinking by transglutaminase to take place. Among the many advantages of this approach is that the diamines would not compete with the natural lysines and slow down the crosslinking reaction. Rather, they would bridge the glutamine substrates in the target protein to each other through the diamine bridges. This process results, without wishing to be limited by a single hypothesis, in gels with longer and more flexible bridges in order to improve the flexibility of the crosslinked composition.

Some diamines can be used to modify the rate of protease biodegradation of the crosslinked protein composition. For example, lysine and hexanediamine have demonstrated the ability to reduce or accelerate the rate of protease biodegradation (Ma et al. Biomaterials. 2004, 25(15): p. 2997-3004).

In a preferred embodiment, the cross linking bridge is formed between lysine side chains in the crosslinkable protein/polypeptide through a diamine.

Non-limiting examples of diamines that can be used in this context are adipic diamide and glutaric diamide.

The effect of a diamine compound, petruscine, on the kinetics of a gelatin crosslinking reaction is described with regard to the below illustrative, non-limiting examples. Petruscine slowed down the crosslinking reaction in a dose dependent manner, suggesting that it serves as a substrate for transglutaminase and is crosslinked with the gelatin. It also increased the elasticity.

UHT Sterilization of Cross-Linkable Protein or Polypeptide

According to some embodiments of the present invention, ultra-high temperature sterilization (UHT) processing is used to sterilize a protein or polypeptide solution, such as a gelatin solution, in preparation for its use in a medical application. UHT is the sterilization of a material in liquid form by heating it for a short time, from around 3-180 seconds, to a temperature range of 120-140° C. The high temperature reduces the processing time, thereby reducing the spoiling of material properties. Precise temperature control in the UHT system ensures requisite bioburden reduction in the material.

Successful, repeatable heat sterilization of a protein solution requires that the entire amount of solution is brought to a particular temperature and held at that temperature for a set amount of time (acceptable time/temperature combinations are defined under GMP standards). This is defined as "hold time."

In an autoclave, the material typically is kept in the autoclave for 30-40 minutes to ensure that all parts of the materials have achieved the required temperature (generally about 121° C.) for at least the length of the hold time.

In UHT, the process is far more controlled and thus can be much quicker. Rather than undergoing heating all at once, the material undergoes a continuous flow process wherein small amounts of the material are being heated at any given time.

According to some embodiments of the present invention, traditional UHT is used to partially or fully sterilize the protein solution component of the herein described novel composition. In traditional UHT, the heating process for any particular aliquot of material takes a few seconds and then that material is kept at the temperature for the requisite hold time.

According to another embodiment of the present invention, the protein solution undergoes a process of deaeration prior to entry into the UHT system.

According to a preferred embodiment of the present invention, heating of the material in the UHT system is accomplished by indirect heating of the material, for example through the heating of water or steam.

According to another embodiment of the present invention, heating of the material in the UHT system is accomplished by direct heating of the material, for example through the injection of heated steam.

According to a preferred embodiment of the present invention, when UHT processing is conducted with direct steam injection heating, the protein or polypeptide solution being processed is initially prepared at a concentration higher than the concentration required for the final medically-useful protein/polypeptide-crosslinker composition.

In a more preferred embodiment of the present invention, the initial concentration of the protein/polypeptide solution being processed is about 5% (w/v) higher than the desired final concentration of that solution.

According to some embodiments of the present invention, microwave UHT is used, wherein the heating process for each aliquot takes less than 1 second, preferably less than 0.5 seconds, and more preferably approximately $2/10$ second prior to the hold time. This short heating time is made possible by ensuring that every part of the material passes through a uniform field of heat waves at a constant flow rate. This is a very controlled and extremely accurate process.

Successful sterilization of a gelatin solution for use in the present invention requires that the heating process does not result in any hydrolysis of the gelatin molecules. Autoclaving of protein solutions, for example gelatin solutions, is known to result in partial hydrolysis and a significant loss of cross-linking activity. Furthermore, autoclaving of gelatin solutions including materials such as urea results in a near total loss of cross-linking activity of the gelatin material. In other words, the extended heating period required for successful autoclaving results in certain undesirable effects on the gelatin solution material.

For protein processing, UHT is many times more delicate than autoclaving since the heating time required is far shorter than the time required in autoclaving. UHT does not result in significant partial hydrolysis of gelatin molecules in gelatin solutions.

Direct heating of the protein or polypeptide solution during UHT processing is the more rapid form of heating in traditional UHT. However, direct heating requires the injection of steam directly into the material. Normally, the steam is removed by vacuum once the material has been sterilized. However, this is impossible in a high viscosity protein solution such as a gelatin solution. Therefore, if direct steam injection heating is used, it is necessary to calibrate the UHT system to assess by what percentage the material being sterilized is diluted by the injected steam. Generally, this percentage is approximately 5%. Once the precise dilution percentage is determined, the initial solutions can be made more concentrated that is required to allow for dilution by steam injection.

Indirect heating, which takes about 20-30 seconds and is thus slightly slower than direct heating, is simpler than direct heating as it does not at all affect the content of the material being processed.

Although uniform microwave field UHT is a very new technology, it is also a very controlled and delicate sterilization method for use with protein solutions. Microwave UHT is dependent on uniform microwave wave technology, a relatively new technology. This technology allows an aliquot of material to be uniformly heated to a very specific temperature. The entire amount of the material is heated to that particular temperature. None of the material gets any hotter than that temperature and none escapes being heated to that temperature. The entire UHT process is dependant on the reliability and consistency of this uniform heating method. A standard microwave is not capable of creating a uniform field of heat waves. The result is that heating is always uneven to some degree. In a sterilization process that would ensure that the entire material is sufficiently heated, some sections of the material would get overheated and be unsuitable for use.

Microwave UHT minimizes the overall process time by accomplishing the rapid heating of direct steam injection heating without requiring any changes in concentration to the material being processed.

Deaeration of a solution prior to UHT processing can be greatly advantageous since air bubbles in a material undergoing UHT processing will burst over the course of the process. This can disrupt the process and result in uneven results of the sterilization heat process.

Preferentially, UHT processing of the protein or polypeptide solution is done using a system designed for miniature thermal processing, defined as continuous flow processing with a flow rate of less than 2 L/min. Even more preferentially, the UHT process is carried out with a flow rate below 1.2 L/min. Flow rates of this magnitude are optionally and preferably achieved using miniature traditional or uniform microwave UHT systems, such as those supplied by Microthermics (Raleigh, N.C.). A low flow rate allows for a more accurate and efficient UHT process.

Amine Donors

According to some embodiments of the present invention where primary amine groups are a substrate for the crosslinker material, an amine-donor is added to the gelatin solution to modify the crosslinking reaction kinetics or the mechanical properties of the crosslinked protein composition.

Polyamines are organic compounds having two or more primary amino groups. Owing to their chemical nature, polyamines can form hydrogen, ionic, or covalent linkages with other molecules. In animals, post-translational covalent linkages of polyamines to numerous proteins have been demonstrated, with much evidence indicating that these reactions are catalyzed by transglutaminases that form cross-linked complexes with two or one peptide-bound glutamine residues respectively (Serafinie-Fracassini D, et al. Plant Physiol. (1988) 87, 757-761. Ohtake Y, et al. Life Sciences 2007; 81, 7: p. 577-584).

Examples of suitable polyamines include but are not limited to poly-lysine, chitosan, or polyethylenimine.

Another suitable polyamine is polyvinylamine, a commercial amine-reactive PVA substance produced by BASF (Germany). The chain length and charge density of polyvinylamine molecule can be varied to obtain different characteristics of a copolymer incorporating polyvinylamine.

In some embodiments, the polyamine is optionally included in the protein composition prior to mixture of the protein with the crosslinker material.

In some embodiments, the polyamine is optionally included in the crosslinker composition prior to mixture of the protein with the crosslinker material.

In one embodiment, poly-lysine, a polymer of lysine that carries multiple positive charges and is used to mediate adhesion to living cells, is included. The interaction with living cells is mediated through negatively charged sialic acid carbohydrates found on membranes of most mammalian cells.

Another, non-limiting example of a polyamine that can be relevant for this purpose is polyethyleneimine.

In some embodiments, the polyamine is optionally added after crosslinking has begun. Normally, in type A gelatin there are more glutamines than lysines, 48 vs. 30 residues, respectively, per each 1000 amino acid residues of gelatin. Inclusion of polyamines in the composition can tilt the balance towards excess of primary amines. The primary amines can serve as anchor points for attachment into the tissue.

The addition of polyamines to the composition of the present invention can increase the cohesive strength of the composition as well as its adhesiveness, by increasing the number of reactive sites in the composition.

In addition, polyamines may form flexible crosslinking bridges between gelatin chains, thus increasing the flexibility of the crosslinked gel.

Also, polyamines have been shown to bind tissue fibronectin (see above references). Thus, polyamines incorporated into a protein-crosslinker composition can also act as intermediate agents that connect the composition to native tissue.

In a preferred embodiment of the present invention, polyethylenimine (preferably branched polyethylenimine) is optionally included in the protein composition.

Branched polyethyleneimine is a highly branched polymer with primary amine groups, secondary amine groups, and tertiary amine groups.

Example 29 describes the use of polyethylenimine (PEI), for example and without limitation, to increase the elasticity of a mTG-crosslinked gelatin composition.

Ammonia Scavenging, Sequestering and Binding Agents

Ammonia is highly toxic. Normally blood ammonium concentration is <50 µmol/L, and an increase to only 100 µmol/L can lead to disturbance of consciousness. A blood ammonium concentration of 200 µmol/L is associated with coma and convulsions.

Ammonium is produced in most cells of the body, as a result of deamination of amino acids and amines. The toxicity of ammonium above threshold concentrations of ammonium is due to the action of the enzyme glutamate dehydrogenase. This enzyme catalyses the oxidative deamination of glutamate to ammonium and ketoglutarate; the reaction is readily reversible, and the direction of reaction (towards deamination of glutamate or glutamate formation) depends on the relative concentrations of the various substrates. As the concentration of ammonium rises, so the reaction proceeds in the direction of formation of glutamate from ketoglutarate. Ammonia intoxication occurs when blood ammonium rises because the capacity to detoxify it by formation of glutamate and glutamine has been exceeded.

Molecules of ammonia are released by the cross-linking reaction facilitated by transglutaminases on fibrin, gelatin, and other proteins. Therefore, effecting a large amount of mTG cross-linking in a local physiological environment could, in extreme situations, result in the release of a toxic level of ammonia.

In an embodiment of the use of a gelatin-mTG composition in a physiological context, such as an implantable and/or surgical context, the local levels of ammonia are preferably reduced below the potentially dangerous threshold by the incorporation of an ammonia-scavenger agent, an ammonia-binding agents, or other ammonia-neutralizing agent in the gelatin-mTG composition. Such an agent could be included in either the gelatin component or mTG component that are mixed to form the gelatin-mTG composition.

A non-limiting example of such an agent is disaccharide lactulose. Lactulose is a synthetic disaccharide that is not hydrolysed by intestinal enzymes. Lactulose inhibits bacterial ammonia production by acidifying the content of the bowel. It promotes growth of colonic flora. The growing biomass uses ammonia and nitrogen from amino acids to synthesise bacterial protein, which in turn inhibits protein degradation to $NH_3$. Lactulose leads to less ammonia by inhibiting bacterial urea degradation and reduces colonic transit time, thus reducing the time available for ammonia production and expediting ammonia elimination. (Deglin J H, et al. *Lactulose*. In Davis's drug guide for nurses (9th ed., 2003) (pp. 589-590). Philadelphia: F. A. Davis.) Lactulose is commercially available from Solvay SA (Brussels), among other suppliers.

Another embodiment of this invention optionally and preferably features a mixture of four forms of the strong cation exchange resin, Amberlite™ IR-120 (Advanced Biosciences, Philadelphia, Pa.), in the treatment of ammonia intoxication. This resin mixture, with a total quantity of 750 mEq, when used in the extracorporeal circulation system, was found to be efficient in the correction of hyperammonemia of experimental dogs and to be unaccompanied by any untoward effects. (Juggi J S, et al. *In-Vivo Studies with a Cation Exchange Resin Mixture in the Removal of Excessive Ammonium from the Extracorporeal Circulation System. ANZ J Surg* 1968; 38 (2): p 194-201).

Another embodiment of this invention optionally and preferably features saponins, particularly yucca saponin, or the glyco-fraction derivative of *Yucca shidigera* plant, both of which have demonstrated ammonia-binding ability (Hussain I, Ismail A M, Cheeke P R. *Animal Feed Science and Technology*, 1996; 62 (2), p. 121-129).

Another embodiment of this invention optionally and preferably features a sodium phenylacetate and sodium benzoate solution as an ammonia scavenger. Such a solution is commercially available in a non-limiting example under the trade name AMMONUL® (Medicis, Scottsdale, Ariz.), which consists of a solution of 10% sodium phenylacetate, 10% sodium benzoate.

In another embodiment of the present invention, L-glutamine (L-Gln) or L-glutamate (L-Glu) is added to the protein-crosslinker composition, preferably to the protein component of the composition. L-Gln and L-Glu stimulate the metabolism of ammonia to urea in cells, and also inhibit the uptake and facilitates the extrusion of ammonia from cells (Nakamura E, Hagen S J. *Am J of Phys. GI and Liver Phys*, 2002; 46(6), p. G1264-G1275). Without wishing to be limited by a single hypothesis, in an in situ cross-linking process that releases ammonia, L-Gln and/or L-Glu have utility in neutralizing the released ammonia by reducing the amount of free ammonia in the environment, thereby reducing the amount absorbed by cells and accelerating the cells' natural ability to metabolize ammonia. The tissue response to a mTG-crosslinked gelatin composition over its initial 14 days of subcutaneous implantation in rats was significantly improved by the inclusion of glutamate to sequester the ammonia released by the mTG crosslinking reaction, as described with regard to the below illustrative, non-limiting examples.

Coloring Agents

In another embodiment of the present invention, a biocompatible coloring agent is added to either the protein or crosslinker solution to improve the visibility of the composition upon application.

Additional Hemostatic Agents

According to some embodiments of the present invention, any of the compositions described above may further comprise an additional hemostatic agent, which may be selected from the group consisting of coagulation factors, coagulation initiators, platelet activators, vasoconstrictors, and fibrinolysis inhibitors. Examples of these include but are not limited to epinephrine, adrenochrome, collagens, thrombin, fibrin, fibrinogen, oxidized cellulose, and chitosan.

Configurations of Lyophilized Product

In an embodiment of the present invention, a dried or frozen composition is formed wherein the cross-linkable protein or polypeptide is thoroughly mixed with the non-toxic cross-linker to form a homogenous solution and the temperature of the solutions is reduced immediately to prevent completion of the cross-linking process. The mixed composition is then either frozen or frozen and dried to form a novel, uniform composition.

This type of composition has great utility in that it allows for the precise control of the time that it takes for the composition to for a cohesive gel in situ. As can be seen in the viscometer graphs presented in the examples, the time that it takes for the cross-linking to occur can be very precisely defined. Since the activity of some cross-linkers, such as mTG, is temperature dependant, if the temperature of the composition is reduced below the active temperature of the cross-linker, the cross-linking process can be effectively halted. In the case of mTG, cross-linking activity is essentially halted below a temperature of approximately 20° C.

In a preferred embodiment of this invention, the reaction is stopped before the composition achieves 30% of its ultimate mechanical strength.

In a more preferred embodiment of this invention, the reaction is stopped before the composition achieves 15% of its ultimate mechanical strength.

In an even more preferred embodiment of this invention, the reaction is stopped before the composition achieves 5% of its ultimate mechanical strength.

Ultimate mechanical strength, for the sake of this embodiment, is defined as the point at which the all of the composition's cross-linkable material has been cross-linked to a sufficient degree so as to not be freely flowable. In viscometer testing, this point occurs roughly at 10M cP.

In an embodiment of the present invention, a dried composition is formed wherein the dry crosslinker material is thoroughly dispersed through a lyophilized composition of cross-linkable protein or polypeptide.

In a preferred embodiment, the protein is gelatin and a non-crosslinked gelatin foam is lyophilized prior to dispersal of crosslinker throughout such a porous foam.

In another preferred embodiment, dry crosslinker material is added to the gelatin foam such that the crosslinker does not dissolve into the foam (ie no crosslinking activity is observed prior to lyophilization).

It was surprisingly found that a reconstitutable foam could optionally be formed from a gelatin solution that was sufficiently stabile so as to allow for the lyophilization of the gelatin in foam form without the addition of any stabilizing or crosslinking agents.

In a preferred, illustrative embodiment of the present invention for forming such a foam, a gelatin solution is prepared and held at a temperature where it is in liquid form. The gelatin solution is then subjected to an extended and preferably continuous foaming process while it is cooled to a temperature below its sol-gel transition point.

The concentration of gelatin solution is preferably in the range of 0.5%-20% w/w, more preferably 5-10% w/w.

The initial temperature of the gelatin solution is 30° C.-70° C., preferably 30° C.-50° C., and more preferably 35° C.-40° C. The environmental temperature during the foaming process is 0° C.-25° C., preferably 15° C.-25° C. and more preferably 20° C.-23° C. Non-limiting examples of foaming processes include stirring, mixing, blending, and injection of a gas.

Preferably, the foaming process includes stirring or mixing.

One or more foaming techniques may optionally be used in the foaming process. Alternatively, one foaming technique may optionally be used multiple times under different conditions: for example, gentle stirring to generate a low level of foam following by vigorous stirring to achieve maximal aeration in the gelatin foam.

In an optional embodiment, upon the completion of foaming, the gelatin foam is preferably transferred to a vessel that had been cooled to a temperature lower than the temperature of the gelatin foam upon completion of the foaming process.

In another embodiment, the gelatin foam is optionally and preferably rapidly cooled immediately upon completion of foaming process. A non-limiting example of rapid cooling is exposing gelatin foam to liquid nitrogen immediately after the foaming process.

In a preferred embodiment, the dry gelatin foam contains less than about 12% moisture. In a more preferred embodiment, the dry gelatin foam contains less than about 8% moisture.

In another embodiment, the gelatin foam is optionally not further stabilized by cooling or other method immediately (within up to about 5 minutes) upon the completion of foaming such that the foam partially collapses resulting in the formation of a denser layer of gelatin foam on the bottom of the foam.

In an embodiment of the above, the denser layer optionally comprises less than about 50% of the thickness of the lyophilized gelatin composition, preferably less than about 35%, and more preferably less than about 20%.

Density as used here refers to an increase in the weight of gelatin per volume of lyophilized composition. Such an increase can optionally be as little as 5% but is preferably greater than about 10% and more preferably greater than about 20%.

Without wishing to be limited to a single hypothesis or to a closed list, it is believed that such a dense layer of gelatin foam provides mechanical strength to the lyophilized gelatin composition without affecting the reconstitution profile of the top part of the dry composition.

EXAMPLES

Reference is now made to the following examples, which together with the above description, illustrate some embodiments of the invention in a non limiting fashion.

Example 1

Comparison of Cross-Linking Time Using Acetate Buffer and Citrate Buffer

Materials

The following materials were used in the experiment: 300 bloom, type A porcine gelatin (Sigma, St. Louis, Mo.), Gelatin Medex—300 bloom 70 mesh, pharmaceutical gelatin [Medex, England batch], 98% urea [Alfa Aesar, Lancester], Calcium Chloride 97% dried powder [Alfa Aesar, Lancester], 0.1M Sodium Acetate buffer (pH 6.1), 0.5M Sodium Citrate dehydrate 99% [Alfa Aesar, Lancaster], D-Sorbitol 97% [Sigma, St. Louis, Mo.], 10% microbial Transglutaminase—ACTIVA-TG 10% (10% enzyme, 90% maltodextrin) [Ajinomoto, Japan].

Methods

Stock solutions of 2M Calcium solution, 4.5M and 5M urea, 0.1M Sodium Acetate solution pH 6.0, 0.5M Sodium Acetate solution pH 6.0, 2M Sodium Citrate solution pH 6.0 and, 2.36M Citric Acid solution was prepared.

25% (w/w) Gelatin solution with 2M urea, 1M Calcium, 0.1M Sodium Acetate (solution A) was prepared. 7.5% (w/w) microbial transglutaminase (10% w/w mTG—ACTIVA-TG) solutions were prepared by dissolving mTG in the following different solutions:

Solution 1—0.5M Sodium Acetate
Solution 2—0.5M Sodium Citrate

Viscometer Tests

For each viscometry test, 25 mL of gelatin solution was mixed with 12.5 mL of mTG solution in a 50 mL beaker. The viscosity of the mixed gelatin-mTG solution was then tracked as it underwent gelation. Different test groups were compared by recording the time required for each test group to achieve 30% and 90% of the maximum viscosity able to be recorded by the viscometer at the specific speed and with the specific spindle used for that test.

In this experiment, a DV II+ PRO Digital Viscometer (Brookfield Engineering, Middleboro, Mass.) was used with a T-E 95 "t-bar" spindle. A helipath viscometer stand was used to maintain vertical movement of the spindle over the course of the viscometer test. The helipath moved along a 1 cm path. The viscometer readings were outputted by the viscometer and read using HyperTerminal software at a rate of 1 reading per second. The rotational speed of the spindle for the viscometry test was 0.5 rpm. The maximum recordable viscosity at this speed with the T-E 95 spindle was $10 \times 10^6$ cP, meaning that the 30% point was equivalent to $3 \times 10^6$ cP and the 90% point was equivalent to $9 \times 10^6$ cP.

The beaker was submerged in a 37° C. water bath for the entire extent of the viscometer test. Average temperature within the beaker also recorded throughout the test to ensure consistency between test groups.

Results

Figure 2:
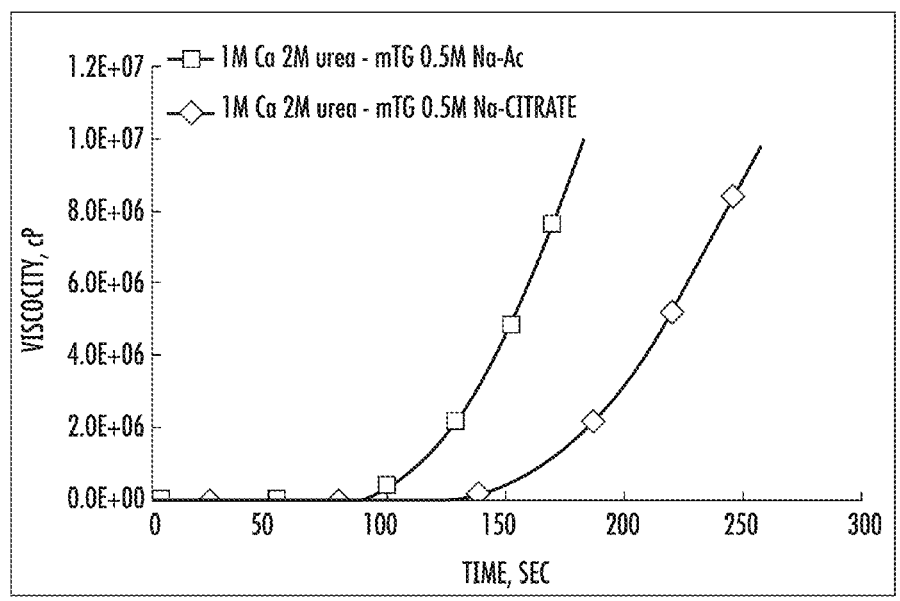
FIG. 2 is a graph showing viscosity changes with time of mTG in 0.5M Sodium Acetate (Na—Ac) and 0.5M Sodium Citrate.

FIG. 2 and Table 1 show viscosity changes of 25% (w/w) gelatin in 1M Calcium 2M urea (solution A) reacted with 7.5% (w/w) ACTIVA-TG 10% in 0.5M Sodium Acetate (solution 1) and 0.5M Sodium Citrate (solution 2).

TABLE 1

Comparison of viscosity changes with time of mTG buffers

| Solution | Time for 30% of maximal viscosity, sec | Time for 90% of maximal viscosity, sec |
|---|---|---|
| Solution A reacted with solution 1 | 127 | 168 |
| Solution A reacted with solution 2 | 187 | 234 |

The results of this experiment demonstrated that use of mTG in 0.5M Sodium Acetate led to a significantly shorter cross-linking time compared to mTG in 0.5M Sodium Citrate.

Example 2

Effects of Different Buffers and Buffer Ion Concentrations on Cross-Linking Time Materials The following materials were used in the experiments: 300 bloom, type A pharmaceutical porcine gelatin (70 mesh) [Ital Gelatine, Santa Vittoria d'Alba, Italy], Urea—minimum 99.5%, [Sigma, St. Louis], Calcium chloride 97% dried powder [Alfa Aesar, Lancester], Sodium Citrate Dehydrate 99% [Alfa Aesar, Lancaster], citric acid anhydrous [Frutarom, Israel], Sodium Acetate Trihydrate [Sigma, St. Louis], Acetic Acid Glacial analytical grade [Frutarom, Israel] and, 10% microbial Transglutaminase—ACTIVA-TG 10% (10% enzyme, 90% maltodextrin) [Ajinomoto, Japan].

Method

The following stock solutions were prepared: 2M of Calcium solution, 4M and 4.5M urea solutions, 0.1M sodium acetate solution, 2M of Sodium citrate solution and 2.36M Citric acid solution.

A 25% (w/w) gelatin solution in 2M urea and 1M $CaCl_2$ (solution A) was prepared. 7.5% (w/w) microbial transglutaminase was prepared and dissolved into the following six solutions:

Solution 1—0.1 M Sodium Acetate
Solution 2—0.25 M Sodium Acetate
Solution 3—0.5 M Sodium Acetate
Solution 4—0.25 M Sodium Citrate
Solution 5—0.5 M Sodium Citrate
Solution 6—0.6 M Sodium Citrate To determine cross-linking (XL) time, 2 mL of gelatin solution was mixed with 1 mL of each type of mTG solution. For each type of mTG solution, 3 separate samples were prepared in separate wells of a 12-well culture plate. Solutions were thoroughly mixed to form a homogenous solution and then cross-linking time was determined by time at which mixed solution formed a coherent, gelatinous mass.

Results

As shown in Table 2, it was found that lower ion concentrations (0.1M instead of 0.5M) in the mTG buffer results in quicker cross-linking both with Sodium Acetate and with Sodium Citrate buffer.

TABLE 2

Cross linking of gelatin using mTG solutions in different ionic strengths results. XL refers to cross-linking.

| Enzyme solution | Test No 1 | | Test No 2 | | Summary |
|---|---|---|---|---|---|
| | Time to XL | Description | Time to XL | Description | |
| 1 0.1M Sodium Acetate | 2 min | XL begins after 1 min | 2 min | XL begins after 1 min | A homogenous gel is formed after 2 min. |
| 2 0.25M Sodium Acetate | 2.5 min | After 1.5 min XL begins. | 2.5 min | After 2.5 min XL begins. | A homogenous gel is formed after 2.5 min. The gel becomes |

TABLE 2-continued

Cross linking of gelatin using mTG solutions in different ionic strengths results. XL refers to cross-linking.

| Enzyme solution | Test No 1 | | Test No 2 | | Summary |
|---|---|---|---|---|---|
| | Time to XL | Description | Time to XL | Description | |
| 3 0.5M Sodium Acetate | 4 min | After 1 min XL begins. The formed gel is very homogenous. | 4 min | After 1 min XL begins. The formed gel is very homogenous. | A homogenous gel is formed after 4 min. However, the gel becomes brittle after short period of time. |
| 4 0.25M Sodium Citrate | 2.5 min | Starts to XL after 1.5 min. | 2.5 min | Starts to XL after 1.5 min. | A gelatinous mass is formed after 2.5 min. |
| 5 0.5M Sodium Citrate | 4 min | Starts to XL after 1.5 min. | 4 min | Starts to XL after 1.5 min. | Forms a gelatinous mass after 4 min. |
| 6 0.6M Sodium Citrate | 4 min | Non uniform gelation-part gelled immediately and the rest started to gel after 2 min. | 4 min | Non uniform gelation-part gelled immediately and the rest started to gel after 2 min. | Starts to gel after 2 min. After 4 min a firm, flexible gel is formed. |

The results in Table 2 show a direct correlation between the ionic strength and cross-linking time, wherein the lower ionic strengths in the mTG solution buffer resulted in more rapid cross-linking mTG solutions in sodium acetate buffer cross-linked more rapidly and formed more homogenous gels than those in sodium citrate buffer. Enzyme solutions with sodium citrate buffer cross linked more slowly and formed a non-homogenous gel, probably as a result of the physical gelatin gelation caused by the sodium citrate. However, the gels formed with mTG in sodium citrate are much more flexible and cohesive compared to gels with sodium acetate.

Example 3

Effect of Ionic Strength of Gelatin Buffer Solution on Cross-Linking Time

Materials

The following materials were used in the experiments: 300 bloom type A porcine gelatin [Sigma, St. Louis, Mo.], Sodium Acetate—0.1M Sodium Acetate buffer (pH 6.0), Sodium Acetate—0.25M Sodium Acetate buffer (pH 6.0), Sodium Acetate—0.5M Sodium Acetate buffer (pH 6.0), [Sigma Aldrich] and, 10% Microbial transglutaminase—ACTIVA-TG 10% (10% enzyme, 90% maltodextrin) [Ajinomoto, Japan].

Method

25% (w/w) gelatin in 0.1M sodium acetate buffer (solution A), 25% (w/w) gelatin in 0.25M sodium acetate buffer (solution B), 25% (w/w) gelatin in 0.5M sodium acetate buffer (solution C), 7.5% (w/w) ACTIVA-TG in 0.1M Na—Ac buffer (solution 1 and 7.5% (w/w) ACTIVA-TG 0.25M Na—Ac buffer (solution 2) were prepared.

Results

It was found that raising ion concentration to 0.25-0.5M of gelatin buffer decrease cross-linking time. However, gels did not form when both gelatin buffer and mTG buffer are of high ion concentration. Furthermore, cross-linked gels formed with gelatin solutions in high ion concentration buffer were found to be less thermally stable than gels formed at low ion concentrations.

As illustrated in Tables 3, 4, and 5, increasing ionic strength of gelatin solutions with mTG solutions of 0.1M, decreased cross-linking time hence improving reaction time. No notable differences were observed in formed gels of 0.25M and 0.5M as compared to formed gel of 0.1M Na—Ac.

Increased ionic strength of mTG solutions with increased ionic strength of gelatin solutions provided mechanically weaker cross-linked gels with longer gel forming reaction times.

TABLE 3

Transition temperature examination

| Temperature range, ° C. | Physical state of solution A | Physical state of solution B | Physical state of solution C |
|---|---|---|---|
| 45-46 | liquid | liquid | liquid |
| 40-41 | liquid | liquid | liquid |
| 38-39 | liquid | liquid | liquid |
| 36-37 | liquid | liquid | liquid |
| 34-35 | liquid | liquid | liquid |
| 32-33 | Medium viscosity | Medium viscosity | Medium viscosity |
| 31-32 | High viscosity | High viscosity | Very high viscosity/solid |

TABLE 4

Cross-linking examination - summary of experimental results with mTG solution 1 (0.1M Na—Ac).

| Gelatin solution | Gelation Time (min) | Description of Cross-Linked Gel |
|---|---|---|
| A 0.1M sodium acetate | 0:35 | Minor adhesion and elasticity are noticed in the formed gel. Gel is brittle. After 10 minutes gel is not adhesive or elastic. Brittles fast. |
| B 0.25M sodium acetate | 0:20 | Gel had good adhesion property, but lacks elasticity. After 10 minutes gel remains with good adhesion properties but becomes very brittle. |
| C 0.5M sodium acetate | 0:15 | Formed gel resembles properties of solution B. After 10 minutes formed gel loses adhesion, becomes very brittle and is not elastic. |

TABLE 5

Summary of experimental results with mTG solution 2 (0.25M Na—Ac).

| Gelatin solution | Gelation Time (min) | Description of Cross-Linked Gel |
|---|---|---|
| A 0.1M sodium acetate | 0:25 | Formed gel is soft, with no adhesion properties. Very weak and brittle. After 10 minutes, gel becomes very brittle and does not improve in any mechanical property. |
| B 0.25M sodium acetate | N/A | Gel is semi-liquid and not fully formed for a long period of time (about 2 minutes). Very soft and very weak, and does not improve significantly with time. |
| C 0.5M sodium acetate | N/A | Similar to solution B. Gel appears to be not fully formed for long period of time (about 2 minutes) and only about half of it cross-linked to solid state. Time does not change significantly mechanical properties of the gel. |

Example 4

Effect of Calcium Chloride and Urea on Transition Point

Materials

The following materials were used in the experiments: 300 bloom type A porcine gelatin [Sigma, St. Louis, Mo.], 98% urea [Alfa Aesar, Lancester], Calcium Chloride 97% [Alfa Aesar, Lancester], PBS—Dulbecco's Phosphate Buffered Saline without Calcium and Magnesium [Biological Industries, Israel], Microbial Transglutaminase ACTIVA—WM, 1% enzyme powder in maltodextrin [Ajinomoto, Japan], 10% microbial Transglutaminase—ACTIVA-TG 10% (10% enzyme, 90% maltodextrin) [Ajinomoto, Japan].

Methods

Stock solutions of 5 M Calcium solution, 5 M of Urea solution were prepared. 25% (w/w) gelatin solution, urea and calcium solutions were prepared by diluting urea and calcium stock solutions.
Control A—gelatin was dissolved in PBS
Control Calcium A—gelatin was dissolved in 2 M Calcium.
Control Calcium B—gelatin was dissolved in 1 M calcium.
Solution C—gelatin was dissolved in PBS solution containing 1 M calcium and 2 M urea.
Solution D—gelatin was dissolved in PBS solution containing 1 M calcium and 3 M urea.
Solution E—gelatin was dissolved in PBS solution containing 0.5M calcium and 2M urea.
Solution F—gelatin was dissolved in PBS solution containing 0.5 M calcium and 3 M urea.

Results

As shown in Table 6, urea and calcium had a synergistic effect on reducing the transition point of 25% (w/w) gelatin solutions. 25% (w/w) gelatin solution containing 1 M Calcium chloride combined with 2 M of Urea has a low viscosity at RT. 25% (w/w) gelatin solution containing 0.5 M Calcium chloride and 3 M urea is viscous at RT. Cross linking of gelatin gels containing urea provided weaker gels. The higher the urea concentration, the weaker the gel that was formed. The presence of calcium in the gelatin solutions increased the cross linked gel strength.

TABLE 6

Summary of sol-gel transition results for gelatin gels at 24° C.

| Gelatin Solution | Additives | State at 24° C. | Description |
|---|---|---|---|
| Control | — | Gelled | Clear gel |
| Control Calcium A | 2M Ca | Liquid | Opaque solution |
| Control Calcium B | 1M Ca | Highly viscous | Opaque gel |
| Solution C | 1M Ca 2M urea | Liquid | Opaque solution |
| Solution D | 1M Ca 3M Urea | Liquid | Opaque solution |
| Solution E | 0.5M Ca 2M urea | Highly viscous | Opaque solution |
| Solution F | 0.5M Ca 3M Urea | Slightly Viscous | Opaque solution |

Example 5

Optimization Experiments Done to Determine the Appropriate Amount of Cross-Linker to Use for Each Combination of Gelatin and mTG Solutions Materials The following materials were used in the experiment: Gelita 300 bloom, type A porcine gelatin (Medex, England), Urea 99.5% (Sigma-Aldrich, St. Louis), Calcium Chloride (Alfa Aesar, Lancester), Sodium Acetate trihydrate (Sigma-Aldrich, St. Louis), Acetic Acid 100% (Ridel-De Haen), ACTIVA TG (10% protein, 90% maltodextrin) microbial transglutaminase (Ajinomoto, Japan), Sodium Citrate (Sigma-Aldrich, St. Louis), Citric Acid Monohydrate (Sigma-Aldrich, St. Louis), D-Sorbitol, 97% (Sigma Aldrich St. Louis, Mo.).

Stock Solution Preparation:

2M of Calcium solution was prepared in 0.1 M Na—Ac pH 6.0. The solution was filtrated using number 1 Whatman filter paper.

4M and 5 M urea solutions were prepared in 0.1 M Na—Ac pH 6.0. The solutions were filtered using 250 mL filter system with 22 um cellulose acetate membrane and kept refrigerated.

0.1M Na—Ac solution pH 6.0 was prepared and filtered using 250 mL filter system with 22 um cellulose acetate membrane and kept refrigerated.

2M of Sodium citrate solution was prepared.

2.36M Citric acid solution was prepared.

Gelatin Solution Preparation:

25% (w/w) gelatin solutions were prepared in different additives as follows:
Solution A—in 2 M urea, 1 M CaCl2, 0.1 M Na—Ac pH 6.0.
Solution B—in 4.5 M urea, 0.1 M Na—Ac pH 6.0.

In order to completely dissolve the gelatin powder, the solutions were heated to 50° C. and vigorously stirred. The solution was then passed to 24° C. incubator and kept there overnight (ON) until use.

Microbial Transglutaminase Solutions Preparation:

Microbial transglutaminase (mTG) solutions were prepared, by dissolving mTG (ACTIVA-TG 10%) in different concentrations, in different solutions. The solutions were prepared immediately before use. In order to completely dissolve mTG, the solution had to be vigorously stirred using a plastic rod. The solutions were prepared as follows:

Solution 1—7.5% (w/w) of ACTIVA-TG 10% in 0.1 M Na—Ac
Solution 2—5% (w/w) of ACTIVA-TG 10% in 0.1 M Na-A
Solution 3—6% (w/w) of ACTIVA-TG 10% in 0.1 M Na-A
Solution 4—7% (w/w) of ACTIVA-TG 10% in 0.1 M Na—Ac
Solution 5—5% (w/w) of ACTIVA-TG 10% in 3:1 sorbitol (ratio of dry sorbitol weight to dry gelatin weight) with 0.1M Na—Ac
Solution 6—6.25% (w/w) of ACTIVA-TG 10% in 3:1 sorbitol with 0.1M Na—Ac
Solution 7—7.5% (w/w) of ACTIVA-TG 10% in 3:1 sorbitol with 0.1M Na—Ac
Solution 8—10% (w/w) of ACTIVA-TG 10% in 0.1 M Na-Citrate
Solution 9—12.5% (w/w) of ACTIVA-TG 10% in 0.1 M Na-Citrate
Solution 10—2.5% (w/w) of ACTIVA-TG 10% in 0.1 M Na-Citrate
Solution 11—5% (w/w) of ACTIVA-TG 10% in 0.1 M Na-Citrate
Solution 12—7.5% (w/w) of ACTIVA-TG 10% in 0.1 M Na-Citrate
Solution 13—3% (w/w) of ACTIVA-TG 10% in 0.1 M Na-Citrate
Solution 14—5% (w/w) of ACTIVA-TG 10% in 3:1 sorbitol (sorbitol to gelatin ratio) with 0.5M Na-Citrate
Solution 15—6.25% (w/w) of ACTIVA-TG 10% in 3:1 sorbitol (sorbitol to gelatin ratio) with 0.5M Na-Citrate Viscometer Testing:

Viscometer experiments were conducted according to the procedure described above.

Results

Solutions were examined via viscometer and the optimal enzyme concentration for each gelatin-mTG solution was determined. For each solution, the average temperature throughout the experiment, the time to 30% of the torque and time to 90% of the torque were examined.

FIG. 3 displays the time to viscosities of $3\times10^6$ cP (30% of fully formed gel) and $9\times10^6$ cP (90% of fully formed gel) for the different formulations mentioned above.

Figure 3A:
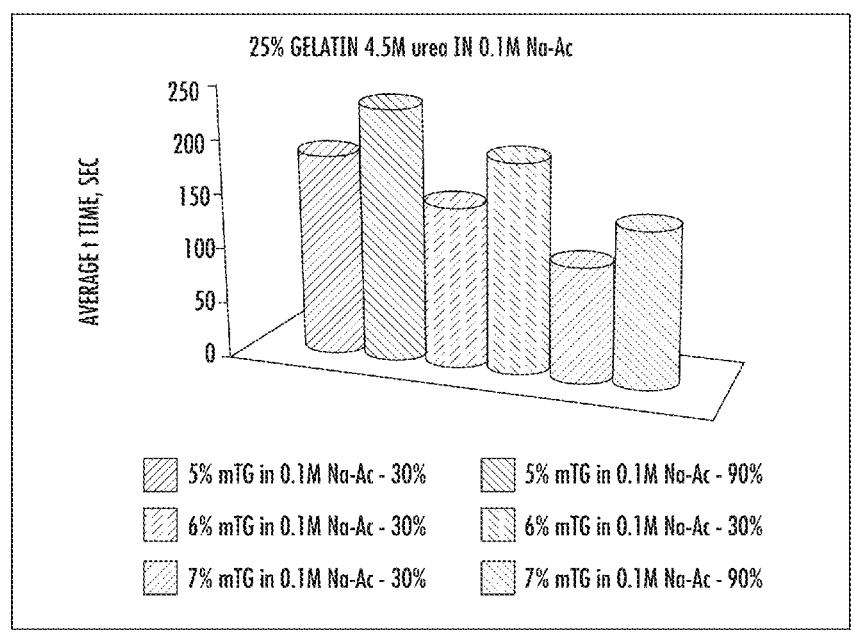
FIG. 3A-F shows the time to viscosities of $3\times10^6$ cP (30% of fully formed gel) and $9\times10^6$ cP (90% of fully formed gel) for different illustrative formulations according to some embodiments of the present invention.

FIG. 3A shows the time to viscosities for the above solutions of 25% gelatin, with 4.5 M urea in 0.1 M Na—Ac. The first two bars relate to the time to 30% and 90% of the torque for a concentration of mTG at 5%; the next two bars relate to the time to 30% and 90% of the torque for a concentration of mTG at 6%; while the last two bars relate to the time to 30% and 90% of the torque for a concentration of mTG at 7%, all respectively. As shown, the time to both 30% and 90% of the torque decreased with increasing concentrations of mTG, showing that increased amounts of mTG increase the rapidity of cross-linking.

Figure 3B:
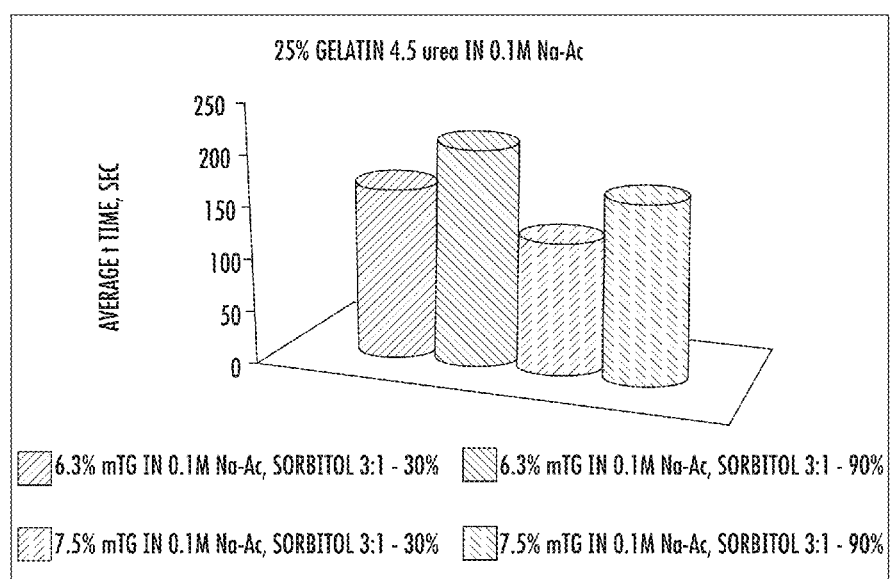

FIG. 3B shows the time to viscosities for the above solutions of 25% gelatin, with 4.5 M urea in 0.1 M Na—Ac, and sorbitol present in a 3:1 ratio of sorbitol:gelatin. The first two bars relate to the time to 30% and 90% of the torque, respectively, for a concentration of mTG at 6.3%, while the last two bars relate to the time to 30% and 90% of the torque, for respectively, for a concentration of mTG at 7.5. Again, the time to both 30% and 90% of the torque decreased with increasing concentrations of mTG.

Figure 3C:
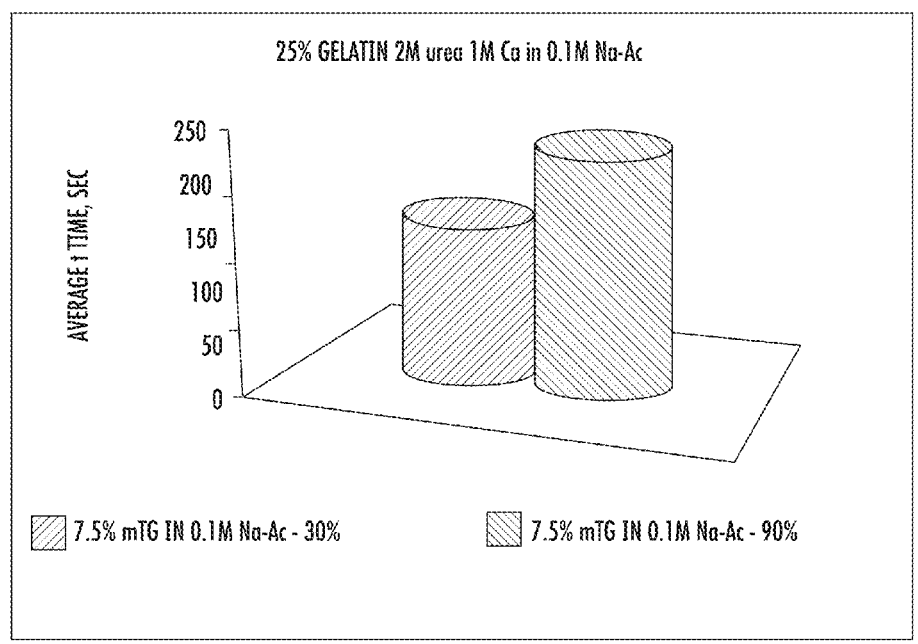

FIG. 3C shows the time to viscosities for the above solutions of 25% gelatin, with 2 M urea and 1 M calcium, in 0.1 M Na—Ac, with a single concentration of mTG at 7.5%. The left bar shows the time to 30% of torque while the right bar shows the time to 90% of torque. Effective cross-linking is also found under these conditions.

Figure 3D:
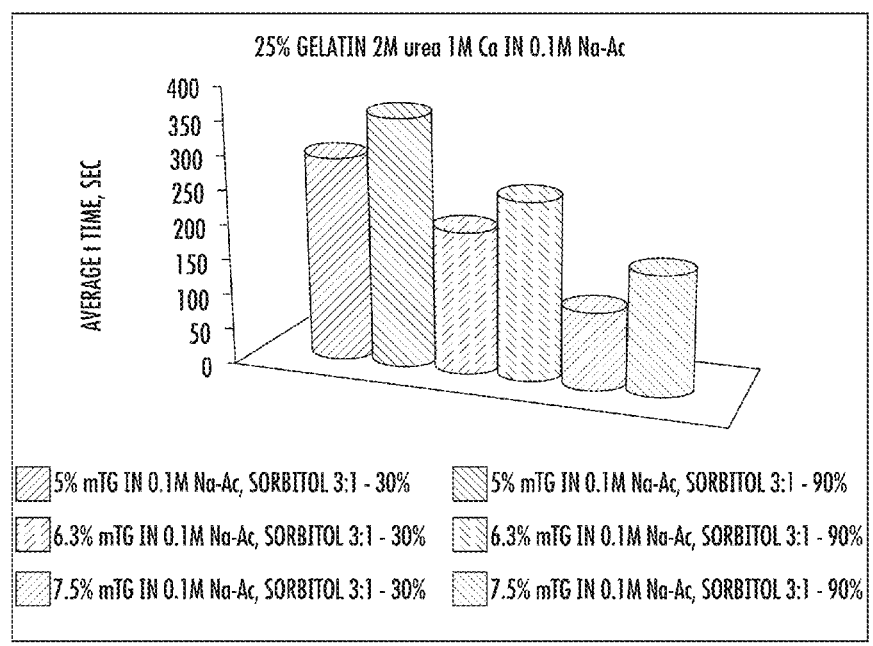

FIG. 3D shows the time to viscosities for the above solutions of 25% gelatin, with 2 M urea and 1 M calcium, in 0.1 M Na—Ac, and sorbitol present in a 3:1 ratio of sorbitol:gelatin. The first two bars relate to the time to 30% and 90% of the torque, respectively, for a concentration of mTG at 5%, the next two bars relate to the time to 30% and 90% of the torque, for respectively, for a concentration of mTG at 6.3% and the last two bars relate to the time to 30% and 90% of the torque, for respectively, for a concentration of mTG at 7.5%. As compared to FIG. 3C, sorbitol has clearly resulted in a greater rapidity of cross-linking, as the time to torque has significantly decreased, although it is still at least somewhat dependent upon the concentration of mTG.

Figure 3E:
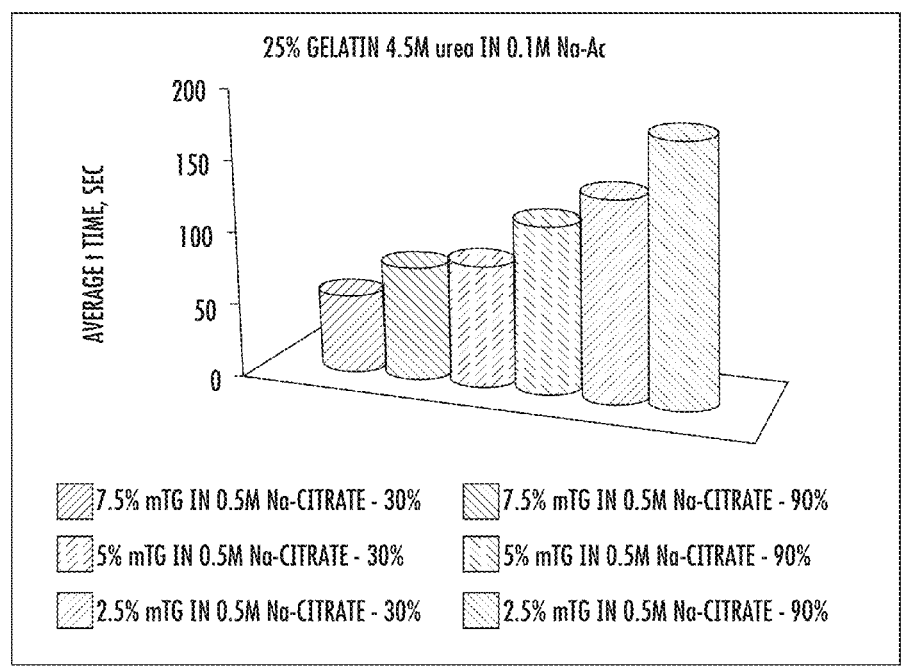

FIG. 3E shows the time to viscosities for the above solutions of 25% gelatin, with 4.5 M urea, where the gelatin solution is in 0.1 M sodium acetate buffer and the mTG is in 0.5 M sodium citrate buffer. The first two bars relate to the time to 30% and 90% of the torque, respectively, for a concentration of mTG at 7.5%, the next two bars relate to the time to 30% and 90% of the torque, respectively, for a concentration of mTG at 5% and the last two bars relate to the time to 30% and 90% of the torque, for respectively, for a concentration of mTG at 2.5%. Increased urea, without calcium, still results in a greater rapidity of cross-linking, as the time to torque has significantly decreased, although it is still at least somewhat dependent upon the concentration of mTG.

Figure 3F:
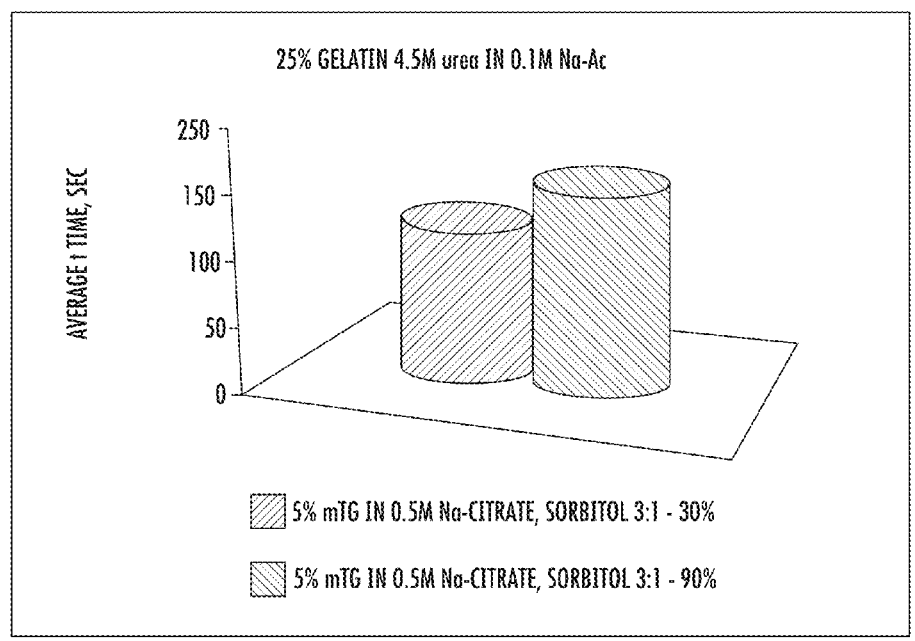

FIG. 3F shows the time to viscosities for the above solutions of 25% gelatin, with 4.5 M urea, in 0.1 M Na—Ac with 0.5 M sodium citrate, with the addition of sorbitol in a 3:1 ratio with gelatin. The two bars relate to the time to 30% and 90% of the torque, respectively, for a concentration of mTG at 5%. Sorbitol appears to decrease the rate of cross-linking and hence the time to torque, whether for 30% or 90%.

Example 6

Effect of Calcium Hydroxide on Protein Solution Transition Point

This Example shows the effect of calcium hydroxide on the sol-gel transition point of gelatin solution. Calcium hydroxide was shown to reduce this transition point.

Materials

The following materials were used in the experiment: 300 bloom, type A porcine gelatin (Gelita, Sioux City), Calcium hydroxide (Sigma-Aldrich, St. Louis), Urea 98% (Alfa Aesar, Lancester), Sodium Acetate trihydrate (Sigma-Aldrich, St. Louis), Acetic Acid (Frutaron, Israel).

Methods

Stock solutions of 0.1M Sodium Acetate buffer pH 6.0, 4 M Urea and 2M Calcium hydroxide were prepared.

The following solutions were prepared:

Control—25% (w/w) Gelatin solution in 0.1M Sodium Acetate
Solution A—25% (w/w) Gelatin in 2M CaOH Solution B—25% (w/w) Gelatin solution in 2M urea 1M CaOH Solution C—25% (w/w) Gelatin solution in 0.5M CaOH All solutions were heated to 50° C. while constant stirring was applied to ensure formation of homogenous solution. After homogenous solution was achieved, all solutions were moved to 22° C. environment. After 2 hours, solutions were manually palpated to assess physical state (liquid or gel).

Results

Solutions A and B were in liquid form at 22° C. while the control solution and solution C were in gel form, indicating that calcium hydroxide can decrease the sol-gel transition point of gelatin solution and that this effect is dose dependant.

Example 7

Effect of Calcium Sequestering Agents on mTG Crosslinking of Gelatin Solutions

The effect on mTG-facilitated cross-linking of gelatin solutions where EDTA or sodium citrate has been added to mTG solutions is described in the below example.

Materials

The following materials were used in the experiments: 300 bloom type A porcine gelatin [Sigma, St. Louis, Mo.], 98% urea [Alfa Aesar, Lancester], Calcium Chloride 97% [Alfa Aesar, Lancester], PBS—Dulbecco's Phosphate Buffered Saline without Calcium and Magnesium [Biological Industries, Israel], Ethylenediaminetetraacetic acid, Sodium Citrate dehydrate 99% [Alfa Aesar, Lancester], Citric acid anhydrous [Frutarom, Israel] Microbial Transglutaminase ACTIVA—WM, 1% enzyme powder in maltodextrin [Ajinomoto, Japan], 10% microbial Transglutaminase—ACTIVA-TG 10% (10% enzyme, 90% maltodextrin) [Ajinomoto, Japan].

Methods

Stock solutions of 5 M Calcium solution, 5 M of Urea solution and, 2 M of EDTA were prepared. 25% (w/w) gelatin solution, urea and calcium solutions were prepared by diluting urea and calcium stock solutions.

Control A—gelatin was dissolved in PBS

Control Calcium A—gelatin was dissolved in 2 M Calcium.

Control Calcium B—gelatin was dissolved in 1 M calcium.

Solution C—gelatin was dissolved in PBS solution containing 1 M calcium and 2 M urea.

Solution D—gelatin was dissolved in PBS solution containing 1 M calcium and 3 M urea.

Solution E—gelatin was dissolved in PBS solution containing 0.5 M calcium and 2 M Solution F—gelatin was dissolved in PBS solution containing 0.5 M calcium and 3 M urea.

Solution G—gelatin was dissolved in PBS solution containing 4 M urea.

0.2% w/w mTG solutions (20% w/w solutions of ACTIVA-WM: 1% mTG, 99% maltodextrin) were prepared as follows:

mTG Control—mTG was dissolved in PBS.

Solution 1—mTG was dissolved in 2 M EDTA solution in PBS. (Note: while dissolving mTG in EDTA, an opaque solution, slightly white colored, was formed. The mTG formed clumps that later dissolved in the solution)

Solution 2—mTG was dissolved in 1.5 M of EDTA solution in PBS.

Solution 3—mTG was dissolved in 0.75 M of EDTA solution in PBS.

Solution 4—mTG was dissolved in a solution containing 2 M sodium citrate.

Solution 5—mTG was dissolved in a solution containing 1 M sodium citrate.

Solution 6—mTG was dissolved in a solution containing 0.5 M of sodium citrate. 1% w/w concentrated mTG solutions (10% w/w solution of ACTIVA-TG: 10% mTG, 90% maltodextrin) solutions were prepared:

Control—Concentrated mTG dissolved in PBS.

Solution 7—Concentrated mTG dissolved in 0.5 M sodium citrate solution.

Results

Tables 7 and 8 below summarize the experimental results for gelatin gels cross linked (CL) with mTG. Table 7 describes gelatin gels cross linked with mTG containing EDTA and Table 8 describes gelatin gels cross linked with mTG containing sodium citrate. The effect of sodium citrate on gelatin solutions is summarized in Table 9.

TABLE 7

Cross linking of gelatin solutions using mTG containing EDTA

| Gelatin Solution | Description- 25% w/w gelatin plus: | Cross linking with mTG | | | | |
|---|---|---|---|---|---|---|
| | | Solution 1 0.2% mTG in 2M EDTA | Solution 2 0.2% mTG in 1.5M EDTA | Solution 3 0.2% mTG in 0.75M EDTA | mTG Control (without EDTA) | 2M EDTA without mTG |
| Control | — | CL immediately, formed a clear, very strong and elastic gel, but not adhesive. | Was not examined | CL immediately formed a clear, strong gel, very elastic but not adhesive. | CL after ~3 min. Formed a clear gel, strong, but not as strong and flexible as with EDTA. Very sticky. | CL immediately. Formed a clear, very strong and elastic gel but not adhesive at all. |
| Control Calcium A | 2M Ca | CL immediately. Formed a white, foamy gel that swelled. A bit sticky. | Was not examined | Was not examined | Weak gel was formed after ~6 min. Sticky. | Was not examined |
| Control Calcium B | 1M Ca | CL immediately. Very foamy, | Was not examined | Immediately partial cross linking was | When examined after 10 | Was not examined |

TABLE 7-continued

Cross linking of gelatin solutions using mTG containing EDTA

| Gelatin Solution | Description- 25% w/w gelatin plus: | Solution 1 0.2% mTG in 2M EDTA | Solution 2 0.2% mTG in 1.5M EDTA | Solution 3 0.2% mTG in 0.75M EDTA | mTG Control (without EDTA) | 2M EDTA without mTG |
|---|---|---|---|---|---|---|
| | | white, non-uniform gel. Strong yet not adhesive. | | observed. Strong gel. | min CL was not observed. | |
| Solution C | 1M Ca 2M urea | CL immediately. Formed white, foamy, swollen gel. Was not sticky. Very strong & flexible. | CL after 20 sec. Non-uniform, white, swollen gel was formed. | CL after 5 min. Created an opaque gel, not so strong as other gels with EDTA. | After 8.5 min weak, opaque gel was formed. Became more adhesive and strong with time. | Immediately CL. White, foamy, strong and flexible gel is formed. The gel is not adhesive. |
| Solution D | 1M Ca 3M Urea | CL immediately. Formed a white, swollen gel. Not so strong gel. | CL immediate, formed a white, foamy gel. Not sticky. | A non-uniform gel is formed immediately. This gel is not foamy. CL completely after >7 min. | After 9.5 min formed a very weak, opaque gel. | Was not examined. |
| Solution E | 0.5M Ca 2M urea | CL immediately. Formed a white, fluffy gel. Less foamy than gels formed with 1M EDTA and weaker. | Foams immediately. Starts to CL only after 3 min. A weak gel was formed. | After ~8 min a weak gel was formed, opaque but not foamy. | CL after 4 min. Formed a weak gel. | Was not examined |
| Solution F | 0.5M Ca 3M Urea | CL immediately. White, swollen gel is formed. Not as foamy or strong as with 1M Ca. | Immediately CL. Not as foamy or white as with 2M EDTS | A non uniform gel is formed after 6 min. Very weak. Not as foamy as with 1.5M EDTA. | CL after 3.5 min. Formed an opaque sticky gel. The gel is weak. | Was not examined |

TABLE 8

Cross linking of gelatin solutions using mTG containing Sodium citrate

| Solution | Description- 25% w/w gelatin plus: | Solution 4 0.2% mTG in 2M Sodium citrate | Solution 5 0.2% mTG in 1M Sodium citrate | 2M Sodium Citrate without mTG |
|---|---|---|---|---|
| Control | 25% gelatin | CL immediately. Formed a strong and flexible gel that in not adhesive. After heating above 40° C. partially reversed. | After ~30 sec. a non-uniform gel is formed. The gel is not so strong or sticky gel. When heated to 37° C.- did not reverse. | CL immediately, forming a strong, flexible gel. Not sticky. When heated to 37° C.- did not reverse. |
| Control Calcium A | 2M Ca | Was not examined | CL immediately, forming a white fluffy gel. | Was not examined |
| Control Calcium B | 1M Ca | Was not examined | Was not examined | Was not examined |
| Solution C | 1M Ca 2M urea | Immediately formed a white, swollen gel. Very | Was not examined | Immediately CL. White, foamy, strong and flexible gel is |

TABLE 8-continued

Cross linking of gelatin solutions using mTG containing Sodium citrate

| | | Cross linking with mTG | | |
|---|---|---|---|---|
| Solution | Description-25% w/w gelatin plus: | Solution 4 0.2% mTG in 2M Sodium citrate | Solution 5 0.2% mTG in 1M Sodium citrate | 2M Sodium Citrate without mTG |
| | | strong and flexible. Not adhesive. A bit non-uniform and more brittle than without the enzyme. | | formed. The gel is not adhesive. |
| Solution D | 1M Ca 3M Urea | Was not examined | Was not examined | Was not examined. |
| Solution E | 0.5M Ca 2M urea | Was not examined | Was not examined | Was not examined |
| Solution F | 0.5M Ca 3M Urea | Was not examined | Was not examined | Was not examined |

TABLE 9

Cross linking of gelatin solutions using mTG solutions containing sodium citrate

| mTG solution | Control A (25% (w/w) gelatin solution in PBS) | Solution C ((25% (w/w) gelatin in 2M urea, 1M Ca and PBS) | Solution G (25% (w/w) gelatin in 4M urea and PBS) |
|---|---|---|---|
| Conc. mTG control (1% (w/w) conc. mTG solution in PBS) | CL within 1 min. Formed a sticky gel. Gel is quite brittle. | CL within 2 min. Formed a very slimy, sticky, weak and soft gel that is very brittle. | CL within 2 min. formed a very soft, flexible weak gel. After 13 min the gel appears to be stronger and still flexible, yet brittle. |
| Conc. mTG Solution 7 (1% (w/w) conc. mTG solution in 0.5M sodium citrate) | Immediate CL. Very brittle gel is formed. | Immediately formed a very flexible, sticky gel after 1.5 mi. After 10 min the gel is very strong, flexible and sticky. With time becomes brittle | CL after 1.5 min. Formed a very brittle and weak. Yet sticky gel. |
| mTG solution 6 (0.2% (w/w) mTG solution in 0.5M sodium citrate) | CL after 30 sec. Formed a very strong and flexible gel, yet not sticky at all. | CL within 10 min. Formed a very weak, non-uniform, flexible gel. | Was not examined. |

As shown in the Tables above, EDTA physically cross linked gelatin solutions. High concentrations of EDTA (0.75-2 M) immediately cross linked gelatin solutions. Gelatin gels cross linked with EDTA were not adhesive. EDTA formed very strong and flexible gels when mixed with gelatin. The higher the EDTA concentration, the stronger the gel that was formed. At moderate EDTA concentrations (0.5-0.75 M), non-homogenous cross linking occurred. This was probably due to insufficient blending of the reagents. At lower EDTA concentrations (below 0.5 M), physical cross linking of gelatin solutions was not observed and the gelatin became slightly viscous. Cross linking of gelatin solutions with mTG solutions containing EDTA created strong flexible gels that were adhesive.

Sodium citrate physically cross-linked 25% (w/w) gelatin solutions. The formed gels were stable at 37° C. Sodium citrate formed highly flexible, strong gels that were not adhesive. 1M and 2M sodium citrate solutions immediately cross linked 25% (w/w) gelatin solutions with or without additives. Sodium citrate solutions at concentrations ranging between 0.5-0.75M immediately cross linked gelatin without additives. However, gelatin solutions containing urea became only viscous. According to the experiments presented herein, using sodium citrate solutions at concentrations ranging from 0.1M to 0.5M, did not result in physical gelation. Above these concentrations, the higher the sodium citrate concentration, the stronger the gel that was formed. The results suggest the use of sodium citrate as a cross linking agent for gelatin solutions, with or without the presence of mTG. The stability of the formed gels at 37° C. suggests that theses gels can be used for in situ crosslinking in the body cavity for applications such as surgical sealing. Since sodium citrate does not appear to form adhesive gels with gelatin, the combination of sodium citrate and mTG may be preferred or considered. Gelatin solutions cross linked with mTG solutions containing 0.5M sodium citrate form highly flexible, strong and adhesive gels.

Example 8

Effect of Calgon on mTG Crosslinking of Gelatin Solutions

As used herein, the term "Calgon" refers to amorphous sodium polyphosphate, such as for example sodium hexametaphosphate.

Materials

The following materials were used: 300 bloom, type A porcine gelatin [Sigma, St. Louis, Mo.], 98% urea [Alfa Aesar, Lancester], 0.1M Sodium Acetate buffer (pH 6.1) was prepared as previously described, 0.5M Sodium Citrate dehydrate 99% [Alfa Aesar, Lancester], Calcium Chloride 97%, dried powder [Alfa Aesar, Lancester], Calgon [Global Environmental Solutions, INC], 10% microbial Transglutaminase—ACTIVA-TG 10% (10% enzyme, 90% maltodextrin) [Ajinomoto, Japan].

A 4M urea stock solution in sodium acetate and a 4M stock solution of calcium chloride solution were prepared.

Methods

The following control and experimental solutions were prepared:
Gelatin Solution A, 25% (w/w) gelatin with 4M urea
Gelatin solution B, 25% (w/w) gelatin with 2M Ca Cl$_2$
Gelatin solution C, 25% (w/w) gelatin with 2M urea 1M CaCl$_2$.
Gelatin solution D, 25% (w/w) gelatin with 2M urea 2M CaCl$_2$.
mTG solution 1, 0.5% mTG-5% (w/w) ACTIVA-TG 10% in 0.1M Na—Ac buffer
mTG solution 2, 0.5% mTG-5% (w/w) ACTIVA-TG 10% with 10% wt Calgon
mTG solution 3, 0.5% mTG-5% (w/w) ACTIVA-TG 10% with 5% wt Calgon
mTG solution 4, 1.0% mTG-10% (w/w) ACTIVA-TG 10% with 5% wt Calgon
mTG solution 5, 2.0% mTG-20% (w/w) ACTIVA-TG 10% with 5% wt Calgon
mTG solution 6, 1.0% mTG-10% (w/w) ACTIVA-TG 10% with 5% wt Calgon in 0.1M sodium acetate buffer.
mTG solution 7, 1.0% mTG-10% (w/w) ACTIVA-TG 10% with 5% wt Calgon in 0.5M sodium citrate buffer.

Gel properties of gels formed by mixture of different gelatin solutions with different mTG solutions were subjectively tested by thoroughly mixing 2 mL of gelatin solution with 1 mL of mTG solution. Gelation time was then tracked by assessing gelation time as the time at which the entire gelatin mass formed a coherent solid gel.

Results

Initial tests of the use of Calgon proved to mildly decrease cross-linking time of control solutions with no calcium. However, no improved mechanical properties were noted. Calgon resulted in the creation of extremely adhesive and elastic gels but also proved to increase significantly cross-linking time with solutions that did contain calcium additives. Furthermore, it seems that Calgon works better with lower concentrations as 5% wt Calgon solutions yielded better and faster gels than equivalent 10% wt Calgon solutions.

TABLE 10

Gelation time and description of cross-linked gel

| Composition # | 25% Gelatin solution plus: | mTG solution | Gelation Time (min) | Description of Cross-Linked Gel |
|---|---|---|---|---|
| A1 | A<br>4M urea | 1<br>0.5% mTG<br>in 0.1M NaAC | 1:10 | Gel is rather adhesive. Some elasticity is noticed. Very weak gel. After 10 minutes gel is still somewhat adhesive, not very elastic and becomes brittle. |
| A2 | A<br>4M urea | 2<br>0.5% mTG<br>10% Calgon | 0:50 | Gel is slightly stronger than 1 + A. Same adhesive property. After 10 minutes still somewhat adhesive and becomes more elastic than composition 1A. Becomes brittle. |
| B1 | B<br>2M CaCl$_2$ | 1<br>0.5% mTG<br>In 0.1M NaAC | 1:55 | Formed gel is adhesive and weak. After 10 minutes still posses good adhesive properties, but becomes brittle in a similar way to composition 1A. |
| B2 | B<br>2M CaCl$_2$ | 2<br>0.5% mTG<br>10% Calgon | — | After 10 minutes, mixture of the two solutions still remains in a liquid state. Color of the mixture is significantly other than other above mixtures. After 50 minutes (no in-between examinations were taken) the formed mixture posses great adhesive and elastic properties although it is not yet solid (very high viscous state). |

TABLE 10-continued

Gelation time and description of cross-linked gel

| Composition # | 25% Gelatin solution plus: | mTG solution | Gelation Time (min) | Description of Cross-Linked Gel |
|---|---|---|---|---|
| B3 | B<br>2M CaCl$_2$ | 3<br>0.5% mTG<br>5% Calgon | — | After 10 minutes, mixture of the two solutions still remains in a liquid state. Color of the mixture is significantly other than other above mixtures. After 50 minutes (no in-between examinations were taken) the formed gel posses great adhesive and elastic properties. It is also quite strong. |
| B4 | B<br>2M CaCl$_2$ | 4<br>1.0% mTG<br>5% Calgon | 6:00 | Formed gel is not completely solid (very high viscous state). After 20 minutes formed gel is very strong, very adhesive and very elastic. |
| B5 | B<br>2M CaCl$_2$ | 5<br>2.0% mTG<br>5% Calgon | 2:00 | Formed gel is not completely solid (very high viscous state). After 10 minutes the gel is very adhesive, very elastic and strong. Gel becomes brittle only after 20 minutes, and still remains very adhesive and elastic. |

In further tests, Calgon helped to create extremely adhesive and elastic gels but also significantly increased cross-linking time in solutions that contained calcium additives. It should be noted that the mechanical properties (adhesion, elasticity, strength) of gels formed with Calgon were retained for a long period of time (45+ minutes), and improved with time progression. Use of 10% w/w mTG solutions with 5% wt calgon, either in 0.1M sodium acetate or 0.5M sodium citrate, resulted in a shorter cross-linking time (faster reaction) for 25% w/w gelatin in 2M urea 1M Ca when compared with 25% w/w gelatin in 2M urea 2M Ca. 25% w/w gelatin in 2M urea 2M Ca solution formed cross-linked gel faster with mTG solutions in 0.1M Na—Ac compared to mTG solutions in 0.5M Na-Citrate.

TABLE 11

Gelation time and description of cross-linked gel

| Composition # | 25% Gelatin solution plus | mTG solution | Gelation Time (min) | Description of Cross-Linked Gel |
|---|---|---|---|---|
| A6 | A<br>4M urea | 6<br>1.0% mTG<br>5% Calgon<br>0.1M NaAc | 0:35 | Form cross-linked gel is adhesive, elastic and weak. Possess low flexibility. After 10 minutes gel becomes less adhesive, remains weak and not very elastic and becomes quite brittle. |
| B6 | B<br>2M CaCl$_2$ | 6<br>1.0% mTG<br>5% Calgon<br>0.1M NaAc | N/A | No cross-linking was observed, even after 45 minutes. |
| C6 | C<br>2M urea<br>1M CaCl$_2$ | 6<br>1.0% mTG<br>5% Calgon<br>0.1M NaAc | 3:20 | Gel is very adhesive, very weak and in a semi-liquid state. After 10 minutes gel remains very much adhesive, becomes notably stronger, and is elastic. After 20 minutes cross-linked gel remains very adhesive, strong and elastic though it is starts to become "brittle" (unlike solution B1, gel is torn apart when force is applied instead of break apart) |

TABLE 11-continued

Gelation time and description of cross-linked gel

| Composition # | 25% Gelatin solution plus | mTG solution | Gelation Time (min) | Description of Cross-Linked Gel |
|---|---|---|---|---|
| D6 | D<br>2M urea<br>2M CaCl$_2$ | 6<br>1.0% mTG<br>5% Calgon<br>0.1M NaAc | 7:30 | After 30 minutes no notably changes in the gel properties.<br>After 45 minutes gel is still very adhesive and elastic. Although it is quite strong, it is also "brittle".<br>Formed gel is very adhesive and very weak. The gel is less formed compared to gel from solution B3 as it looks quite liquid.<br>After 10 minutes a better formed gel is achieved, although semi-liquid state still remains. Gel is very adhesive, weak and "sticky".<br>After 20 minutes still remains very weak semi-formed gel, with some elasticity properties. |
| A7 | A<br>4M urea | 7<br>1.0% mTG<br>5% Calgon<br>0.5M citrate | 0:20 | Gel is weak, somewhat adhesive.<br>After 10 minutes gel becomes brittle. |
| B7 | B<br>2M CaCl$_2$ | 7<br>1.0% mTG<br>5% Calgon<br>0.5M citrate | N/A | No cross-linking was observed, even after 45 minutes. |
| C7 | C<br>2M urea<br>1M CaCl$_2$ | 7<br>1.0% mTG<br>5% Calgon<br>0.5M citrate | 1:45 | Cross-linked gel is elastic, flexible and very adhesive. Although the gel is not very strong, it is much better than gel achieved from 3B and is not in a semi-liquid state.<br>After 10 minutes gel remains very adhesive. It is also possess good elasticity and flexibility properties.<br>After 20 minutes gel remains very adhesive, elastic and flexible. Although it is quite strong, the gel is tear apart when force is applied (like in composition 3B).<br>After 30 minutes gel appears to be stronger than before and still very adhesive, elastic and flexible.<br>After 45 minutes remains very adhesive, quite flexible and elastic. Gel feels somewhat weaker. |
| D7 | D<br>2M urea<br>2M CaCl$_2$ | 7<br>1.0% mTG<br>5% Calgon<br>0.5M citrate | 13:10 | Gel is extremely weak and it appears that besides being adhesive, possess no other notably mechanical properties.<br>After 10 minutes, gel is very weak, soft and very adhesive.<br>After 20 minutes, gel is much stronger and is very adhesive, elastics and flexible.<br>After 30 minutes no notable changes in the gel properties.<br>After 45 minutes gel it appears that the gel become much stronger than before, and is more adhesive and elastic than formed gel from solution B3. As before, gel is torn apart (and not "brittle") when force is applied. |

Example 9

Use of Urease to to Reverse Sol-Gel Transition Point Lowering Effect of Urea Materials The following materials were used in the experiment: Gelita 275 bloom, type A porcine gelatin (Gelita, Sioux City), 98% urea (Alfa Aesar, Lancester), Sodium Acetate trihydrate (Sigma-Aldrich, St. Louis), Acetic Acid 100% (Ridel-De Haen), Urease Type III: from Jack Beans (Sigma-Aldrich, St. Louis).

Methods

Stock solutions of 0.1M Sodium Acetate buffer pH 6.0, and 4.5M Urea solution were prepared.

25% w/w gelatin solution in 0.1M Sodium Acetate (Solution A) and 25% (w/w) Gelatin solution with 4.5M urea, 0.1M Sodium Acetate (Solution B) were prepared.

After homogenous solutions were achieved, half of the solution B was moved to another beaker (solution C) in which 0.125 g urease (5000 units) was added and constant stirring was applied. Solutions A, B, and C were then transferred to a 22° C. environment.

Results

After 60 minutes at 22° C., it was found that while solution B remained in viscous liquid form, solution C and A reverted to gel form.

These results indicate that urease reverses the sol-gel transition point lowering effect of urea addition to a gelatin solution.

Example 10

Effect of Sorbitol on Crosslinked Gel Flexibility

Effect of Sorbitol on Accelerating mTG Crosslinking Reaction

Materials

The following materials were used: Gelatin—300 bloom, type A porcine gelatin. [Sigma, St. Louis, Mo.], 98% urea [Alfa Aesar, Lancester], 0.1M Sodium Acetate buffer (pH 6.1), Calcium chloride 97% [Alfa Aesar, Lancester], Sodium citrate dehydrate 99% [Alfa Aesar, Lancester], Citric acid anhydrous [Frutarom, Israel], 10% microbial Transglutaminase—ACTIVA-TG 10% (10% enzyme, 90% maltodextrin) [Ajinomoto, Japan].

Methods

The following solutions were prepared: 4M urea solution in Na—Ac, 4 M of Calcium solution, 2 M of Sodium Citrate solution was prepared, 0.5M Sodium Citrate was prepared.
Gelatin Solution A—25% (w/w) gelatin with 4M urea.
Gelatin solution B—25% (w/w) gelatin with 2M urea and 1M Ca
mTG solution 1—0.5% w/w mTG solution (5% (w/w) ACTIVA-TG solution) with 1:1 (w/w) (with respect to dry gelatin weight in gelatin solutions) sorbitol and 0.5M Na-Citrate
mTG solution 2—0.5% w/w mTG solution (5% (w/w) ACTIVA-TG solution) with 2:1 (w/w) (with respect to dry gelatin weight in gelatin solutions) sorbitol and 0.5M Na-Citrate
mTG solution 3—0.5% w/w mTG solution (5% (w/w) ACTIVA-TG solution) with 3:1 (w/w) (with respect to dry gelatin weight in gelatin solutions) sorbitol and 0.5M Na-Citrate.

Results

The experimental data in this experimental example confirmed that sorbitol further enhances the flexibility of gels prepared with mTG in sodium citrate buffer.

As illustrated in Tables 12-14, the use of sorbitol and sodium citrate in mTG solutions proved to yield fairly flexible gels, both with 25% (w/w) gelatin in 4M urea and 25% (w/w) gelatin in 2M urea and 1M $CaCl_2$. Thus, it may be that sorbitol serves to enhance flexibility property as well as to maintain mTG activity. It was also found that increasing sorbitol concentration leads to a faster cross-linking reaction.

TABLE 12

Cross-linking with 0.5% mTG (5% ACTIVA-TG 10%), 1:1 (w/w) sorbitol to gelatin ratio and 0.5M Na

| Solution | State at 24° C. | Gelation Time (min) | Description of Cross-Linked Gel |
|---|---|---|---|
| A 25% gelatin 4M urea | Low viscous | 0:50 | Quite adhesive gel. Gel appears to be quite elastic, flexible and strong. After 10 minutes, gel remains fairly adhesive, elastic and flexible although it becomes brittle as time progress. |
| B 25% gelatin 2M urea 1M $CaCl_2$ | Liquid | 1:55 | The cross-linked gel is adhesive and is more elastic and flexible than gel 1, although it appears to be quite weak. After 10 minutes gel remains adhesive and elastic and becomes stronger. |

TABLE 13

Cross-linking with 0.5% mTG (5% ACTIVA-TG 10%), 2:1 (w/w) sorbitol to gelatin ratio and 0.5M Na

| Solution | State at 24° C. | Gelation Time (min) | Description of Cross-Linked Gel |
|---|---|---|---|
| A 25% gelatin 4M urea | Liquid | 0:35 | Much more adhesive gel than the earlier gel (with 1:1 w/w sorbitol). Quite elastic and strong. After 10 minutes remains quite adhesive and flexible, but appears to be weaker and becomes brittle. |
| B 25% gelatin 2M urea 1M $CaCl_2$ | Liquid | 1:20 | Very adhesive. Quite elastic, flexible and weak. After 10 minutes still posses good adhesive properties. Gel is quite elastic and flexible and fairly strong. |

TABLE 14

Cross-linking with 0.5% mTG (5% ACTIVA-TG 10%), 3:1 (w/w) sorbitol to gelatin ratio and 0.5M sodium citrate

| Solution | State at 24° C. | Gelation Time (min) | Description of Cross-Linked Gel |
|---|---|---|---|
| A 25% gelatin 4M urea | Liquid | 0:25 | Adhesive gel. Very weak at first, and semi liquid (though clearly noticed as gel). After 10 minutes remains with the same adhesive properties and gains some mechanical strength. Gel is more elastic and flexibile. |
| B 25% gelatin 2M urea | Liquid | 0:50 | Very adhesive gel. Somewhat elastic and, just like gel 1, appears to be in a semi liquid stat. After 10 minutes remains very much |

TABLE 14-continued

Cross-linking with 0.5% mTG (5% ACTIVA-TG 10%), 3:1 (w/w) sorbitol to gelatin ratio and 0.5M sodium citrate

| Solution | State at 24° C. | Gelation Time (min) | Description of Cross-Linked Gel |
|---|---|---|---|
| 1M CaCl$_2$ | | | adhesive and become stronger, and more elastic and flexible. Hard to tell if this gel is better than the earlier test of 2 (with 2:1 w/w sorbitol). |

Example 11

Gum Arabic, Guar Gum, PVA, PEG 6000 and Polyvinylpyrrolidone (PVP) as Plasticizers Gum Arabic, Guar Gum, Polyvinyl Alcohol (PVA), Polyethylene Glycol (PEG) 6000, and PVP are plasticizers that can act as spacers in a solution into which they are dissolved. This example demonstrates that these plasticizers can be added to a crosslinker solution that is used to crosslink a protein solution to improve the flexibility of the crosslinked protein solution.

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), ACTIVA TG (10% protein, 90% maltodextrin. Ajinomoto, Japan), Sodium Citrate (Sigma-Aldrich, St. Louis), Citric Acid Monohydrate (Sigma-Aldrich, St. Louis), Sodium Chloride (Frutarom, Israel), Gum Arabic (Sigma-Aldrich, St. Louis), PVA (Merck; Darmstadt, Germany), PEG6000 (Fluka; St. Louis, Mo.), Guar Gum (Sigma-Aldrich; St. Louis, Mo.), PVP in the form of Plasdone K-90 (ISP Technologies Inc.; Texas City, Tex.).

The following stock solutions were prepared: 0.1M Na—Ac solution pH 6.0, 0.4M Na-Citrate solution pH 6.0, 4.5M urea in 0.1 Na—Ac solution, 2M CaCl2 stock solution in 0.1M Na—Ac pH 6.0, 40% w/v Arabic gum solution in WFI, 5% w/v Guar gum solution in WFI, 20% w/w PVP solution in WFI, 5% w/v PVA solution in WFI, 5% w/v Guar gum solution in WFI, 10% w/v PEG 6000 in WFI.

Gelatin solutions of 12.5% w/w (solution A) and 25% w/w (solution B) were prepared in buffer of 3.8M Urea, 0.15M CaCl2 and 0.1M Na—Ac.

mTG powder solutions of 0.375% w/w (solution 1) and 0.5% w/w (solution 2) were prepared by dissolving Activa TG (10% mTG, 90% maltodextrin) in 0.4M Na-Citrate.

Methods

Aliquots of 0.375% mTG solution (solution 1) were mixed with each stock plasticizer solution at a volumetric ratio of 1:1. If the required concentration of plasticizer was lower than half the stock solution, the plasticizer was diluted prior to mixing with the mTG solution. For each type of mTG-plasticizer solution, 10 mL of the solution was thoroughly mixed with 20 mL of gelatin solution A and poured into a 100 mL beaker.

The gelatin-mTG-plasticizer plug formed by the 30 mL of material in the 100 mL beaker was removed from the beaker within 10 minutes following mixture of the solutions. Each plug was then stored in physiological saline for 24 hours at room temperature.

Following the 24 hour storage period, each plug was palpated by a blind tester who judged the flexibility of the plug on a scale of 1-3 (+, ++, or ++). The flexibility mark for each type of plug was recorded.

Results

The control gel (no plasticizer) was marked as the baseline flexibility (+) and the other plasticizer groups received marks indicating a noticeable increase in the flexibility of the gel, as indicated in the below table:

TABLE 15

Elasticity of formed gelatin gel as function of plasticizer component

| | Conc. In mTG | Ratio polymer/gelatin | Condition of Gel after 24 hr in Saline |
|---|---|---|---|
| Control | — | — | + |
| | — | — | + |
| | — | — | + |
| Gum Arabic | 5% | 10.1% | ++ |
| | 20% | 40.1% | +++ |
| Guar Gum | 0.5% | 1% | ++ |
| PVA | 1.25% | 2.5% | ++ |
| | 2.5% | 5% | ++ |
| PEG 6000 | 2.5% | 5% | ++ |
| | 5% | 10% | ++ |

Example 12

Effect of Concentration of an mTG Solution on Gelling Time

Materials & Methods

An mTG solution was prepared by dissolving 10% (w/w) mTG powder into 0.1M sodium acetate buffer. mTG used was ACTIVA WM (Ajinomoto, Japan), comprised of 99% maltodextrin and 1% protein. The volume of each mTG solution was concentrated to the indicated factor using a 50 kDa ultrafiltration cartridge to remove the carrier materials and buffer.

Separately, gelatin solution containing 20% (w/w) type A, 300 bloom gelatin in 0.1M sodium acetate buffer of pH 6.0 was prepared.

After mTG solutions were concentrated, aliquot of each mTG solution were added to aliquots of gelatin solution at a volumetric ratio of 1:2, mTG solution:gelatin solution. This mixture was then thoroughly mixed. Mixed composition was subject to inversion in a tube every 30 seconds and gelling time was defined as time at which composition ceased to flow.

Results

Table 16 shows the effect of concentration of mTG solution on gelling time.

TABLE 16

Effect of concentration of mTG solution on gelling time

| mTG | Concentration factor | Gelling time (min) |
|---|---|---|
| No treatment | — | 6 |
| After membrane pretreatment with 0.45μ | — | 7 |
| After concentration | 1.5 | 4 |
| After concentration | 2 | 3 |
| After concentration | 3 | 2 |

Example 13

Microbial Transglutaminase (mTG) Purification Process

This example relates to a microbial transglutaminase (mTG) purification process that purifies a mTG product, which in this non-limiting example is food-grade, to produce an mTG composition with specific activity >25 enzyme units per milligram, >95% electrophoretic purity, <5 endotoxin units per gram, and <10 CFU/g.

Food grade mTG product (Activa™ TG; Ajinomoto, Japan) was used as a starting raw material. The initial characteristics of this mTG product were as shown in Table 17:

TABLE 17

| mTG initial characteristics | |
|---|---|
| Tests | Specifications |
| M.W.(SDS-Coomassie) | 38 kDa ± 2 kDa |
| SDS-PAGE (Coomassie) | >95% |
| Specific activity | 11.4 U/mg, Bradford |

This food grade product was processed with the below-described purification process scheme:

TABLE 18

| Process scheme for mTG purification: | |
|---|---|
| Step | Details |
| Dissolution | 1700 g of mTG powder at concentration of 7.5% w/w in buffer (50 mM NaAc pH 5.5), high stirring rate for 1 hour at room temperature. |
| Filtration | Coarse filtration with medical bandage to remove aggregates. |
| Clarification | Ultrafiltration (UF) with pore size of 0.65µ; Filtrate was collected |
| SP-FF chromatography | 24 ml column Equilibration: 50 mM NaAc pH 5.5 Load: post clarification fraction Wash: 50 mM NaAc, 50 mM NaCl pH 5.5 Elution: 50 mM NaAc, 150 mM NaCl pH 5.5 |
| Concentration and dialysis | 10 kDa cutoff Buffer change to 0.2M citrate pH 6.0 |

The resulting, purified mTG solution was as follows, as shown in Table 19A:

TABLE 19A

| Tests | Specifications |
|---|---|
| M.W.(SDS-Coomassie) | 38 kDa ± 2 kDa |
| SDS-PAGE (Coomassie) | >95% |
| Specific activity | 26.3 U/mg |
| LAL-endotoxins | <0.15 EU/g mTG solution |
| AMC | <10 CFU/ml mTG solution |

Figure 4:
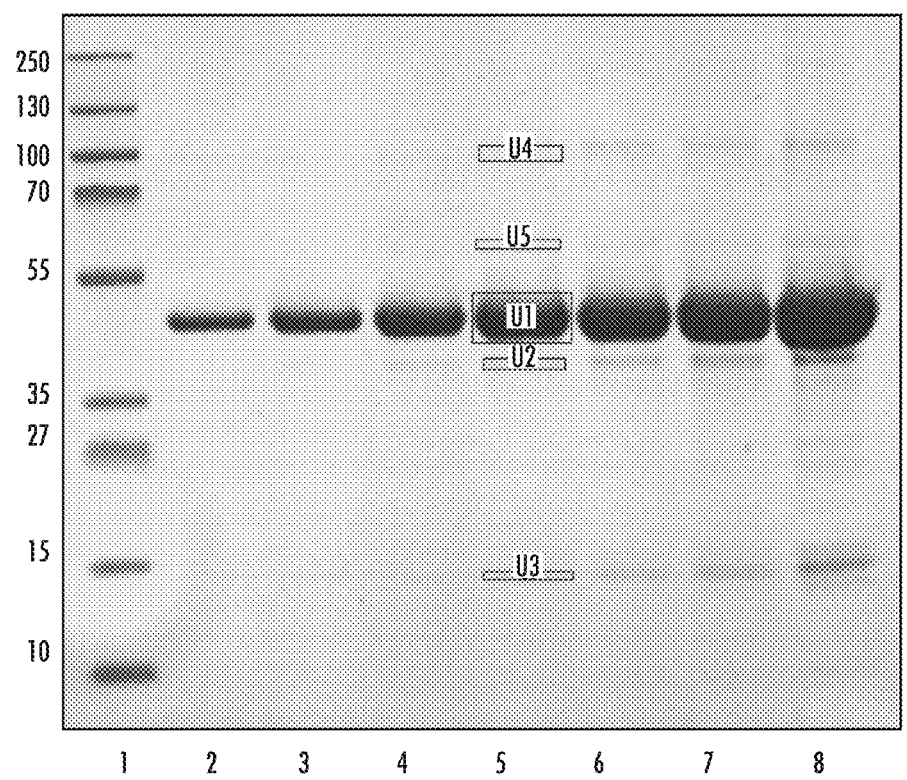
FIG. 4 shows the results of gel electrophoresis of the purified mTG material (lanes 2-8)

FIG. 4 shows the results of gel electrophoresis of the purified material (lanes 2-8). Each lane was loaded with a different amount of purified mTG, ranging from 1-20 µg, as shown in Table 19B:

TABLE 19B

| Lane | µg loaded | Adj. Vol. ODu * mm2 |
|---|---|---|
| 2 | 1 | 99.82786 |
| 3 | 2 | 150.1723 |
| 4 | 4 | 216.5421 |
| 5 | 6 | 286.3214 |
| 6 | 8 | 316.2235 |
| 7 | 10 | 366.3012 |
| 8 | 20 | 486.6132 |

The molecular weight standards are shown in lane 1, with molecular weights as given. Purified mTG is represented by the major band at about 38 kd. The bands for 6 micrograms of of protein (lane 5) underwent densitometric analysis since densitometric linearity was not calculated at loading amounts above 6 µg. The results are shown in Table 20 below.

TABLE 20

| Densitometric analysis results | | | |
|---|---|---|---|
| Band | Adj. vol ODu * mm2 | Net. Vol. | % of total |
| U1 | 338.288622 | 334.749 | 95.9354 |
| U2 | 13.697427 | 5.34658 | 1.53227 |
| U3 | 12.8509144 | 4.97192 | 1.4249 |
| U4 | 15.7683192 | 2.99658 | 0.85879 |
| U5 | 9.03115586 | 0.86754 | 0.24863 |

The results in Table 20 above show that main band density contains ~95.9% of total proteins in the sample. This purification process demonstrates that it is possible to purify food grade mTG into a mTG composition that is more suitable for medical use.

Example 14

Use of Alginate Ester, Gum Arabic, Carboxymethyl Cellulose (CMC), Xanthan Gum, Guar Gum, PVP to Increase Viscosity of Crosslinker Material Solution Alginate Ester, Gum Arabic, Carboxymethyl cellulose (CMC), Xanthan Gum, Guar Gum, and PVP are well known viscofiers that increase the viscosity of solution into which they are dissolved. This example demonstrates that these viscofiers can be added to a crosslinker solution that is used to crosslink a protein solution without inhibiting the crosslinking rate that results in gelation of the protein solution by more than 50%. Even more surprisingly, some of these viscofiers accelerate the gelation speed.

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), ACTIVA TG (10% protein, 90% maltodextrin. Ajinomoto, Japan), Sodium Citrate (Sigma-Aldrich, St. Louis), Citric Acid Monohydrate (Sigma-Aldrich, St. Louis), Sodium Chloride (Frutarom, Israel), Alginate Ester (Sigma-Aldrich; St. Louis, Mo.), Gum Arabic (Sigma-Aldrich, St. Louis), Carboxymethyl Cellulose (high and medium viscosity, Sigma-Aldrich; St. Louis, Mo.), Xanthan gum (Sigma-Aldrich, St. Louis), Guar Gum (Sigma-Aldrich; St. Louis, Mo.), Plasdone K-90 (ISP Technologies Inc.; Texas City, Tex.).

The following stock solutions were prepared: 0.1M Na—Ac solution pH 6.0, 0.4M Na-Citrate solution pH 6.0, 4.5M urea in 0.1 Na—Ac solution, 2M CaCl2 stock solution in 0.1M Na—Ac pH 6.0, 5% w/v Alginate Ester solution in water for injection (WFI), 40% w/v Arabic gum solution in WFI, 4.2% w/v medium viscosity CMC solution in WFI, 2.5% w/v high viscosity CMC solution in WFI, 1.8% w/v Xanthan gum solution in WFI, 5% w/v Guar gum solution in WFI, 20% w/w Plasdone solution in WFI.

Gelatin solutions of 12.5% w/w (solution A) and 25% w/w (solution B) were prepared in buffer of 3.8M Urea, 0.15M CaCl2 and 0.1M Na—Ac.

mTG powder solutions of 3.75% w/w (solution 1) and 5% w/w (solution 2) were prepared by dissolving Activa TG in 0.4M Na-Citrate.

Methods

Aliquots of 3.75% mTG solution (solution 1) was mixed with each stock viscofier solution at a volumetric ratio of 1:1. If the required concentration of viscofier was lower than half the stock solution, the viscofier was diluted prior to mixing with the mTG solution. Each mTG-viscofier solution was qualitatively assessed for viscosity by manual stirring.

For each type of mTG-viscofier solution, 10 mL of the solution was thoroughly mixed with 20 mL of gelatin solution A and poured into a 100 mL beaker. The viscosity increase of the mixed solution was then tracked using a DV-II+ Pro Viscometer (Brookfield; Middleboro, Mass.) using a t-bar type spindle moving along a helical path at a speed of 0.5 RPM. This experiment was repeated 3 times for each type of mTG-viscofier solution.

Crosslinking rate was defined according to the amount of time that gelatin-mTG-viscofier solution took to achieve viscosity of $9 \times 10^6$ cP. The average crosslinking rate of each gelatin-mTG-viscofier composition was then compared to the average of a control gelatin-mTG composition containing no viscofiers to determine percentage of crosslinking inhibition.

Results

Viscosity of mTG solutions with plasdone, xanthan gum, CMC, gum Arabic, and alginate esther were observed to be noticeably more viscous that mTG solution without addition of viscofier.

Figure 5:
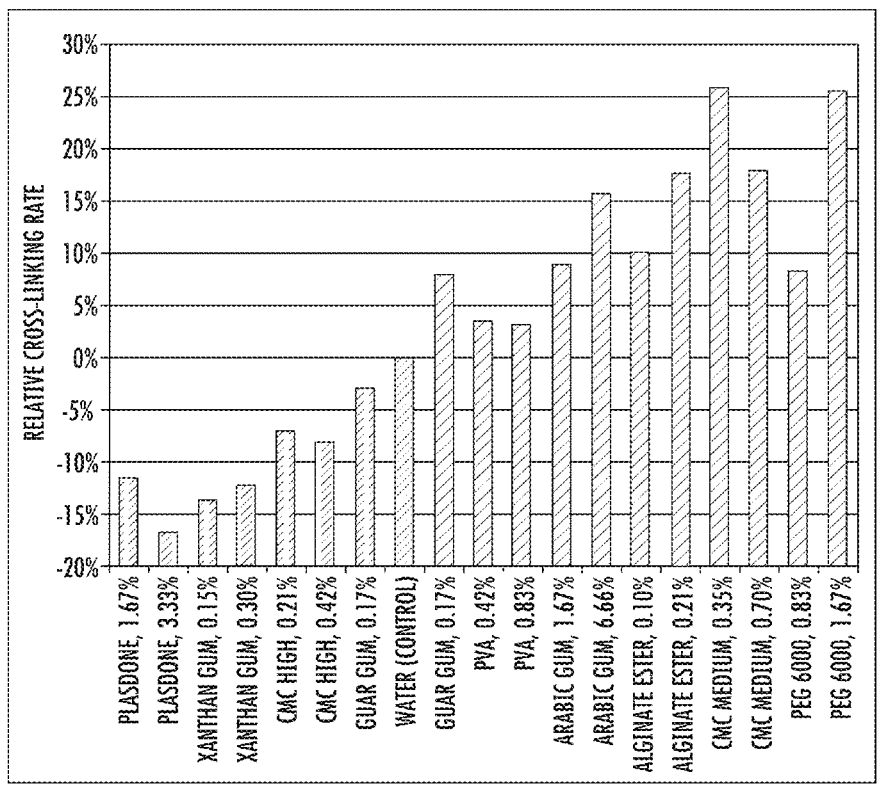
FIG. 5 shows the relative cross linking rate of different plasticizer solutions compared to control.

Relative crosslinking rates of gelatin-mTG solutions with different viscofiers can be seen in FIG. 5, which shows the relative cross linking rate of different plasticizer solutions compared to control. Cross linking was measured quantitativly using viscometery. Percentage values in column title refer to concentration of plasticizer in gel.

No viscofier inhibited reaction by more than 30%. Plasdone, xanthan gum, and high viscosity CMC accelerated the crosslinking rate.

Example 15

Glutamate Improves Tissue Response to a mTG-Crosslinked Gelatin Composition

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Sigma-Aldrich, St. Louis), Sodium Citrate (Sigma-Aldrich, St. Louis), Citric Acid Monohydrate (Sigma-Aldrich, St. Louis), L-Glutamic Acid (Sigma-Aldrich, St. Louis), microbial transglutaminase—ACTIVA-TG (10% enzyme, 90% maltodextrin) (Ajinomoto, Japan), 8 Sprague-Dawley (SD) rats.

Two gelatin solutions were prepared:
1) 25% (w/w) Gelatin solution in 4.5M Urea, 0.1M Sodium Acetate buffer (solution A).
2) Above, to which L-glutamate was added at a concentration of 1.2 g/100 mL of gelatin solution (solution B).

A 7.5% (w/w) Activa TG solution in 0.2M Na-Citrate (mTG solution) was also prepared.

Methods

Prior to each implantation, one gelatin solution was mixed with mTG solution at a volumetric ratio 2:1. 0.1 mL of the mixed gelatin-mTG composition was then immediately implanted at 4 separate subcutaneous sites in a SD rat. This was repeated in 8 rats, 4 rats with gelatin solution A and 4 rats with gelatin solution B (glutamate).

After 14 days, the rats were sacrificed. Lesions from the implantation sites were removed and histopathological evaluations were performed.

All tissues were collected from all animals during the respective scheduled necropsy sessions and fixed in 10% neutral buffered formalin (approximately 4% formaldehyde solution) for at least 48-hr fixation period prior to their shipment to the testing laboratory.

Slide preparation followed by histopathological examination was performed for tissues listed in the study protocol. Tissues were trimmed, embedded in paraffin, sectioned at approximately 5 microns thickness and stained with Hematoxylin & Eosin (H&E).

General assessment and scoring for each of the groups sacrificed after 14 days was performed individually. Total scoring values are relative and contain both chronic and acute inflammation scores.

Results

Histopathological scoring for rats sacrifice after 14 day implantation of each material (values are average of 4 animals). Results are shown in Tables 21 and 22.

TABLE 21

| | Gelatin Solution A + mTG: sacrifice after 14 days | | | | | | | | | | | | | | | |
|---|---|---|---|---|---|---|---|---|---|---|---|---|---|---|---|---|
| | Animal Number | | | | | | | | | | | | | | | |
| | 13 | | | | 14 | | | | 16 | | | | 17 | | | |
| Site number | a | b | c | d | a | b | c | D | a | b | c | d | a | b | c | d |
| Polymorhonuclear cells* | | 3 | | | | 3 | | | | 3 | | | | 3 | | |
| Eosinophils* | | 3 | | | | 3 | | | | 3 | | | | 3 | | |
| Lymphocytes* | | 1 | | | | 1 | | | | 1 | | | | 1 | | |
| Plasma cells* | | 1 | | | | 1 | | | | 1 | | | | 1 | | |
| Marcophages* | | 2 | | | | 2 | | | | 2 | | | | 2 | | |

TABLE 21-continued

Gelatin Solution A + mTG: sacrifice after 14 days

| | Animal Number | | | | | | | | | | | | | | |
|---|---|---|---|---|---|---|---|---|---|---|---|---|---|---|---|
| | 13 | | | | 14 | | | 16 | | | | 17 | | | |
| Site number | a | b | c | d | a | b | c | D | a | b | c | d | a | b | c | d |
| Giant cells* | | 1 | | | | 1 | | | | 1 | | | | 1 | | |
| Necrosis | | 0 | | | | 0 | | | | 0 | | | | 0 | | |
| Total per site | | 11 | | | | 11 | | | | 11 | | | | 11 | | |
| SUBTOTAL I (×2) | | 88 | | | | 88 | | | | 88 | | | | 88 | | |
| Fibroplasia | | 2 | | | | 2 | | | | 2 | | | | 2 | | |
| Fibrosis | | 3 | | | | 3 | | | | 3 | | | | 3 | | |
| Total per site | | 5 | | | | 5 | | | | 5 | | | | 5 | | |
| SUBTOTAL II | | 20 | | | | 20 | | | | 20 | | | | 20 | | |
| TOTAL [SUB-TOTAL I + II] | | 108 | | | | 108 | | | | 108 | | | | 108 | | |
| GROUP TOTAL | | | | | | | | 432 | | | | | | | | |
| GROUP AVERAGE* | | | | | | | | 27 | | | | | | | | |

TABLE 22

Gelatin Solution B (glutamate) + mTG: sacrifice after 14 days

| | Animal Number | | | | | | | | | | | | | | |
|---|---|---|---|---|---|---|---|---|---|---|---|---|---|---|---|
| | 18 | | | | 19 | | | | 20 | | | | 21 | | |
| Site number | a | b | c | d | a | b | c | D | a+b | c | d | a | b | c | d |
| Polymorhonuclear cells* | | 2 | | | | 2 | | | 2 | | | | 2 | | |
| Eosinophils* | | 2 | | | | 2 | | | 2 | | | | 2 | | |
| Lymphocytes* | | 1 | | | | 1 | | | 1 | | | | 1 | | |
| Plasma cells* | | 1 | | | | 1 | | | 1 | | | | 1 | | |
| Marcophages* | | 3 | | | | 3 | | | 2 | | | | 2 | | |
| Giant cells* | | 1 | | | | 1 | | | 1 | | | | 1 | | |
| Necrosis | | 0 | | | | 0 | | | 0 | | | | 0 | | |
| Total per site | | 10 | | | | 10 | | | 9 | | | | 9 | | |
| SUBTOTAL I (×2) | | 80 | | | | 80 | | | 72 | | | | 72 | | |
| Fibroplasia | | 2 | | | | 2 | | | 2 | | | | 2 | | |
| Fibrosis | | 3 | | | | 3 | | | 3 | | | | 3 | | |
| Total per site | | 5 | | | | 5 | | | 5 | | | | 5 | | |
| SUBTOTAL II | | 20 | | | | 20 | | | 20 | | | | 20 | | |
| TOTAL [SUB-TOTAL I + II] | | 100 | | | | 100 | | | 92 | | | | 92 | | |
| GROUP TOTAL | | | | | | | | 384 | | | | | | | |
| Group AVERAGE** | | | | | | | | 24 | | | | | | | |

These results indicate that under otherwise identical conditions, the addition of glutamate to an implanted crosslinked gelatin composition resulted in a lower level of inflammatory reaction.

Example 16

The Effect of Proline and Trehalose on Restoring the Physical Gelation of a Gelatin Solution with a Chaotrope-Lowered Sol-Gel Transition Point Materials The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Proline (Sigma-Aldrich, St. Louis), Trehalose dihydrate (Sigma-Aldrich, St. Louis).

Methods

Stock solutions of 0.1M Sodium Acetate buffer pH 6.0, buffer pH 6.0, 4.5M Urea, 2M CaCl2, were prepared.

25% (w/w) Gelatin solution in 3.8M Urea, 0.15M Ca, 0.1M Sodium Acetate (Control solution), 25% (w/w) Gelatin solution in 1M Proline, 3.8M Urea, 0.15M Ca, 0.1M Sodium Acetate (Solution A), 25% (w/w) Gelatin solution in 1.5M Proline, 3.8M Urea, 0.15M Ca, 0.1M Sodium Acetate (Solution B); 25% (w/w) Gelatin solution in 0.5M Proline, 0.4M Trehalose 3.8M Urea, 0.15M Ca, 0.1M Sodium Acetate (Solution C); 25% (w/w) Gelatin solution 1.5M Proline, 0.4M Trehalose 3.8M Urea, 0.15M Ca, 0.1M Sodium Acetate (Solution D); were prepared. All solutions were heated to 50° C. under constant stirring to achieve homogenous solutions.

After solutions were obtained, all solutions were moved to a thermostatic bath set to 25° C. After 60 minutes, physical state of each solution was checked by palpating the solution. Solutions were then moved to a 22° C. and physical state was checked again after another 60 minutes.

Results

The control solution remained, as expected, in mildly viscous liquid form at 25° C. Solution A was very highly viscous. Solutions B, C and D were completely gelled after 60 minutes.

After the additional 60 minutes at 22° C., Solution A formed a solid gel as well.

Control gelatin solution did not form a gel at 22° C. or 25° C.

These observations indicate that the addition of Proline leads to a higher transition point of gelatin solutions in comparison to control solutions. The results also indicate that there is a synergistic effect between Proline and Trehalose when combined together, in comparison to Proline alone, as 0.5M Proline with 0.4M Trehalose caused gelation at 25° C. whereas 1M Proline alone did not.

Example 17

Effect of Proline and Glutamate (Kosmotropes) to Increase the Elasticity of mTG-Crosslinked Gelatin Gels Materials The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), L-Proline 99% (Sigma, St. Louis, Mo.), L-Glutamic acid (Glutamate), non animal source (Sigma, St. Louis, Mo.), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCl2, were prepared.

25% (w/w) Gelatin solution in 3.8M Urea, 0.15M Ca, 0.1M Sodium Acetate (solution A), 0.25% (w/w) mTG in 0.2M Na-Citrate (mTG control), 0.25% (w/w) mTG with 0.04 g/ml Glutamate in 0.2M Na-Citrate (mTG 1) and 0.25% (w/w) mTG 2.5M Proline in 0.2M Na-Citrate (mTG 2) were prepared.

Tensile testing was then performed on crosslinked gels formed by mixing aliquots of each of the above gelatin solutions with aliquots of mTG solution.

For each test, 6 ml of gelatin solution were mixed with 3 ml of mTG solution. The resulting mixture was applied to dog bone shaped molds, with 2 mL in each mold. The effective testing cross-sectional area of the gels formed in these molds was 12 mm by 1.7 mm Molds containing gels were incubated at 370 C for 10 min. After incubation, the molds were covered in saline and the formed gels were extracted from the molds.

For the testing of each gel, the tabs on either end of the dogbone shaped gel were clamped into a Model 3343 Single Column Materials Testing System (Instron™; Norwood, Mass.). The top tab was then pulled upwards at a rate of 0.5 mm/s, resulting in the creation of tensile force on the gel dogbone. Tension of sample was continued until failure was observed. Bluehill 2 Materials Testing Software (Instron™; Norwood, Mass.) was used to analyze results and calculate material properties including elastic modulus, peak stress, and strain to break.

Results

The material testing results indicate that both Proline and Glutamate can be used to increase the elasticity of a mTG-crosslinked gelatin composition, as shown in Table 23.

TABLE 23

Proline and Glutamate Increase the Elasticity of the Composition

| solution A reacted with | Average Modulus, kPa | Average Tensile Stress at Break, kPa | Average Tensile Strain at Break, % |
|---|---|---|---|
| mTG control | 79 | 50 | 62 |
| mTG 1 (glutamate) | 74 | 58 | 84 |
| mTG 2 (proline) | 60 | 44 | 75 |

Example 18

Effect of Surfactants Tween 20 and Tween 80 on Increasing the Elasticity of Crosslinked Protein Composition This Example relates to the effect of surfactants when used above their CMC (critical micelle concentrations). As a non-limiting example, two members of the "Tween" family are given. Tween™ hydrophilic surfactants (Polysorbates) are a family of PEG sorbitan esters (polyoxyethylene-sorbitan-fatty acid esters), for example mono- and tri-lauryl, palmityl, stearyl and oleyl esters of the type known and commercially available under the trade name Tween™ (Fiedler, H. P., "Lexikon der Hilfsstoffe fur Pharmazie, Kosmetic and Angrenzende Gebiete", Editio Cantor. D-7960 Aulendorf, 3rd edition, 1989, pages 1300-1304). Tween™ 20 (polyoxyethylene (20)sorbitan monolaurate) has an HLB of 16.7. Other types of Tween™ surfactants may also be useful for the compositions of at least some embodiments of the present invention.

Tween™ surfactants are soluble in water but not in oil. The chemical structure of this family of surfactants features one, two or three short PEG chains, generally of about 5 to 20 ethylene glycol units, connected by an ester bond to sorbitan. These surfactants are produced by various companies (Croda, ICI, Sandoz, Mazer, Atlas) and may appear under various trade names, besides Tween™: Sorlate™, Monitan™, Crillet™ and so forth. Members of this family which are polysorbates 20, 21, 0, 60, 61, 65, 80 and 85 are preferred for this embodiment of the present invention.

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Tween 20 (Sigma, St. Louis, Mo.), Tween 80 (Sigma, St. Louis, Mo.), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCl2, were prepared.

25% (w/w) Gelatin solution in 3.8M Urea, 0.15M Ca, 0.1M Sodium Acetate (solution A), 25% (w/w) Gelatin solution with 0.1% or 1% Tween 20 in 3.8M Urea, 0.15M Ca, 0.1M Sodium Acetate (solutions B, C respectively), 25% (w/w) Gelatin solution with 0.1% or 1% Tween 80 in 3.8M Urea, 0.15M Ca, 0.1M Sodium Acetate (solutions D, E respectively) and 0.25% (w/w) solution food-grade mTG in 0.2M Na-Citrate (solution 1) were prepared.

Tensile testing was then performed on crosslinked gels formed by mixing aliquots of each of the above gelatin solutions with aliquots of mTG solution.

For each test, 6 ml of gelatin solution were mixed with 3 ml of mTG solution. The resulting mixture was applied to dog bone shaped molds, with 2 mL in each mold. The effective testing cross-sectional area of the gels formed in these molds was 12 mm by 1.7 mm. Molds containing gels were incubated at 37 C for 10 min. After incubation, the molds were covered in saline and the formed gels were extracted from the molds.

For the testing of each gel, the tabs on either end of the dogbone shaped gel were clamped into a Model 3343 Single Column Materials Testing System (Instron™; Norwood, Mass.). The top tab was then pulled upwards at a rate of 0.5 mm/s, resulting in the creation of tensile force on the gel dogbone. Tension of sample was continued until failure was observed. Bluehill 2 Materials Testing Software (Instron™; Norwood, Mass.) was used to analyze results and calculate material properties including elastic modulus, peak stress, and strain to break.

Results

The material testing results indicate that both Tween20 and Tween80 are useful for increasing the elasticity (strain to break) of the crosslinked gelatin gels and that this effect is concentration dependant, as shown in Table 24.

TABLE 24

Effect of Tween Surfactants on Elasticity

|  | Solution A | Solution B | Solution C | Solution D | Solution E |
|---|---|---|---|---|---|
| Elastic Modulus (kPa) | | | | | |
| Average | 103.16 | 102.87 | 81.62 | 92.38 | 96.56 |
| StdDev | 18.10 | 8.68 | 14.22 | 13.26 | 10.74 |
| Stress at break (kPa) | | | | | |
| Average | 57.67 | 54.07 | 68.14 | 63.95 | 74.01 |
| StdDev | 28.94 | 12.57 | 12.11 | 6.57 | 9.29 |
| Strain at break (%) | | | | | |
| Average | 57.17 | 54.86 | 89.24 | 73.36 | 79.10 |
| StdDev | 25.14 | 14.26 | 5.03 | 15.80 | 8.28 |

Example 19

Use of Cystamine, Cysteine and Melanin as mTG Inhibitors

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Cystamine dihydrochloride 98% (Sigma-Aldrich, St. Louis), L-Cystein 97% (Sigma-Aldrich, St. Louis), Melanin (Sigma-Aldrich, St. Louis) 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCL2, were prepared.

25% (w/w) Gelatin solution in 3.8M Urea, 0.15M Ca, 0.1M Sodium Acetate (control solution), 25% (w/w) Gelatin 0.1% w/v Cystamine solution in 3.8M Urea, 0.15M Ca, 0.1M Sodium Acetate (solution A), 25% (w/w) Gelatin 10% w/v Cystein solution in 3.8M Urea, 0.15M Ca, 0.1M Sodium Acetate (solution B), 0.75% (w/w) mTG in 0.2M Na-Citrate (solution 1), 0.25% (w/w) mTG in 0.2M Na-Citrate (solution 2), 0.25% (w/w) mTG in 0.2M Na-Citrate with 2 mg/ml Melanin (solution 3), 0.25% (w/w) mTG in 0.2M Na-Citrate with 10 mg/ml Melanin (solution 4) were prepared.

Gelatin solutions containing Cystamin and Cystein (A, B) were tested by viscometer with mTG solution 1.

mTG solutions containing Melanin (3, 4) were tested in a qualitative manner with control solution.

Viscometer Tests

For each viscometry test, 20 mL of gelatin solution was mixed with 10 mL of mTG solution in a 50 mL beaker. The viscosity of the mixed gelatin-mTG solution was then tracked as it underwent gelation. Different test groups were compared by recording the time required for each test group to achieve 30% and 90% of the maximum viscosity able to be recorded by the viscometer at the specific speed and with the specific spindle used for that test.

In this experiment, a DV II+ PRO Digital Viscometer (Brookfield Engineering, Middleboro, Mass.) was used with a T-E 95 "t-bar" spindle. A helipath viscometer stand was used to maintain vertical movement of the spindle over the course of the viscometer test. The helipath moved along a 1 cm path. The viscometer readings were outputted by the viscometer and read using HyperTerminal software at a rate of 1 reading per second. The rotational speed of the spindle for the viscometry test was 0.5 rpm. The maximum recordable viscosity at this speed with the T-E 95 spindle was $10 \times 10^6$ cP, meaning that the 30% point was equivalent to $3 \times 10^6$ cP and the 90% point was equivalent to $9 \times 10^6$ cP.

The beaker was submerged in a 37° C. water bath for the entire extent of the viscometer test. Average temperature within the beaker also recorded throughout the test to ensure consistency between test groups.

Qualitative Crosslinking Test

Gelatin and mTG solutions were mixed in 2:1 ratio, then moved to a 37 C incubator and crosslinking time was defined when an apparent gelation was detected.

Results

Figure 6:
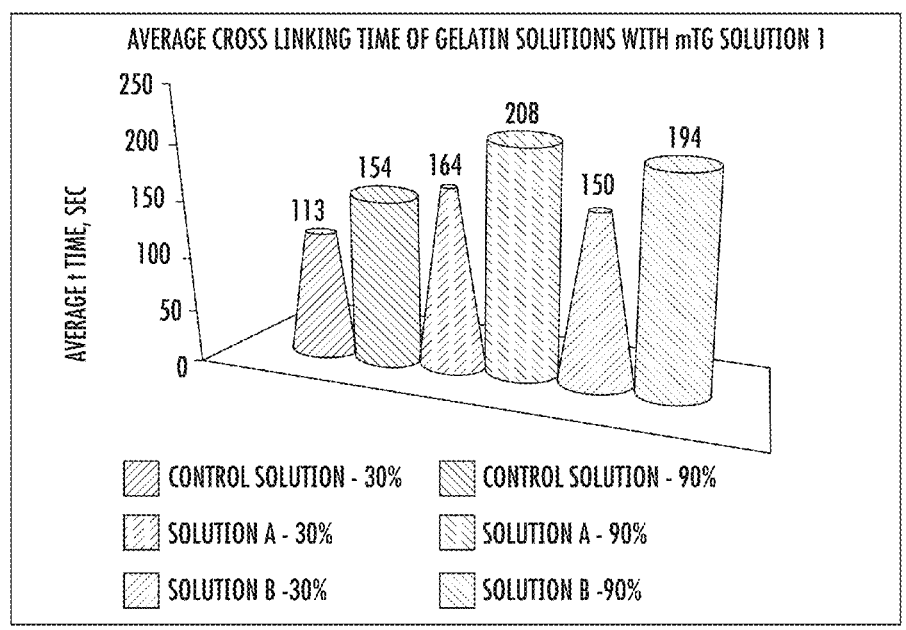
FIG. 6 shows results of some illustrative gelatin solutions according to some embodiments of the present invention: control, A and B.

Cystamin and Cystein Inhibition Results:

FIG. 6 shows results of gelatin solutions control, A and B. As can be seen, addition of the Cystamine to the gelatin solution increased crosslinking time of the matrix by about 40%. Addition of Cystein resulted an increase of about 28% in the average crosslinking time. These results demonstrate mTG inhibition by addition of Cystamine or Cystein to the gelatin solution.

When examined, crosslinked gels from solutions containing Cystamine or Cystein appeared to be more flexible than the equivalent crosslinked gel with no Cystamine or Cystein additives.

Melanin Results:

Table 25 describes the results of crosslinking time with regard to the effect of Melanin. When mTG was used with Melanin, crosslinking time increased significantly. Increasing Melanin concentration increased crosslinking time. This finding demonstrates mTG inhibition by addition of Melanin.

TABLE 25

Effect of Melanin on crosslinking time

| Composition of crosslinked gel | Crosslinking time, min |
|---|---|
| Control gelatin solution + mTG solution 2 (no melanin) | 0:40 |
| Control gelatin solution + mTG solution 3 (2 mg/ml melanin) | 3:00 |
| Control gelatin solution + mTG solution 4 (10 mg/ml melanin) | 6:00 |

Example 20

Effect of PEG-Amine on the Kinetics of a Gelatin Crosslinking Reaction and the Elasticity of a Crosslinked Gelatin Composition Materials The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), PEG-Amine MW 5000 (Nof Corporation, Japan), PEG 6000 (Fluka, Switzerland), microbial transglutaminase—ACTIVA-TG (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCL2, were prepared.

25% (w/w) Gelatin in 3.8M Urea, 0.15M CaCl2, 0.1M Sodium Acetate (control solution), 25% (w/w) Gelatin with 5% w/v PEG-amine in 3.8M Urea, 0.15M CaCl2, 0.1M Sodium Acetate (Solution A), 25% (w/w) Gelatin with 10% PEG-amine in 3.8M Urea, 0.15M CaCl2, 0.1M Sodium Acetate (Solution B), 25% (w/w) Gelatin with 20% PEG-amine in 3.8M Urea, 0.15M CaCl2, 0.1M Sodium Acetate (Solution C), 25% (w/w) Gelatin with 20% PEG 6000 in 3.8M Urea, 0.15M CaCl2, 0.1M Sodium Acetate (Solution D), 0.25% (w/w) mTG in 0.2M Na-Citrate (mTG solution) were prepared.

Solutions were examined using Qualitative and Elasticity tests.

Qualitative Crosslinking Test

Gelatin solutions A, B, and C were each mixed with the mTG solution at a 2:1 volumetric ratio in glass tubes, then moved to a 37° C. shaking incubator. Gelation time was defined as the time at which flow of the liquid solution was observed to cease.

Elasticity Test

The control solution and Solution B crosslinked with mTG solution were examined for changes in elasticity over time.

For each elasticity test, 6 mL of gelatin solution were mixed with 3 ml of mTG solution. The resulting mixture was applied to dog-bone mold, 2 mL in each mold. Molds were incubated at 37° C. for 10 min. After the incubation, molds were covered in saline and gelatin-mTG composition extracted from the mold.

The specimens were then incubated in saline at 37° C., or examined immediately. Thickness of gelatin-mTG composition removed from gel was measured using a caliper.

For the testing of each gel, the tabs on either end of the dogbone shaped gel were clamped into a Model 3343 Single Column Materials Testing System (Instron™; Norwood, Mass.). The top tab was then pulled upwards at a rate of 0.5 mm/s, resulting in the creation of tensile force on the gel dogbone. Tension of sample was continued until failure was observed. Bluehill 2 Materials Testing Software (Instron™; Norwood, Mass.) was used to analyze results and calculate material properties including elastic modulus, peak stress, and strain to break.

Results

Qualitative Crosslinking Test

Table 27 displays the results for the qualitative crosslinking test, showing that increasing amounts of PEG-amine decreases the time to gelation.

TABLE 27 results of crosslinking

| Gelatin Solution | Gelation time [min] |
|---|---|
| Solution A | 3:50 |
| Solution B | 2:00 |
| Solution C | 1:20 |
| Control Solution | 4:40 |

Elasticity Test

Table 28 displays the average results for the elasticity tests; results are for 2 hr incubation in saline at 37° C. The results show that PEG-amine can increase the elasticity of the gelled composition.

TABLE 28

Elasticity Test Results

| Gelatin Solution | Modulus (kPa) | Tensile Stress at Break (kPa) | Tensile Strain at Break (%) |
|---|---|---|---|
| Control | 90.50 | 46.28 | 51.23 |
| Solution B | 48.06 | 35.71 | 80.18 |
| Solution D | 55.03 | 30.13 | 57.00 |

Overall, these results indicate that the inclusion of PEG-Amine can affect the gelation kinetics of mTG-crosslinking of a gelatin solution; and the inclusion of PEG-Amine can increase the elasticity of a crosslinked gelatin composition. Another non-limiting example of a suitable PEG derivative capable of covalently binding to gelatin is PVA-amine, which is also encompassed by this embodiment of the present invention.

Example 21

Inhibition of Carbamylation

This Example shows that glycine inhibits carbamylation in a gelatin solution containing urea in a dose dependant manner without inhibiting mTG cross-linking afterwards. Histidine can similarly be used to inhibit carbamylation.

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Glycine, non animal source (Sigma, St. Louis, Mo.), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCL2, were prepared.

25% (w/w) Gelatin solution in 3.8M Urea, 0.15M Ca, 0.1M Sodium Acetate (control solution), 25% (w/w) Gelatin 0.1M Histidine solution in 3.8M Urea, 0.15M Ca, 0.1M Sodium Acetate (solution A), 25% (w/w) Gelatin 0.1M Glycine solution in 3.8M Urea, 0.15M Ca, 0.1M Sodium Acetate (solution B), 25% (w/w) Gelatin 0.4M Glycine solution in 3.8M Urea, 0.15M Ca, 0.1M Sodium Acetate (solution C), 25% (w/w) Gelatin 0.5M Glycine solution in 3.8M Urea, 0.15M Ca, 0.1M Sodium Acetate (solution D), 25% (w/w) Gelatin 0.7M Glycine solution in 3.8M Urea, 0.15M Ca, 0.1M Sodium Acetate (solution E), 25% (w/w) Gelatin 0.9M Glycine solution in 3.8M Urea, 0.15M Ca, 0.1M Sodium Acetate (solution F), 25% (w/w) Gelatin 1M Glycine solution in 3.8M Urea, 0.15M Ca, 0.1M Sodium Acetate (solution G), 0.25% (w/w) mTG in 0.2M Na-Citrate (solution 1), 0.75% (w/w) mTG in 0.2M Na-Citrate (solution 2) were prepared.

Results

Figure 7A:
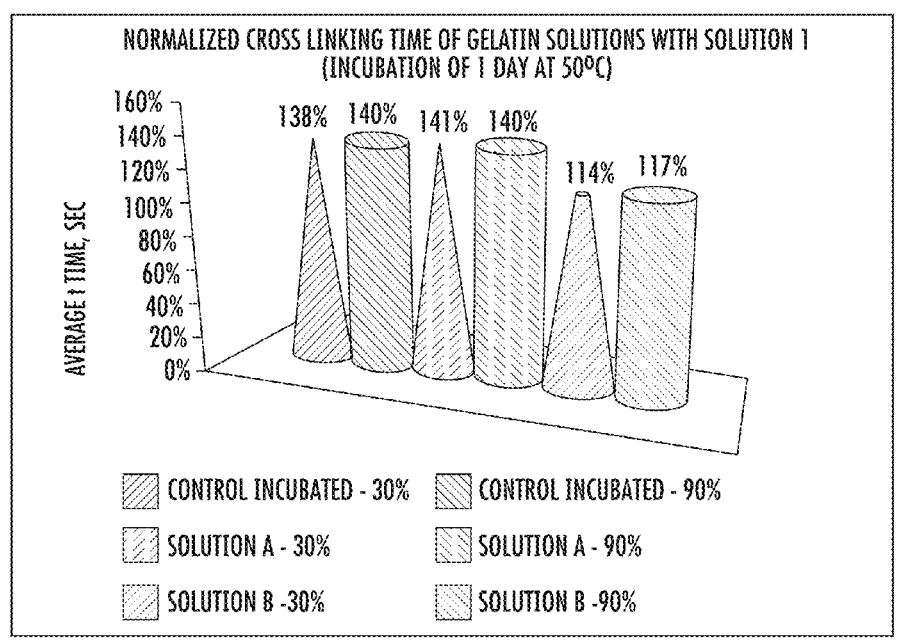
FIGS. 7A, 7B and 7C summarize results of various illustrative gelatin solutions according to some embodiments of the present invention with various Glycine and Histidine additives, functioning as Carbamylation inhibitors, which were crosslinked and tested by viscometer after different incubation times.
Figure 7B:
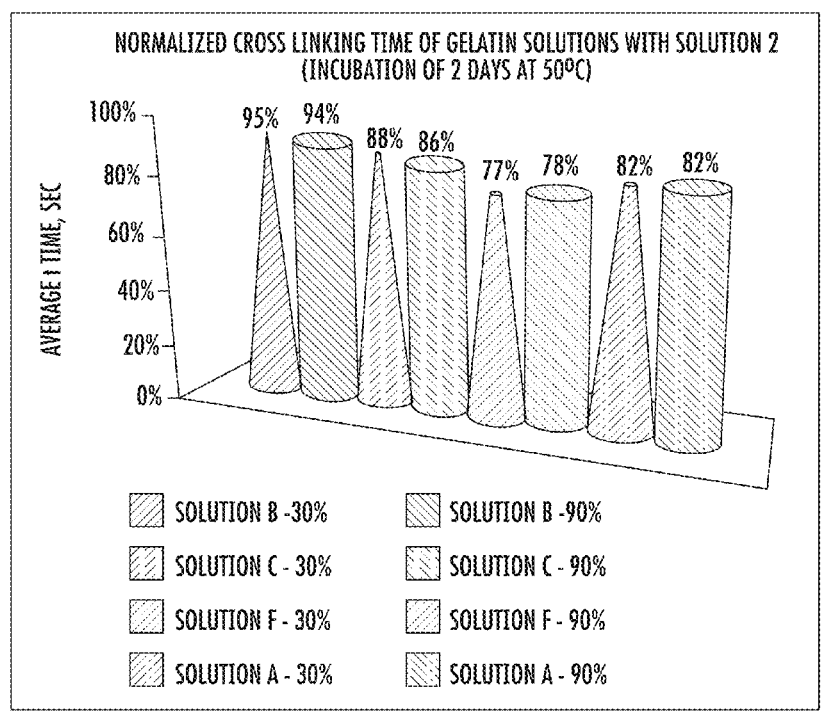
Figure 7C:
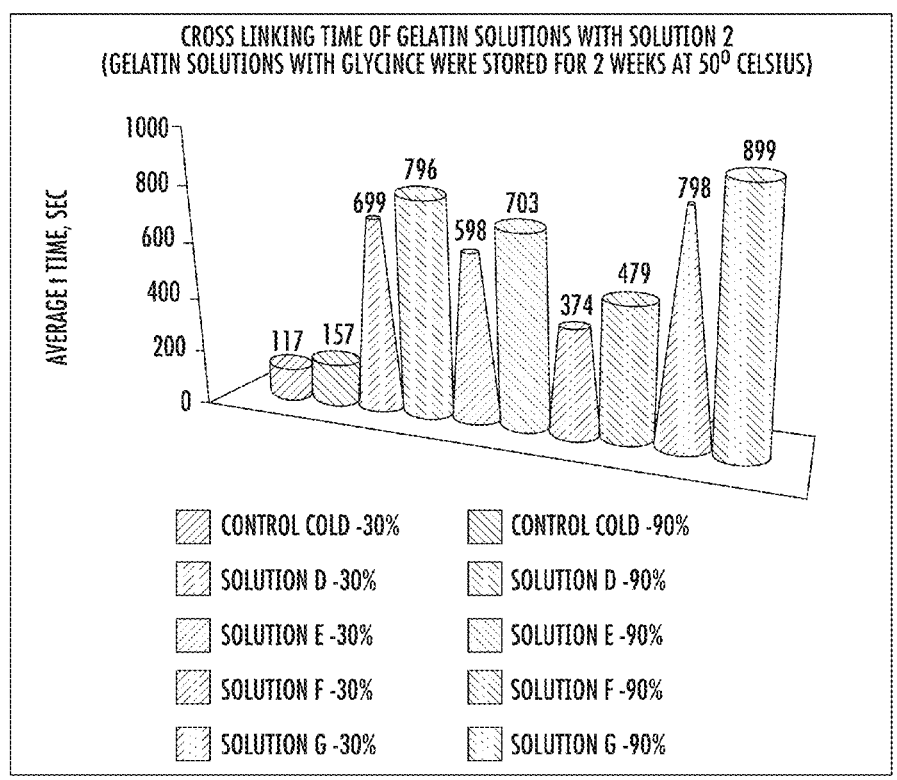

FIGS. 7A, 7B and 7C summarize results of gelatin solutions with various Glycine and Histidine additives, functioning as Carbamylation inhibitors, which were crosslinked and tested by viscometer after different incubation times at high temperature (50° C.). All figures present values of both 30% and 90% of overall crosslinking time.

FIG. 7A presents normalized crosslinking time values of gelatin solutions with and without Glycine or Histidine additives (0.1 M each) after one day of incubation at 50° C. Values are normalized based on an control solution with no additives which was stored at 4 C for one day, therefore value of 100% defines the time needed to achieve crosslinking time as the gelatin control solution. FIG. 7A shows the normalized cross linking time of gelatin control, solution A and solution B after incubation at 50 C for one day. The cones show the time to torque 30% while the cylinders show the time to torque of 90%. The data are shown in pairs: the first two relate to control solution alone, the second relate to solution A and the third pair relates to solution B.

Results from FIG. 7A indicate that after a day of incubation, both gelatin solution with 0.1M Histidine (A) and gelatin solution with no additives which was incubated at 50° C. (control) took 38%-40% longer to achieve viscosity levels compared to control which was stored at 4° C. However, use of 0.1M Glycine (B) reduced the level of reaction inhibition, with crosslinking reaction delay being limited to 14-17%.

FIG. 7B presents normalized crosslinking time values of gelatin solutions with and without Glycine or Histidine additives after two days of incubation at 50° C. The cones show the time to torque 30% while the cylinders show the time to torque of 90%. The data are shown in pairs: the first two relate to solution B alone, the second relate to solution C, the third pair relates to solution F and the fourth pair relates to solution F. Values were normalized based on an gelatin control solution with no additives which was also incubated at 50° C. for two days, therefore 100% of crosslinking time is a time needed to achieve crosslinking time as the control incubated solution.

Results from FIG. 7B indicate that gelatin solution with highest Glycine concentration, 0.9M (solution F), led to the best crosslinking time. The reaction was about 22% faster than the control solution, while Glycine concentration of 0.1M (solution B) led to a reaction only to 5-6% faster reaction time than control. Use of gelatin solution with 0.1M Histidine (solution A) led to similar crosslinking time as in the gelatin solution with 0.9M Glycine (F), with the crosslinking time was 18% faster than the control solution.

FIG. 7C presents crosslinking time values of gelatin solutions with Glycine after two weeks of incubation at 50 C, and crosslinking time values of gelatin control solution stored at 4 C for two weeks. The cones show the time to torque 30% while the cylinders show the time to torque of 90%. The data are shown in pairs: the first two relate to control solution alone, the second relate to solution D, the third pair relates to solution E, the fourth pair relates to solution F and the fifth pair relates to solution G.

Results from FIG. 7C indicate that use of gelatin solution with the highest Glycine concentration does not necessarily lead to the best results, as crosslinking time of gelatin solution with 0.9M Glycine (F) was by 50% lower than crosslinking time achieved with gelatin solution with 1M Glycine (G). Also, it appears 0.9M Glycine was the optimum concentration as 0.7M Glycine (E) achieved crosslinking time higher by about 50% than gelatin solution with 0.9M Glycine. Results also indicated that after more than 23 minutes, no crosslinking was observed with gelatin solution with no additives, an indication of the deterioration of the solution.

Overall, these results indicate that both glycine and histidine can inhibit carbamylation reactions in gelatin. However, the specific concentrations and choice of substances is dependant on the conditions of cyanate production in solutions.

Example 22

Cyanate Addition for Partially Crosslinking of Gelatin Solutions Containing No Urea This Example shows that the presence of sodium cyanate results in an inhibitory effect, confirming that urea breakdown is responsible for inhibition of mTG crosslinking Materials The following materials were used in the experiment: Gelita 275 bloom, type A porcine gelatin (Gelita, Sioux City), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Sodium Cyanate 96% (Sigma-Aldrich, St. Louis), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0 and 0.2M Sodium Citrate buffer pH 6.0 were prepared.

25% (w/w) Gelatin solution in 0.1M Sodium Acetate (control solution), 25% (w/w) Gelatin+0.1M Sodium Cyanate in 0.1M Sodium Acetate (solution A) and 0.25% (w/w) mTG in 0.2M Na-Citrate (solution 1) were prepared.

Viscometer Tests

Viscometer tests were carried out as described in Example 19.

Results

Figure 8:
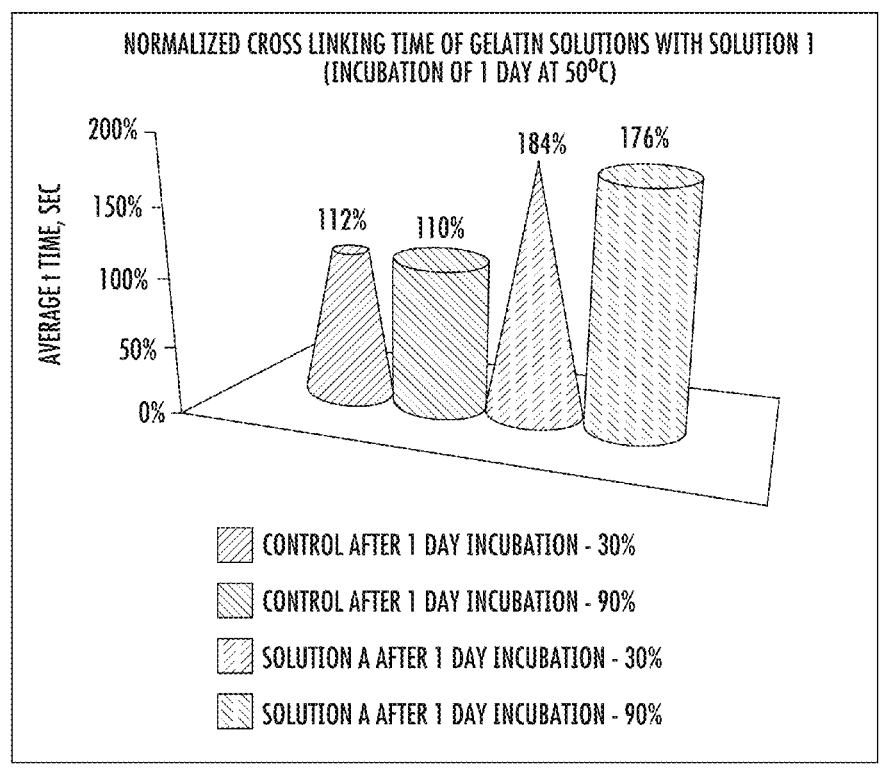
FIG. 8 summarizes results of control solutions with and without Cyanate additives according to some embodiments of the present invention which were crosslinked and tested by viscometer after different incubation times of high temperature.

FIG. 8 summarizes results of control solutions with and without Cyanate additives which were crosslinked and tested by viscometer after different incubation times of high temperature (50 C). The cones show the time to torque 30% while the cylinders show the time to torque of 90% (ie cross linking time). The data are shown in pairs: the first two relate to the control solution, while the second relate to solution A. Values of crosslinking time are normalized based on control solution with no additives which was stored at 4 C for one day. Therefore, value of 100% is the time needed to achieve crosslinking of that solution.

Results indicate that while the control solution with incubation of 50 C showed a slightly increased crosslinking time (by about 10%), the solution which also contained 0.1M Cyanate (solution A) increased significantly its crosslinking time by more than 76%. This finding demonstrates that addition of Cyanate anions, either with direct addition or by decomposing urea, can significantly deteriorate crosslinking time of gelatin solutions and has a significant inhibitory effect.

Example 23

A Gelatin Solution can be Completely Succinylated Such that the Gelatin is No Longer a Substrate for mTG Crosslinking Materials The following materials were used in the experiment: Gelita 275 bloom, type A porcine gelatin (Gelita, Sioux City), Succinic anhydride (Sigma-Aldrich, St. Louis), Sodium hydroxide (Ridel-De Haen), Sodium Bicarbonate (Frutarum, Israel), Sodium Citrate (Sigma-Aldrich, St. Louis), 10% microbial Transglutaminase—ACTIVA-TG 10% (10% enzyme, 90% maltodextrin) (Ajinomoto, Japan).

Methods

Stock solutions of 0.1M Bicarbonate buffer pH 8.0, 4M Sodium hydroxide and 0.2M Na-Citrate were prepared.

1% (w/w) Gelatin solution in 0.1M Bicarbonate buffer was prepared (solution A). The solution was heated to temperature of 37 C while constant stirring was applied. Also, 0.75% (w/w) mTG in 0.2M Na-Citrate (mTG solution) was prepared.

After a homogenous steady state was achieved, succinic anhydride was added to the solution in powdered form. The solution's pH was monitored constantly and was kept at pH=8 by addition of 4M Sodium hydroxide. When no more pH changes were observed, the solution was placed in dialysis bag and submerged in distilled water for 24 hr.

The resultant solution was concentrated using an Ultrafiltration process with a 30 kDa membrane cut-off. During the process intake pressure did not exceed 1.5 bar.

The solution's concentration was determined using the solution's absorbance at 280 nm (Solution A). A corresponding solution was prepared (Solution B) of unsuccinylated gelatin at the same concentration as solution A.

2.5 ml of mTG solution was mixed with 5 ml of solutions A and B, respectively, and placed at 40 C.

Results

Qualitative Crosslinking Test

During the solutions' incubation it was observed that solution B underwent crosslinking after 1 min, while solution A did not undergo crosslinking even after 2 hr. Therefore succinylation of the gelatin clearly blocked cross-linking Example 24

Succinylated Gelatin can be Mixed with Non-Modified Gelatin in a Manner that Improves the Mechanical Properties of a Crosslinked Gelatin Composition Materials The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), 10% microbial Transglutaminase—ACTIVA-TG 10% (10% enzyme, 90% maltodextrin) (Ajinomoto, Japan), Succinylated gelatin which was prepared as previously described.

Methods

Stock solutions of 0.1M Sodium Acetate buffer pH 6.0, 0.2M Sodium Citrate buffer pH 6.0, 4.5M Urea, 2M CaCL2, were prepared.

21% (w/v) Gelatin solution with Succinylated gelatin solution and 3.8M Urea, 0.15M Ca, 0.1M Sodium Acetate solution (Solution A), 21% (w/v) Gelatin solution with distilled water and 3.8M Urea, 0.15M Ca, 0.1M Sodium Acetate solution (Solution B), 0.75% (w/w) mTG in 0.2M Na-Citrate (solution 1) were prepared.

The mTG crosslinking time of solutions A and B were tested by viscometer. For each viscometry test, 20 mL of gelatin solution was mixed with 10 mL of mTG solution in a 50 mL beaker. The viscosity of the mixed gelatin-mTG solution was then tracked as it underwent gelation. Different test groups were compared by recording the time required for each test group to achieve 90% of the maximum viscosity able to be recorded by the viscometer at the specific speed and with the specific spindle used for that test.

In this experiment, a DV II+ PRO Digital Viscometer (Brookfield Engineering, Middleboro, Mass.) was used with a T-E 95 "t-bar" spindle. A helipath viscometer stand was used to maintain vertical movement of the spindle over the course of the viscometer test. The helipath moved along a 1 cm path. The viscometer readings were outputted by the viscometer and read using HyperTerminal software at a rate of 1 reading per second. The rotational speed of the spindle for the viscometry test was 0.5 rpm. The maximum recordable viscosity at this speed with the T-E 95 spindle was $10 \times 10^6$ cP, meaning that the 30% point was equivalent to $3 \times 10^6$ cP and the 90% point was equivalent to $9 \times 10^6$ cP.

The beaker was submerged in a 37° C. water bath for the entire extent of the viscometer test. Average temperature within the beaker also recorded throughout the test to ensure consistency between test groups.

Upon the completion of the viscometry test, the resulting crosslinked gelatin plug was removed from the beaker and submerged in a saline bath. After 24 hours, both the Solution A and Solution B gelatin plugs were removed from the saline bath and manually palpated to assess comparative flexibility.

Results

Table 29 describes results of crosslinking time, demonstrating that a mixture of succinylated and non-succinylated has a longer time requirement for crosslinking.

TABLE 29

| Composition of crosslinked gel | Average crosslinking time, min |
|---|---|
| Solution A | 2:17 |
| Solution B | 1:30 |

All three (3) gelatin plugs formed from solution A were noticeably more flexible than all three (3) gelatin plugs formed from solution B, indicating that the inclusion of succinylated gelatin in a gelatin solution reduces the brittleness of that solution after crosslinking by mTG.

Example 25

Use of Carbamylation to Block the Amine Group Substrates in Gelatin

This example describes the use of carbamylation to improve the flexibility and elasticity of a crosslinked gelatin composition.

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Sodium Cyanate 96% (Sigma-Aldrich, St. Louis), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCL2, 0.3M Sodium Cyanate were prepared.

25% (w/w) Gelatin solution in 3.8M Urea, 0.15M Ca, 0.1M Sodium Acetate (solution A), and 0.75% (w/w) mTG in 0.2M Na-Citrate (solution 1) were prepared.

Viscometer Tests

Viscometer tests were carried out as described in Example 19.

Prior to mixing gelatin and enzyme, sodium Cyanate was added either to solution A or 1 as follows:

Addition of 100-200 µl 0.3M Sodium Cyanate to 10 ml of solution 1. The mixture was inverted several times and then added to 20 ml solution A, and the viscometer test was performed.

Addition of 50-150 µl 0.3M Sodium Cyanate to 20 ml solution A. The mixture was inverted several times and then added to 10 ml solution 1, and the viscometer test was performed.

Results

Table 30 describes results of the viscometer tests. In addition to increased crosslinking time, resulting from the partially blocked amino side groups in the Lysine chains, qualitative observations indicate that crosslinked gels treated with Cyanate groups lead to a more flexible, elastic and adhesive crosslinked gel.

TABLE 30

Viscometer test results

| Cyanate added to | Volume of 0.3M Cyanate used, µl | final crosslinking time, min | Description of crosslinked gel after 1 hour |
|---|---|---|---|
| none | 0 | 2:30-2:45 | Very rigid and stiff, poor flexibility, poor adhesion |
| solution 1 | 100 | 4:30 | Fairly adhesive, fairly flexible, rigid |
| solution 1 | 200 | 7:30 | Good adhesion and flexibility. Amorphous shape. |
| solution A | 50 | 2:34 | Good adhesion and flexibility |
| solution A | 75 | 2:58 | Good adhesion and flexibility |
| solution A | 100 | 2:41 | Very good adhesion and flexibility. |
| solution A | 150 | 3:18 | Very good adhesion and flexibility. |

Example 26

Effect of a Diamine Compound, Putrescine, on the Kinetics of a Gelatin Crosslinking Reaction This Example demonstrates that petruscine slowed down the crosslinking reaction in a dose dependent manner, suggesting that it serves as a substrate for transglutaminase and is crosslinked with the gelatin. Furthermore, the resultant crosslinked gelatin was more elastic.

Materials

The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Putrescine dihydrochloride (Sigma-Aldrich, St. Louis), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCL2, were prepared.

25% (w/w) Gelatin in 3.8M Urea, 0.15M CaCl2, 0.1M Sodium Acetate (control solution), 25% (w/w) Gelatin with 1-1 molar ratio of Putrescine in 3.8M Urea, 0.15M CaCl2, 0.1M Sodium Acetate (Solution A), 25% (w/w) Gelatin with 1½ molar ratio of Putrescine in 3.8M Urea, 0.15M CaCl2, 0.1M Sodium Acetate (Solution B), 25% (w/w) Gelatin with 1¼ molar ratio of Putrescine in 3.8M Urea, 0.15M CaCl2, 0.1M Sodium Acetate (Solution C), 1.25% (w/w) mTG in 0.2M Na-Citrate (solution 1) 0.75% (w/w) mTG in 0.2M Na-Citrate (solution 2), 0.5% (w/w) mTG in 0.2M Na-Citrate (solution 3) and 0.25% (w/w) mTG in 0.2M Na-Citrate (solution 4) were prepared.

Solutions were examined using Qualitative and Elasticity tests.

Qualitative Crosslinking Test

Solutions A, B and C with solutions 1 and 2 were mixed in 2:1 ratio, then moved to 37 C incubator and crosslinking time was defined when an apparent gelation was noticed.

Elasticity Test

The control solution and Solution B were examined for changes in elasticity over time, using mTG3 and mTG4, respectively.

For each elasticity test, 6 ml of gelatin solution were mixed with 3 ml of mTG solution. The resulting mixture was applied to dog-bone mold, 2 ml in each pattern. Molds are incubated in 370 C for 10 min. After the incubation, molds are covered in saline and extracted from the mold.

The specimen is either incubated in saline in RT, or examined immediately. Pattern thickness is measured, and the specimen is placed between the instrument's clamps.

Results

Qualitative Crosslinking Test

Table 31 displays the results for the qualitative crosslinking test, showing that increasing concentrations of putrescine results in increased cross-linking times.

TABLE 31 crosslinking time of the samples

| Gelatin Solution | mTG solution | Gelation time [min] |
|---|---|---|
| A | 2 | 4:00 |
| B | 2 | 3:00 |
| C | 2 | 2:00 |
| A | 1 | 2:40 |
| B | 1 | 2:00 |
| control | 1 | 1:40 |

Elasticity Test

Table 32 displays the average results for the elasticity test; the results are for 2 hr incubation in saline in RT.

TABLE 32 elasticity test results

| Gelatin Solution | mTG solution | Modulus (kPa) | Tensile Stress at Break (kPa) | Tensile Strain at Break (%) |
|---|---|---|---|---|
| Control | 3 | 79.01 | 49.78 | 62.1 |
| B | 4 | 49.18 | 42.61 | 88.05 |

Example 27

Use of an Amine Donor, Polyethylenimine (PEI), to Increase the Elasticity of a mTG-Crosslinked Gelatin Composition Materials The following materials were used in the experiment: Gelita 275 bloom, type A porcine gelatin (Gelita, Sioux City), Urea 99.5% (Sigma-Aldrich, St. Louis), Calcium Chloride (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), Polyethylenimin (PEI) Mw 750,000 (Sigma, St. Louis, Mo.), 10% microbial Transglutaminase—ACTIVA-TG 10% (10% enzyme, 90% maltodextrin) (Ajinomoto, Japan).

Methods

Stock solutions of 0.1M Sodium Acetate buffer pH 6.0, 0.2M Sodium Citrate buffer pH 6.0, 4.5M Urea, 2M CaCL2, were prepared.

25% (w/w) Gelatin solution in 3.8M Urea, 0.15M Ca, 0.1M Sodium Acetate (solution A), 0.75% (w/w) mTG in 0.2M Na-Citrate (solution 1), 0.75% (w/w) mTG with 10% v/v PEI in 0.2M Na-Citrate (solution 2), 0.25% (w/w) mTG in 0.2M Na-Citrate (solution 3) and 0.25% (w/w) mTG with 10% v/v PEI in 0.2M Na-Citrate (solution 4) were prepared.

Viscometer Tests

Viscometer tests were carried out as described in Example 19.

Mechanical Testing with Instron

Mechanical properties, for material characterization, were tested with the Instron device.

For each elasticity test, 6 ml of gelatin solution were mixed with 3 ml of mTG solution. The resulting mixture was applied to dog-bone mold, 2 ml in each pattern. The molds were incubated in 37 C for 10 min. After the incubation, the molds were covered in saline and extracted from the mold.

The specimen was either incubated in saline in room temperature (RT), or examined immediately. Pattern thickness was measured, and the specimen was placed between the instrument's clamps.

Modulus, Tensile Stress at Break and Tensile Strain at Break (degree of elongation) wee calculated for each specimen.

Results

Table 32 summarizes results of solution A which was crosslinked by mTG solutions with and without PEI. Both viscometer and Instron tests were carried out for achieving crosslinking time and mechanical properties of the crosslinked gels. Instron test was carried out after two hours of incubation.

Results indicate that crosslinking time of solution A with mTG containing PEI (solution 2) slightly increases by 7%-14% compared to use of mTG solution with no PEI (solution 1).

Mechanical properties of crosslinked gels containing PEI were much improved as can be seen from comparison between Al with solution 3 and A with solution 4; Modolus of the PEI based crosslinked gel was by 10% lower, and achieved elongation greater by more than 60% compared to crosslinked gel with no PEI, as shown in Table 33.

TABLE 33

Viscometer and Instron tests for gelatin solution reacted with mTG with and without addition of 10% v/v PEI. Instron tests were performed after 2 hours incubation in RT

| Solution A reacted with | Average Crosslinking time, min (30%, 90%) | Average Modulus, kPa | Average Tensile Stress at Break, kPa | Average Tensile Strain at Break, % |
|---|---|---|---|---|
| solution 1 | 1:54, 2:35 | — | — | — |
| solution 2 | 2:03, 2:58 | — | — | — |
| solution 3 | — | 79 | 50 | 62 |
| solution 4 | — | 72 | 74 | 103 |

Example 28

Dispersal of Raw mTG Powder into Foamed Gelatin

This example describes the formation of an appropriate gelatin foam and the dispersal of dry mTG into the foam such that no reaction is immediately detected. Only once the dry composition is reconstituted is crosslinking activity shown.

Materials

The following materials were used in the experiment: Gelita 275 bloom, type A porcine gelatin (Gelita, Sioux City), WFI (Water For Injection; Cure, Israel), 10% microbial Transglutaminase—ACTIVA-TG 10% (10% enzyme, 90% maltodextrin) (Ajinomoto, Japan).

Methods

Gelatin solution for foaming was chosen as 5% w/w in WFI water (this concentration was proved to achieve good gelatin structure while the solvent was chosen as WFI so the Eutectic point will be relative high). The Gelatin solution was maintained at 36-37 Celsius prior to foaming while environment temperature was 21 C-22 C. Gelatin solution at 36 C-37 C was loaded and foamed by a mechanical device. After foaming procedure was complete, 15 g of foam were loaded on each Aluminum tray and then 0.25 g of mTG raw powder (with 90% Maltodextrin) was dispersed with a sieve onto the foam layer. Then additional 15 g of foam were loaded and covered the mTG layer on each tray to achieve total 30 g of foam with less than 1% w/w mTG integrated in every tray. Because it has shown before that raw mTG powder does not react immediately with its substrate due to its low solubility, no cross-linking reaction was observed while loading the trays (no stiffening was detected). All trays were transferred and loaded in to the Freeze Dryer shelves. The testing program started only after all trays were inside the FD, All trays were stored in the same final temperature environment (−40 Celsius). Overall time of the freeze drying program was 36-40 hours.

Reconstitution Test:

The lyophilized pads were extracted from the treys and submerged in water to observe for reconstitution process.

These tests revealed that large areas within the foam matrix did not dissolve. These findings, along with the observation of a typical grey color of the mTG powder in those areas, indicate that part of the foam matrix underwent cross linking reaction and therefore did not dissolve even after 20 minutes.

Example 29 mTG Crosslinking of Recombinant Gelatin

Materials 100 kDa recombinant gelatin (rGelatin) in lyophilized chunks, approximately 2 cm in thickness. ACTIVA TG microbial transglutaminase powder (10% protein, 90% maltodextrin; Ajinomoto, Japan). Phosphate Buffered Saline (PBS), pH 7.4.

Methods

PBS is brought to room temperature (23-25° C.). A 25% w/w solution of rGelatin in PBS is prepared by manually stirring rGelatin into a homogenous solution. Once the solution is thoroughly mixed, it is briefly centrifuged to remove air.

A 7.5% w/w solution of ACTIVA TG in PBS is prepared by manually stirring mTG into a homogenous Solution (mTG solution).

2 mL of rGelatin solution and 1 mL of mTG solution are dispensed into a plastic weighing dish using pipettes Immediately following dispensing, solutions are thoroughly mixed using a pipette tip. The mixed solution is palpated using a pipette tip every 30 seconds to qualitatively assess time of gelation. Once gelation is observed, the sample is manually removed from plate and the elasticity of sample is demonstrated by manually stretching.

The above sample preparation procedure is repeated and the sample is placed in a beaker in a 50° C. bath for 10 minutes. The sample is then subjectively assessed to determine whether it maintains its gel phase or returns to a liquid phase (i.e. to assess thermoreversibility).

Expected Results

It is expected after this process that gelation is observed such that rGelatin is expected to function as a substrate for microbial transglutaminase crosslinking Example 30 mTG Crosslinking of Type B Gelatin

Previous efforts have been made to use mTG to crosslink Type B gelatin. However, while physical gelation of type B gelatin has been recorded, efforts at mTG-crosslinking of type B gelatin has not been successful (Crescenzi et al. *Biomacromolecules*. 2002, 3: p. 1384-1391). Surprisingly, it was found that in an embodiment of the herein invention, where the gelatin was dissolved in acetate buffer and the mTG in citrate buffer, mTG crosslinking of type B gelatin resulted in the formation of a vigorous gel.

Materials

225 Bloom, Type B bovine gelatin (Sigma, St. Louis, Mo.), Sodium Acetate trihydrate (Sigma-Aldrich, St. Louis), Acetic Acid 100% (Ridel-De Haen), Sodium Citrate (Sigma-Aldrich, St. Louis), Citric Acid Monohydrate (Sigma-Aldrich, St. Louis), ACTIVA TG microbial transglutaminase powder (10% protein, 90% maltodextrin; Ajinomoto, Japan).

Methods

The following solutions were prepared: 25% (w/w) gelatin solution in 0.1M Sodium Acetate pH 6.0 at 50° C., 7.5% (w/w) ACTIVA solution in 0.2M Na-Citrate (mTG solution).

A portion of gelatin solution was incubated at room temperature (22-23° C.) and temperature was tracked as it dropped from 50° C. Transition point from liquid solution to physical gel was determined by stirring the gelatin solution periodically as temperature dropped. Physical gelation point was determined as temperature at which stirrer could no longer be used to displace gelatin solution.

Separately, 2 mL aliquots of gelatin solution at 50° C. were mixed with either 1 mL or 2 mL of mTG solution in plastic tubes. These tubes were placed in an incubator at 37° C. The tubes were removed every 30 seconds and inverted to determine if enzymatically crosslinked gel had been formed. Gelation time was defined as the time when the gelatin-mTG mixture no longer flowed upon tube inversion.

Results

The physical sol-gel transition point of the gelatin solution occurred at 30° C. Gelation was observed in both gelatin-mTG compositions within 2 minutes.

These results indicate that type B gelatin can form both a thermoreversible physical gel below about 30° C. and an mTG-crosslinked chemical gel at higher temperatures.

Example 31

Burst Pressure Adhesive Tests

Materials

The materials used for this experiment were type A, 300 bloom, 70 mesh porcine pharmaceutical gelatin (Medex, England batch #80067), 98% urea, dried powder (Alfa Aesar, Lancester: Lot #10110586), 97% $CaCl_2$, dried powder (Alfa Aesar, Lancester: Lot #10110561), 0.1M Sodium Acetate buffer (pH 6.1), 0.5M Sodium Citrate buffer, D-Sorbitol, 97% (Sigma, St. Louis, Mo.: batch #1344776), 10% microbial Transglutaminase—ACTIVA-TG 10% (10% enzyme, 90% maltodextrin) [Ajinomoto, Japan].

Methods

Gelatin Solutions Preparation:
1. Control—25% (w/w) gelatin solution in 0.1M sodium acetate buffer.
2. 25% (w/w) gelatin, 4.5M urea in 0.1M sodium acetate buffer.
3. 25% (w/w) gelatin, 2M urea 1M Ca in 0.1M sodium acetate buffer.

In order to completely dissolve the gelatin powders, the solutions were heated to 40° C. and vigorously stirred. The solutions were then kept in a 24° C. incubator overnight prior to experiment.

Microbial Transglutaminase Solutions Preparation:
Sodium Acetate Solutions:
  a. 5% (w/w) ACTIVA-TG 10% in 0.1M sodium acetate with sorbitol added to a 3:1 w/w ratio, sorbitol:gelatin.
  b. 5% (w/w) ACTIVA-TG 10% in 0.25M sodium acetate with sorbitol added to a 3:1 w/w ratio, sorbitol:gelatin.
  c. 7.5% (w/w) ACTIVA-TG 10% in 0.1M sodium acetate with sorbitol added to a 3:1 w/w ratio, sorbitol:gelatin.
  d. 7% (w/w) ACTIVA-TG 10% in 0.1M sodium acetate.
  e. 7.5% (w/w) ACTIVA-TG 10% in 0.1M sodium acetate with sorbitol added to a 3:1 w/w ratio, sorbitol:gelatin.
Sodium Citrate Solutions:
  f. 2.5% (w/w) ACTIVA-TG 10% in 0.1M sodium citrate.
  g. 3% (w/w) ACTIVA-TG 10% in 0.1M sodium citrate.
  h. 10% (w/w) ACTIVA-TG 10% in 0.1M sodium citrate.
  i. 5% (w/w) ACTIVA-TG 10% in 0.5M sodium citrate with sorbitol added to a 3:1 w/w ratio, sorbitol:gelatin.
  j. 10% (w/w) ACTIVA-TG 10% in 0.5M sodium citrate with sorbitol added to a 3:1 w/w ratio, sorbitol:gelatin.
  k. 5% (w/w) ACTIVA-TG 10% in 0.5M sodium citrate with sorbitol added to a 0.6:1 w/w ratio, sorbitol:gelatin.

Enzyme solutions were filtered using whatman filter paper no. 1 prior to use.

Burst Pressure Tests:

Burst pressure tests were run according to a modified form of ASTM protocol designation F 2392-04.

Burst pressure adhesive tests were run to compare the adhesiveness of different adhesive compositions. For each burst pressure test, collagen sausage casing (Nitta Casings, N.J.) was used as a substrate. A 2-mm diameter hole was punched in each casing specimen and each specimen was clamped into the specimen holding manifold. Then, the tissue manifold was filled with heated (37° C.) physiological fluid (saline solution). Once the manifold was filled, an experimental cross-linking composition was prepared and applied on top of the specimen hole to completely cover the hole with the composition.

Experimental compositions were prepared by mixing 4 mL of cross-linkable protein solution with 2 mL of non-toxic cross-linker in a 25 mL beaker. Then, 4 mL of the mixed solution was pulled into a 5 mL syringe. After gelatin and mTG solutions were mixed in a small beaker, 4 ml of the formed-gel was transferred into a syringe. Then, 3 mL of the composition was applied to cover the specimen hole. After 4 minutes (from the moment of mixing), the burst pressure system was activated and pressure was built up to the indicated level below the hole until the adhesive composition failed and the fluid burst through the specimen hole.

In order to achieve reproducibility, each formulation was tested at least 4 times, unless mentioned otherwise.

Figure 9:
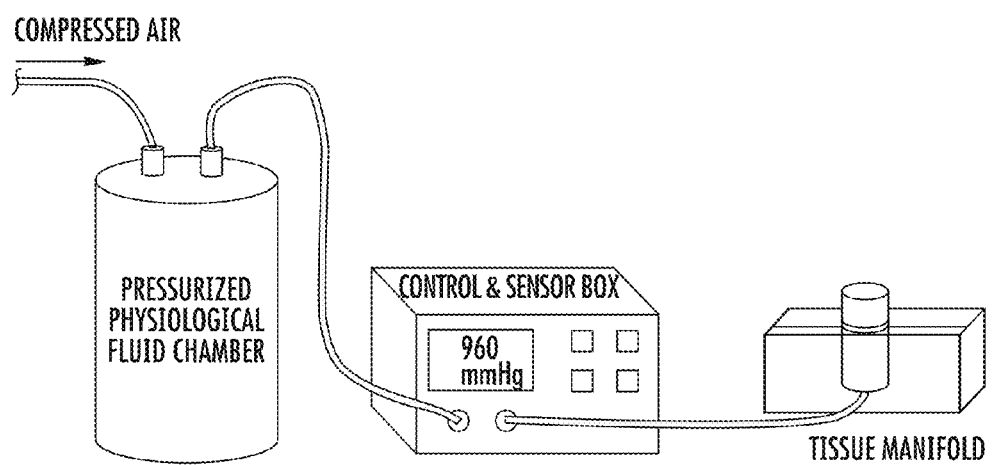
FIG. 9 shows schematics of the burst pressure system and the associated tissue manifold.

Schematics of the burst pressure system and the associated tissue manifold are shown in FIG. 9.

Results

The following tables summarize results of the burst pressure tests of the different gelatin-mTG combinations. The initial atmospheric pressure was measured to be 755 mmHg. Thus, in all cases, the net pressure experienced by the gelatin-mTG composition adhered to the substrate was equal to the recorded pressure value (noted in the results tables) minus 755 mmHg. For example, a recorded value of 855 mmHg indicates that the adhesive strength of the composition being tested in the burst pressure system was 100 mmHg.

Control—25% (w/w) gelatin in 0.1M Na—Ac solution

TABLE 34

Summary of tests using 25% (w/w) gelatin in 0.1M Na—Ac solution with mTG

| # experiment | mTG solution | % mTG in solution | Summary of tests |
|---|---|---|---|
| 1 | 0.1M Na—Ac | 7 | Test 1 - pressure applied was slowly raised to 870 mm Hg. After 4 minutes in that pressure was raised again but test was failed in 884 mm Hg. Cohesive failure from center of formed gel was noticed. Overall time - 8:30 minutes. |

25% (w/w) gelatin, 4.5M urea in 0.1M Na—Ac solution

TABLE 35

Summary of tests using 25% (w/w) gelatin, 4.5M urea in 0.1M Na—Ac solution with different mTG based solutions

| # experiment | mTG solution | % mTG in solution | Summary of tests |
|---|---|---|---|
| 2 | 0.1M Na—Ac | 7 | Test 1 - Formed gel maintained stability in 820-837 mm Hg for 1 minute and failed afterwards (cohesive failure). Overall time - 6 minutes. Test 2 - pressure of 820-828 was maintained for 2 minutes. Applied pressure was raised afterwards and the cross-linked gel failed (cohesive) in 851 mm Hg. Overall time - 8 minutes. |

TABLE 35-continued

Summary of tests using 25% (w/w) gelatin, 4.5M urea in 0.1M Na—Ac solution with different mTG based solutions

| # experiment | mTG solution | % mTG in solution | Summary of tests |
|---|---|---|---|
| | | | Test 3 - Similar to test 2. Gel maintained integrity in range of 820-837 mm Hg for 2 minutes. Failed afterwards (cohesive failure) when pressure was raised to 853. Test 4 - Formed gel failed in 834 mm Hg. Overall time - 4:52. Test 5 - Adhesive and cohesive failure occurred in 808 mm Hg (bubble formation of gel was noticed). Test 6 - Unlike other tests, pressure was applied only after 42 minutes (instead of 4) and pressure was slowly raised. Formed gel failed in 906 mm Hg (cohesive failure) after overall time of 46 minutes. |
| 2 | 0.5M Na-Citrate | 2.5 | Test 1 - an almost immediate failure occurred, in 770 mm Hg. Failure was both cohesive and adhesive. Test 2 - Similar to results of test 1. Bubble formation of the formed gel was noticed. Test 3 - pressure was applied only after 5 minutes, however as in previous tests an almost immediate failure, due to bubble formation, occurred. Cohesive and adhesive failure took place in 790 mm Hg. Overall time - 7 minutes. |
| 3 | 0.1M Na—Ac + sorbitol 3:1 | 7.5% | Test 1 - cohesive failure was occurred during pressure raise in 807 mm Hg. Overall time - 5 minutes. Test 2 - as in test 1. Combined failure (cohesive and adhesive) occurred in 817 mm Hg. Bubble formation was noticed. Test 3 - much alike test 2. Cohesive failure occurred in 813 mm Hg. Overall time - 4:46 minutes. Test 4 - as oppose to previous tests, this time the gelatin and mTG solutions were mixed on the substrate itself. When pressure was applied bubble formation in the formed gel occurred and it failed in 804 mm Hg. Overall time - 5:20 minutes. Test 5 - formed gel maintained integrity in 820-833 mm Hg for 2 minutes. When pressure was raised again, failure occurred in 843 mm Hg. Overall time - 8:15. Test 6 - Combined cohesive and adhesive failure occurred in 825 mm Hg. Overall time - 5:20 minutes. Test 7 - bubble formation caused to an combined cohesive and adhesive failure in 791 mm Hg. Overall time - 5:08 minutes. |
| 4 | 0.5M Na-Citrate + sorbitol 3:1 | 5 | Test 1 - since cross-linked was formed almost immediately; application on the substrate was not uniformed and caused many air bubbles. As a result, failure occurred in the pressure raised sequence and it was also noted that the adhesion was poor. Test 2 - both solutions were mixed inside the syringe and was applied directly on the substrate but result resembled test 1 as failure occurred in the pressure raised stage. Once again, bubble formation was noticed. |
| 5 | 0.1M Na—Ac | 7.5 | Test 1 - cohesive failure through center of gel, at 808 mm Hg. Overall time - 4:50. Good adhesion to the substrate was noticed. Test 2 - test was held while slightly tilting the system, in order to prevent air bubbles gather under the substrate. Cohesive failure occurred at 847 mm Hg. Overall time - 5:30. Good adhesion was reported. Test 3 - cohesive failure occurred at 811 mm Hg. Overall time - 4:50. |

25% (w/w) gelatin, 2M urea 1M Ca in 0.1M Na—Ac solution

TABLE 36

Summary of tests using 25% (w/w) gelatin, 2M urea 1M Ca in 0.1M Na—Ac solution with different mTG based solutions

| # experiment | mTG solution | % mTG in solution | Summary of tests |
|---|---|---|---|
| 6 | 0.1M Na—Ac | 7.5 | Test 1 - an immediate failure in 760 mm Hg. Test 2 - pressure was raised to 820 mm Hg and formed gel maintained integrity for 0:30 minutes. Cohesive failure was noticed although gel possessed poor adhesion as well. Test 3 - much like test 1. Poor adhesion was noticed as well. Test 4 - pressure was raised to 820 mm Hg and formed gel maintained integrity for 0:40 minutes. Cohesive failure was noticed although gel possessed poor adhesion as well. |
| 7 | 0.5M Na-Citrate | 10 | Test 1 - pressure was raised to 820 mm Hg and cross-linked gel maintained formation for 2 minutes. When pressure was raised again, cohesive failure occurred in 840 mm Hg. Poor adhesion of the gel to the substrate was noticed. Overall time - 10 minutes. Test 2 - cohesive failure occurs while pressure was raised, in 800 mm Hg. Overall time - 4:30 minutes. Test 3 - cohesive failure occurs while pressure was raised, in 808 mm Hg. Overall time - 5:30 minutes. Test 4 - adhesive failure occurs while pressure was raised, in 808 mm Hg. Overall time - 5 minutes. |
| 8 | 0.1M Na—Ac | 7.5 | Test 1 - an almost immediate failure due to bubble formation. Failure was reported as cohesive and adhesive, though adhesion was noticed as fairly good. Overall time - 4:20. Test 2 - same as in test 1. |

Similar burst pressure results were obtained with other embodiments of the herein inventions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition comprising a cross-linkable protein comprising gelatin, with the proviso that said protein does not comprise fibrin, and a microbial transglutaminase with specific activity >25 enzyme units per milligram, >95% electrophoretic purity, <5 endotoxin units per gram, and <10 CFU/g, wherein a ratio of an amount of said gelatin and an amount of said microbial transglutaminase is sufficient to reduce bleeding in a wound of a mammal.

2. The composition of claim 1, wherein a protein concentration of said transglutaminase is present in an amount from about 0.0001% to about 2% w/w of the composition.

3. The composition of claim 2, wherein said transglutaminase is present in an amount of from about 0.01% to about 1.35% w/w of the composition.

4. The composition of claim 3, wherein said transglutaminase is present in an amount of from about 0.05% to about 0.5% w/w of the composition.

5. The composition of claim 4, wherein said transglutaminase is present in an amount of from about 0.1% to about 0.4% w/w of the composition.

6. The composition of claim 1, wherein said concentration of transglutaminase is in the range of from about 1 to about 180 enzyme units (U/mL) of total composition.

7. The composition of claim 6, wherein said concentration of transglutaminase is in the range of from about 4 to about 70 enzyme units (U/mL) of total composition.

8. The composition of claim 7, wherein said concentration of transglutaminase is in the range of from about 10 to about 55 enzyme units (U/mL) of total composition.

9. The composition of claim 1 further comprising a plasticizer.

10. The composition of claim 9, wherein said plasticizer is selected from the group consisting of Gum Arabic, Guar Gum, PVA, PEG 6000, Polyvinylpyrrolidone (PVP), citric acid alkyl esters, glycerol esters, phthalic acid alkyl esters, sebacic acid alkyl esters, sucrose esters, sorbitan esters, acetylated monoglycerides, glycerols, fatty acid esters, glycols, propylene glycol, lauric acid, sucrose, glyceryl triacetate, poloxamers, diethyl phthalate, mono- and di-glycerides of edible fats or oils, dibutyl phthalate, dibutyl sebacate, polysorbate, polyethylene glycols 200 to 12,000, Carbowax polyethylene glycols, and a surfactant at a concentration above the CMC (critical micelle concentration) of said surfactant; or a combination thereof.

11. The composition of claim 10, wherein said surfactant comprises a polyoxyethylene-sorbitan-fatty acid ester, polyoxyethyleneglycol dodecyl ether, polyoxyethylene-polyoxypropylene block copolymer, sodium lauryl sulfate, sodium dodecyl sulfate, sodium laureth sulfate, sodium lauryl ether sulfate, poloxamers, poloxamines, alkyl polyglucosides, fatty alcohols, fatty acid salts, cocamide monoethanolamine, and cocamide diethanolamine.

12. The composition of claim 11, wherein a concentration of said surfactant is in the range of from about 0.1% to about 5% w/w of dry weight of said cross-linkable protein.

13. The composition of claim 11, wherein said polyoxyethylene-sorbitan-fatty acid ester comprises one or more of polysorbates 20, 21, 0, 60, 61, 65, 80 or 85.

14. The composition of claim 1, further comprising a viscosity increasing agent selected from the group consisting of Alginate Ester, Gum Arabic, high viscosity Carboxymethyl cellulose (CMC), Xanthan Gum, Guar Gum, and PVP.

15. The composition of claim 1, further comprising one or more of Cystamine, Cysteine, cyanate or Melanin.

16. The composition of claim 1, further comprising a buffer selected from the group consisting of succinate buffer, maleate buffer, tris(hydroxymethyl)methylamine (TRIS), 3-{[tris(hydroxymethyl)methyl]amino}propanesulfonic acid (TAPS), N,N-bis(2-hydroxyethyl)glycine (bicine), N-tris(hydroxymethyl)methylglycine (tricine), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid, N-(2-hydroxyethyl)piperazine-N'-(2-ethane sulfonic acid) (HEPES), and 2-(N-morpholino)ethanesulfonic acid (MES).

17. The composition of claim 1, having a pH in a range of from about 6 to about 7.

18. The composition of claim 1, wherein said gelatin is produced from animal origin, recombinant origin or a combination thereof.

19. The composition of claim 18, wherein said animal origin is selected from the group consisting of fish and mammals.

20. The composition of claim 19, wherein said mammal is selected from the group consisting of pigs and cows.

21. The composition of claim 18, wherein said gelatin is of type A (Acid Treated) or of type B (Alkaline Treated).

22. The composition of claim 1 wherein said gelatin comprises high molecular weight gelatin.

23. The composition of claim 22, wherein said gelatin is at least about 250 bloom.

24. A composition comprising a cross-linkable protein comprising gelatin, with the proviso that said protein does not comprise fibrin, and a microbial transglutaminase with specific activity >25 enzyme units per milligram, >95% electrophoretic purity, <5 endotoxin units per gram, and <10 CFU/g, wherein a ratio of an amount of said gelatin and an amount of said microbial transglutaminase is sufficient to reduce bleeding in a wound of a mammal; wherein said surfactant comprises a polyoxyethylene-sorbitan-fatty acid ester, polyoxyethyleneglycol dodecyl ether, polyoxyethylene-polyoxypropylene block copolymer, sodium lauryl sulfate, sodium dodecyl sulfate, sodium laureth sulfate, sodium lauryl ether sulfate, poloxamers, poloxamines, alkyl polyglucosides, fatty alcohols, fatty acid salts, cocamide monoethanolamine, and cocamide diethanolamine.

25. A composition comprising a cross-linkable protein comprising gelatin, with the proviso that said protein does not comprisefibrin, and a microbial transglutaminase with specific activity >25 enzyme units per milligram, >95% electrophoretic purity, <5 endotoxin units per gram, and <10 CFU/g, wherein a ratio of an amount of said gelatin and an amount of said microbial transglutaminase is sufficient to reduce bleeding in a wound of a mammal; further comprising one or more of Cystamine, Cysteine, cyanate or Melanin.

* * * * *